(12) United States Patent
He et al.

(10) Patent No.: US 11,420,976 B2
(45) Date of Patent: Aug. 23, 2022

(54) HETEROCYCLIC COMPOUNDS AS ANTI-VIRAL AGENTS

(71) Applicant: Enanta Pharmaceuticals, Inc., Watertown, MA (US)

(72) Inventors: Yong He, Lexington, MA (US); Xuechao Xing, Wilmington, MA (US); Guoqiang Wang, Belmont, MA (US); Ruichao Shen, Belmont, MA (US); Brett Granger, Sudbury, MA (US); Jiang Long, Wayland, MA (US); Yat Sun Or, Waltham, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 15 days.

(21) Appl. No.: 17/155,159

(22) Filed: Jan. 22, 2021

(65) Prior Publication Data
US 2021/0238188 A1   Aug. 5, 2021

Related U.S. Application Data

(60) Provisional application No. 63/023,429, filed on May 12, 2020, provisional application No. 63/010,303, filed on Apr. 15, 2020, provisional application No. 62/965,457, filed on Jan. 24, 2020.

(51) Int. Cl.
*C07D 491/048* (2006.01)
*A61K 45/06* (2006.01)

(52) U.S. Cl.
CPC .......... *C07D 491/048* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,010,153 A | 3/1977 | Kajfez et al. |
| 4,511,510 A | 4/1985 | Mauri |
| 4,988,692 A | 1/1991 | Gasc et al. |
| 5,571,809 A | 11/1996 | Hargrave et al. |
| 5,637,697 A | 6/1997 | Finch et al. |
| 5,646,140 A | 7/1997 | Sugg et al. |
| 5,681,833 A | 10/1997 | Castro et al. |
| 7,582,624 B2 | 9/2009 | Carter et al. |
| 8,999,969 B2 | 4/2015 | Mackman et al. |
| 9,732,098 B2 | 8/2017 | Hunt et al. |
| 9,957,281 B2 | 5/2018 | Shook et al. |
| 10,358,441 B2 | 7/2019 | Kim et al. |
| 10,398,706 B2 | 9/2019 | Shook et al. |
| 10,865,215 B2 | 12/2020 | Shook et al. |
| 2006/0040923 A1 | 2/2006 | Carter et al. |
| 2006/0083741 A1 | 4/2006 | Hoffman et al. |
| 2007/0142403 A1 | 6/2007 | Powell et al. |
| 2007/0185094 A1 | 8/2007 | Lattmann et al. |
| 2007/0185096 A1 | 8/2007 | Powell et al. |
| 2007/0293482 A1 | 12/2007 | Dowdell et al. |
| 2008/0139536 A1 | 6/2008 | Dowdell et al. |
| 2009/0274655 A1 | 11/2009 | Grimes et al. |
| 2010/0015063 A1 | 1/2010 | Carter et al. |
| 2010/0168384 A1 | 7/2010 | Mdcaniel et al. |
| 2012/0196846 A1 | 8/2012 | Mackman et al. |
| 2014/0038947 A1 | 2/2014 | Glick et al. |
| 2014/0100365 A1 | 4/2014 | Gavai et al. |
| 2014/0148573 A1 | 5/2014 | Ku et al. |
| 2014/0328796 A1 | 11/2014 | Phadke et al. |
| 2015/0038514 A1 | 2/2015 | Grunenberg et al. |
| 2015/0065504 A1 | 3/2015 | Wang et al. |
| 2015/0299210 A1 | 10/2015 | Bailey et al. |
| 2016/0244460 A1 | 8/2016 | Wang et al. |

(Continued)

FOREIGN PATENT DOCUMENTS

CN    109966244 A    7/2019
EP      0167919 A2   1/1986
(Continued)

OTHER PUBLICATIONS

STN Registry database entry: CAS RN 1348594-72-8 (Entered STN: Dec. 4, 2011) (Year: 2011).
STN Registry database entry: CAS RN 1348849-53-5 (Entered STN: Dec. 5, 2011) (Year: 2011).
STN Registry database entry: CAS RN 1348924-24-2 (Entered STN: Dec. 5, 2011).
STN Registry database entry: CAS RN 1349463-13-3 (Entered STN: Dec. 6, 2011) (Year: 2011).
STN Registry database entry: CAS RN 1349533-81-8 (Entered STN: Dec. 6, 2011).

(Continued)

*Primary Examiner* — Samantha L Shterengarts
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

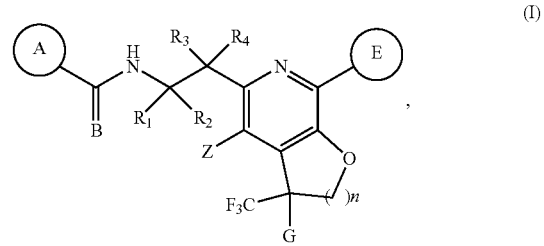

which inhibit Respiratory Syncytial Virus (RSV) or HMPV. The present invention further relates to pharmaceutical compositions comprising the aforementioned compounds for administration to a subject suffering from RSV or HMPV infection. The invention also relates to methods of treating an RSV or HMPV infection in a subject by administering a pharmaceutical composition comprising the compounds of the present invention.

23 Claims, No Drawings

(56) References Cited

U.S. PATENT DOCUMENTS

| | | |
|---|---|---|
| 2017/0022221 A1 | 1/2017 | Blaisdell et al. |
| 2017/0226127 A1 | 8/2017 | Estrada et al. |
| 2017/0226129 A1 | 8/2017 | Yu et al. |
| 2017/0305935 A1 | 10/2017 | Hunt et al. |
| 2017/0355717 A1 | 12/2017 | Hunt et al. |
| 2018/0193352 A1 | 7/2018 | Shook et al. |
| 2018/0237425 A1 | 8/2018 | Kim et al. |
| 2018/0258102 A1 | 9/2018 | Shook et al. |
| 2018/0354912 A1 | 12/2018 | Or et al. |
| 2019/0002478 A1 | 1/2019 | Kim et al. |
| 2019/0002479 A1 | 1/2019 | Kim et al. |
| 2019/0023692 A1 | 1/2019 | Tahri et al. |
| 2019/0040084 A1 | 2/2019 | Yu et al. |
| 2019/0092791 A1 | 3/2019 | Hunt et al. |
| 2019/0152968 A1 | 5/2019 | Blaisdell et al. |
| 2019/0177283 A1 | 6/2019 | Hague |
| 2019/0192535 A1 | 6/2019 | Shook et al. |
| 2019/0202841 A1 | 7/2019 | Hunt et al. |
| 2019/0315766 A1 | 10/2019 | Yu et al. |

FOREIGN PATENT DOCUMENTS

| | | |
|---|---|---|
| EP | 0703222 A1 | 3/1996 |
| WO | 9308175 A1 | 4/1993 |
| WO | 9426718 A1 | 11/1994 |
| WO | 2004026843 A1 | 4/2004 |
| WO | 2004106310 A1 | 12/2004 |
| WO | 2005042530 A1 | 5/2005 |
| WO | 2005089769 A1 | 9/2005 |
| WO | 2005090319 A1 | 9/2005 |
| WO | 2006081389 A1 | 8/2006 |
| WO | 2010103306 A1 | 9/2010 |
| WO | 2011005842 A1 | 1/2011 |
| WO | 2011151651 A1 | 12/2011 |
| WO | 2012068622 A1 | 5/2012 |
| WO | 2012080446 A1 | 6/2012 |
| WO | 2012080447 A1 | 6/2012 |
| WO | 2012080449 A1 | 6/2012 |
| WO | 2012080450 A1 | 6/2012 |
| WO | 2012080451 A1 | 6/2012 |
| WO | 2013096681 A1 | 6/2013 |
| WO | 2013186332 A1 | 12/2013 |
| WO | 2013186334 A1 | 12/2013 |
| WO | 2014031784 A1 | 2/2014 |
| WO | 2014047369 A1 | 3/2014 |
| WO | 2014047397 A1 | 3/2014 |
| WO | 2014060411 A1 | 4/2014 |
| WO | 2014125444 A1 | 8/2014 |
| WO | 2014184350 A1 | 11/2014 |
| WO | 2015026792 A1 | 2/2015 |
| WO | 2015110446 A1 | 7/2015 |
| WO | 2016022464 A1 | 2/2016 |
| WO | 2016055791 A1 | 4/2016 |
| WO | 2016055792 A1 | 4/2016 |
| WO | 2016097761 A1 | 6/2016 |
| WO | 2016138158 A1 | 9/2016 |
| WO | 2017015449 A1 | 1/2017 |
| WO | 2017123884 A1 | 7/2017 |
| WO | 2017175000 A1 | 10/2017 |
| WO | 2019067864 A1 | 4/2019 |
| WO | 2021066922 A1 | 4/2021 |

OTHER PUBLICATIONS

STN Registry database entry: CAS RN 1349749-23-0 (Entered STN: Dec. 6, 2011) (Year: 2011).

STN Registry database entry: CAS RN 1350148-32-1 (Entered STN: Dec. 7, 2011).

PUBCHEM-CID: 10595203, p. 3, Fig, Oct. 25, 2006, 1-9.

"4-(2-Hydroxyethoxy)-3-methoxy-N-[3,3,3-1-22 trifluoro-2-[7-(4-fluorophenyl)-3-[2-(methylamino )ethyl]-2,3-dihydrofuro[2,3-c]pyridin-5-yl]-2-methylpropyl]benzamide", Pubmed Compound Record for CID 139332032, U.S. National Library of Medicine, Nov. 2, 2019, https:l/pubchem.ncbi.nlm.nih.gov/compound/139332032).

"N-[(2R)-2-[3-(Aminomethyl)-7-(4-fluorophenyl)- 1-22 3-methyl-2H-furo[2,3-c]pyridin-5-yl]-3,3,3-trifluoro-2-hydroxypropyl]-4-(2-hydroxyethoxy)-3-methoxybenzamide", Pubmed Compound Record for CID 117924934, U.S. National Library of Medicine, Feb. 23, 2016, https://pubchem.ncbi.nlm.nih.gov/compound/117924934.

Albright, et al., (Document No. 129:54301) retreived from STN; entered in STN on Jun. 17, 1998.

Albright, et al., (Document No. 130:153583) retreived from STN; entered in STN on Feb. 16, 1999.

Andrzej, et al., (Document No. 144:274313) retreved from STN; entered in STN on Mar. 3, 2006.

Aquino, C. J. et al., "Discovery of 1,5-Benzodiazepines with Peripheral Cholecystokinin (CCK-A) Receptor Agonist Activity. 1. Optimization of the Agonist "Trigger"", J. Med. Chem., 39, 1996, 562-569.

Armstrong, et al., "An Efficient Asymmetric Synthesis of (R)-3-Amino-2,3,4,5-tetrahydro-1H-[1]benzazepine-2-one", Tetrahedron Letters, 35(20), 1994, 3239-3242.

Bond, S. et al., "1,2,3,9b-Tetrahydro-5H-imidazo[2,1-a]isoindol-5-ones as a new class of respiratory syncytial virus (RSV) fusion inhibitors. Part 2: Identification of BTA9881 as a preclinical candidate", Bioorg & Med Chem Lett, 25, 2015, 976-981.

Carter, M. C. et al., "1,4-Benzodiazepines as Inhibitors of Respiratory Syncytial Virus", Journal of Medicinal Chemistry, vol. 49, Mar. 9, 2006, 2311-2319.

Chapman, J. et al., "RSV604, a Novel Inhibitor of Respiratory Syncytial Virus Replication", Antimicrobial Agents and Chemotherapy, vol. 51, No. 9, 2007, 3346-3353.

Fordyce, et al., "Discovery of novel benzothienoazepine derivatives as potent inhibitors of respiratory syncytial virus", Bioorganic & Medicinal Chemistry Letters, 27, 2017, 2201-2206.

Heeney, et al., (Document No. 153:359062) retreved from STN; entered in STN on Sep. 2, 2010.

Henderson, E. A. et al., "1,4-Benzodiazepines as Inhibitors of Respiratory Syncytial Virus. The Identification of a Clinical Candidate", Journal of Medicinal Chemistry, vol. 50, Mar. 7, 2007, 1685-1692.

Karmakar, et al., "Crystallization-Induced Dynamic Resolution toward the Synthesis of (S)-7-Amino-5H,7H-dibenzo[b,d]-azepin-6-one: An Important Scaffold for γ-Secretase Inhibitors", Organic Process Research & Development, 20, 2016, 1717-1720.

Lee, et al., (Document No. 140:69941) retrieved from STN; entered in STN on Jul. 8, 2003.

Mackman, R. L. et al., "Discovery of an Oral Respiratory Syncytial Virus (RSV) Fusion Inhibitor (GS-5806) and Clinical Proof of Concept in a Human RSV Challenge Study", J. Med. Chem., 58, 2015, 1630-1643.

Mayo Clinic Staff, Respiratory syncytial virus (RSV) [online], retrieved from from internet on Jun. 25, 2017.; URL http://www.mayoclinic.org/diseases-condiitons/respiratory-syncytial-virus/basics/prevention.

Offel, M. et al., "Synthesis of Substituted 3-Anilino-5-phenyl-l,3-dihydro- 2H-I, 4-benzodiazepine-2-ones and their Evaluation as Cholecystokinin-Ligands", Archiv Der Pharmazie, vol. 339, No. 4, Apr. 1, 2006, 163-173.

Olszewska, W. et al., "Emerging drugs for respiratory syncytial virus infection", Expert Opin. Emerg. Drugs, 14(2), 2009, 207-217.

Peesapati, et al., (Document No. 120:244848) retreved from STN; entered in STN on May 14, 1994.

Perron, M. et al., "GS-5806 Inhibits a Broad Range of Respiratory Syncytial Virus Clinical Isolates by Blocking the Virus-Cell Fusion Process", Antimicrobial Agents and Chemotherapy, 60(3), 2016, 1264-1273.

Reider, et al., "Metalated Allylaminosilane: A New, Practical Reagent for Stereoselective a-Hydroxyallylation of Aldehydes to Erythro-1,2-diol Skeletons", J. Org. Chem, 52, 1987, 957.

Setoi, H. et al., "Preparation of heterocyclylbenzamide derivatives as vasopressin antagonists", Document No. 131:116236, retrieved from STN; entered in STN on Aug. 6, 1999, Aug. 6, 1999.

Sudo, K. et al., "YM-53403, a unique anti-respiratory syncytial virus agent with a novel mechanism of action", Antiviral Research, 2005, vol. 65, 2005, 125-131.

(56) References Cited

OTHER PUBLICATIONS

Wang, et al., (Document No. 160:385666) retreved from STN; entered in STN on Feb. 27, 2014.
Wang, G. et al., "Discovery of 4'-Chloromethyl-2'-deoxy-3',5'-di-O-isobutyryl-2'-fluorocytidine (ALS-8176), a First-in-Class RSV Polymerase Inhibitor for Treatment of Human Respiratory Syncytial Virus Infection", J. Med. Chem., 58, 2015, 1862-1878.
Xiong, et al., (Document No. 160:101182) retreved from STN; entered in STN on Nov. 12, 2013.
Xiong, H., "Discovery of a Potent Respiratory Syncytial Virus RNA Polymerase Inhibitor", Bioorganic & Medicinal Chemistry Letters, 23, 2013, 6789-6793.
Zheng, et al., (Document No. 161:399872) retrieved from STN; entered in STN on Jul. 23, 2014.
"'N-[(2R)-2-[(3S)-3-Amino-7-(3-chloro-4-A fluorophenyl)-3-methyl-2H-furo[2,3-c]pyridin-5-yl]-3,3,3-trifluoro-2-hydroxypropyl]-4-ethoxy-3-methoxybenzamide"', Pubchem Compound Record for CID 117923975, U.S. National Library of Medicine, Feb. 23, 2016 (Feb. 23, 2016), pp. 1-9 (https:l/pubchem.ncbi.nlm.nih.gov/compound/117923975); p. 2.
"'N-[2-[8-[4-Fluoro-3-(1-fluoroethyl)phenyl]-4-iodo-4-methyl-2,3-dihydropyrano[2,3-]pyridin-6-yl]-2-oxoethyl]-3-methoxy-4-[2-[(4-methoxyphenyl)methoxy]ethoxy]benzamide"', Pubchem Compound Record for CID 117924454, U.S. National library of Medicine, Feb. 23, 2016 (Feb. 23, 2016), pp. 1-8 (https:l/pubchem.ncbi.nlm.nih.gov/compound/117924454); p. 2.

HETEROCYCLIC COMPOUNDS AS ANTI-VIRAL AGENTS

RELATED APPLICATIONS

This application claims the benefit of U.S. Provisional Application No. 62/965,457, filed Jan. 24, 2020, U.S. Provisional Application No. 63/010,303, filed Apr. 15, 2020, and U.S. Provisional Application No. 63/023,429, filed May 12, 2020. The entire teachings of the above applications are incorporated herein by reference.

TECHNICAL FIELD

The present invention relates generally to compounds and pharmaceutical compositions useful as inhibitors of Respiratory Syncytial Virus (RSV) and Human metapneumovirus (HMPV).

BACKGROUND OF THE INVENTION

Human respiratory syncytial virus (HRSV) is a negative sense virus, containing a non-segmented, single-stranded linear RNA genome. As a Paramyxovirus of two serotypes in the genus *Pneumoviridae*, HRSV contains 10 genes that encode for 11 proteins. The nucleocapsid protein (N), the RNA polymerase protein (L), the phosphoprotein (P) and the transcription anti-termination factor (M2-1) along with the RNA genome make up the ribonucleoprotein (RNP) complex. Several small-molecule compounds have been shown to target the RNP complex. Additionally, the fusion protein (F), paramount for viral attachment to the host, has been extensively studied. High resolution structures of the F protein interacting with inhibitors have been attained, while structural studies with the N protein are earlier in development. A direct result of the HRSV protein studies and research, the F protein, L protein and N protein have been the major focus of drug discovery efforts.

HRSV is the leading cause of acute lower respiratory infections (ALRI) in patients of all ages. In addition to respiratory infections, patient populations at high risk during HRSV infections include the elderly, immunocompromised, children up to the age of two and patients with chronic obstructive pulmonary disorder (COPD) or chronic heart failure (CHF). HRSV was found over four years to cause 177,500 hospital admissions and 14,000 deaths in the U.S. elderly population. It is well-known that almost all children will be infected with HRSV in the first 3 years after birth and HRSV infection is more severe in premature infants. In fact, HRSV is the most common cause of bronchiolitis and pneumonia in infants under the age of one in the U.S. It is estimated that approximately 3.2 million hospitalizations and 66,000 deaths worldwide in children less than 5 years old are due to HRSV. HRSV has been associated with more deaths of infants below one year old and more infant hospitalizations than influenza.

HRSV infection can also affect healthy individuals and repeated HRSV infections even over the course of two months can occur. Symptoms are similar to colds in healthy individuals, however fever, wheezing, rapid and difficult breathing, and cyanosis occur in more severe cases. Currently, the treatment options for HRSV infection are quite limited and there is no vaccine due to unsuccessful attempts to date. Palivizumab is a monoclonal antibody that is approved for prophylactic use, but its use is limited due to its high price. Palivizumab is generally only used for high risk infants, such as premature infants or those with cardiac/lung disease but has been only 60% effective in reducing hospitalizations. Ribavirin is approved as an inhalation treatment option, but its effectiveness is limited and there are safety concerns associated with it.

There have been several RSV fusion inhibitors that have been disclosed in the following publications: WO2010/103306, WO2012/068622, WO2013/096681, WO2014/060411, WO2013/186995, WO2013/186334, WO 2013/186332, WO 2012 080451, WO 2012/080450, WO2012/080449, WO 2012/080447, WO 2012/080446, WO 2015/110446, WO 2017/009316, *J. Med Chem.* 2015, 58, 1630-1643, *Bioorg. Med Chem. Lett.*, 2015, 25, 976-981 and *Nat. Commun.*, 2017, 8, 167. Examples of other N-protein inhibitors for treatment of HRSV have been disclosed in the following publications: WO 2004/026843, *J. Med Chem.* 2006, 49, 2311-2319, and *J. Med Chem.* 2007, 50, 1685-1692. Examples of L-protein inhibitors for HRSV have been disclosed in the following publications: WO 2011/005842, WO 2005/042530, *Antiviral Res.* 2005, 65, 125-131, and *Bioorg. Med Chem. Lett.* 2013, 23, 6789-6793. Examples of nucleosides/polymerase inhibitors have been disclosed in the following publications: WO 2011/005842, WO 2013/242525, WO 2014/031784, WO 2015/026792, WO 2016/0055791, WO 2016/138158 and *J. Med Chem.* 2015, 58, 1862-1878.

Taking into account of the treatment options, and the consistent seasonality of the HRSV epidemic, the development of new therapeutic agents for the treatment of HRSV is desirable.

Human metapneumovirus (HMPV) is also a negative-sense, single-stranded RNA enveloped virus, that belongs to the *Pneumoviridae* family and *Metapneumovirus* genus. The virus, which was discovered by van Den Hoogen in 2001, is the second most common cause of acute lower respiratory tract infections (ALRTIs) in children, after HRSV. Although often mild, this virus can be serious and life-threatening in high-risk groups, such as children under the age of 5 years, elderly adults over the age of 65 years, and adults with underlying disease (e.g., Chronic Obstructive Pulmonary Disease (COPD), asthma, congestive heart failure, or diabetes). In immunocompromised individuals, HMPV is responsible for 6% of total respiratory infections in lung transplants and 3% of lower respiratory infections associated with stem cell transplant. HMPV infection is also thought to be associated with acute graft rejection. Like HRSV, infection is thought to involve attachment of the virion to the target cell via the glycoprotein (G) protein interactions, followed by fusion via the F protein. HMPV L protein sequence is homologous to HRSV L protein.

HMPV infection is the second most common cause of lower respiratory tract infection in children (behind HRSV) and also problematic for the elderly population. There are 4 subtypes of HMPV found in clinical isolates (A1, A2, B1 and B2). Reinfection occurs throughout childhood following initial infection. No therapeutics are currently available for HMPV infection.

Taking into account the seasonality and predictability of the HRSV and HMPV epidemics, and the severity of infection in high risk group such as infants, immunocompromised patients and the elderly adults over the age of 65 years, the need for a potent and effective treatment for both HRSV and HMPV is clear. The present invention has identified heterocyclic compounds that are that are potent inhibitors of both HRSV-A/B and HMPV. The invention includes methods to prepare these compounds, methods for RSV/HMPV cell-based assays and methods of using these compounds to treat HRSV and/or HMPV infections.

SUMMARY OF THE INVENTION

The present invention provides compounds represented by Formula (I), and pharmaceutically acceptable salts, esters and prodrugs thereof that can be used to treat or prevent viral infection, such as infection by HRSV or HMPV:

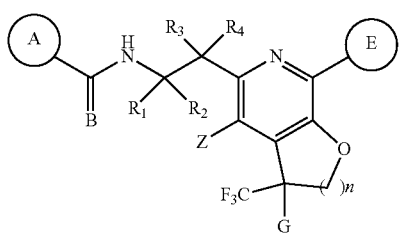

(I)

wherein:
A is an optionally substituted aryl or optionally substituted heteroaryl;
B is O or S;
$R_1$ and $R_2$ are each independently hydrogen or an optionally substituted $C_1$-$C_4$ alkyl; alternatively, $R_1$ and $R_2$ are taken together with carbon atom to which they are attached to form an optionally substituted 3-6-membered cyclic ring;
$R_3$ is selected from the group consisting of hydrogen, hydroxy, and optionally substituted $C_1$-$C_6$ alkoxy;
$R_4$ is selected from the group consisting of hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_6$ cycloalkyl, and optionally substituted 3-6-membered heterocyclic;
Z is selected from the group consisting of hydrogen, halogen, cyano, optionally substituted $C_1$-$C_6$ alkyl, optionally substituted $C_3$-$C_6$ cycloalkyl, and optionally substituted $C_1$-$C_6$ alkoxy;
E is an optionally substituted aryl, optionally substituted heteroaryl, or optionally substituted heterocyclic;
G is —$NR_5R_6$;
$R_5$ and $R_6$ are each independently selected from:
  1) hydrogen,
  2) optionally substituted $C_1$-$C_6$ alkyl,
  3) optionally substituted $C_3$-$C_6$ cycloalkyl,
  4) optionally substituted 3-6-membered heterocyclic,
  5) optionally substituted aryl,
  6) optionally substituted heteroaryl,
  7) —C(=O)$R_7$,
  8) —C(=O)O$R_7$,
  9) —C(=O)NH$R_7$,
  10) —C(=NH)$R_7$,
  11) —C(=NH)NH$R_7$,
  12) —C(=NH)NHCN,
  13) —C(=NH)NHC(=O)$R_7$,
  14) —$SO_2R_7$, and
  15) —$SO_2$NH$R_7$,
  alternatively, $R_5$ and $R_6$ are taken together with the nitrogen atom to which they are attached to form an optionally substituted 3-8-membered heterocyclic ring;
$R_7$ is selected from the group consisting of hydrogen, optionally substituted $C_1$-$C_6$ alkyl, optionally substituted $C_3$-$C_6$ cycloalkyl, optionally substituted 3-6 membered heterocyclic, optionally substituted aryl, and optionally substituted heteroaryl; and n is 1, 2 or 3.

DETAILED DESCRIPTION OF THE INVENTION

In one embodiment of the present invention is a compound of Formula (I) as described above, or a pharmaceutically acceptable salt thereof.

In certain embodiments of the compounds of Formula (I), B is O.

In certain embodiments of the compounds of Formula (I), $R_1$ is hydrogen or F.

In certain embodiments of the compounds of Formula (I), $R_2$ is hydrogen or F.

In certain embodiments of the compounds of Formula (I), Z is hydrogen, Cl or F.

In certain embodiments of the compounds of Formula (I), $R_1$ is hydrogen, $R_2$ is hydrogen, and Z is hydrogen.

In certain embodiments of the compounds of Formula (I), $R_3$ is —OH.

In certain embodiments of the compounds of Formula (I), $R_4$ is optionally substituted methyl or optionally substituted cyclopropyl.

In certain embodiments of the compounds of Formula (I), $R_3$ is OH, and $R_4$ is $CH_3$, $CH_2F$, $CHF_2$, $CF_3$, $CH_2OH$, $CH_2OMe$, optionally substituted isopropyl, optionally substituted cyclopropyl or optionally substituted tert-butyl.

In certain embodiments of the compounds of Formula (I), $R_3$ is OH, and $R_4$ is selected from the groups set forth below:

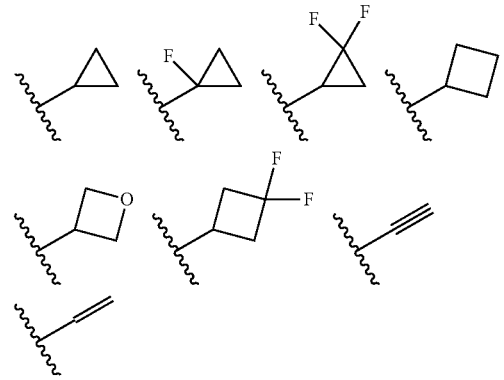

In certain embodiments of the compounds of Formula (I), $R_1$ is hydrogen, $R_2$ is hydrogen, Z is hydrogen, $R_3$ is OH, and $R_4$ is $CH_3$, $CH_2F$, $CHF_2$, $CF_3$, cyclopropyl or tert-butyl.

In certain embodiments of the compounds of Formula (I), $R_5$ is hydrogen or methyl and $R_6$ is as defined above. In other embodiments, $R_5$ and $R_6$ are both hydrogen.

In certain embodiments of the compounds of Formula (I), G is —NHC(=O)$R_7$, —NHC(=O)O$R_7$, or —NHSO$_2R_7$.

In certain embodiments of the compounds of Formula (I), G is selected from the group set forth below,

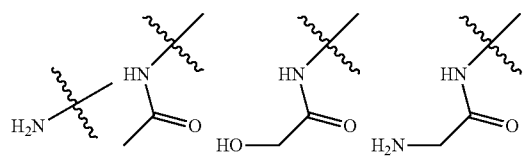

-continued
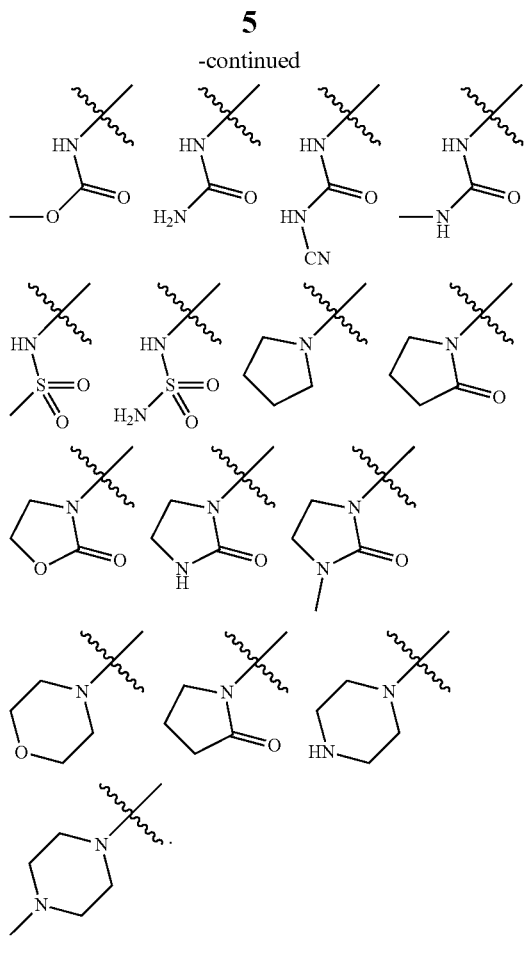
In certain embodiments of the compounds of Formula (I), E is optionally substituted aryl, preferably optionally substituted phenyl.
In certain embodiments of the compounds of Formula (I), E is selected from the group set forth below,
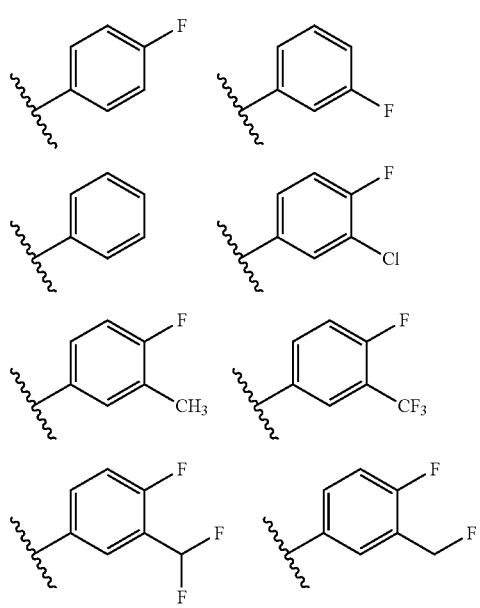
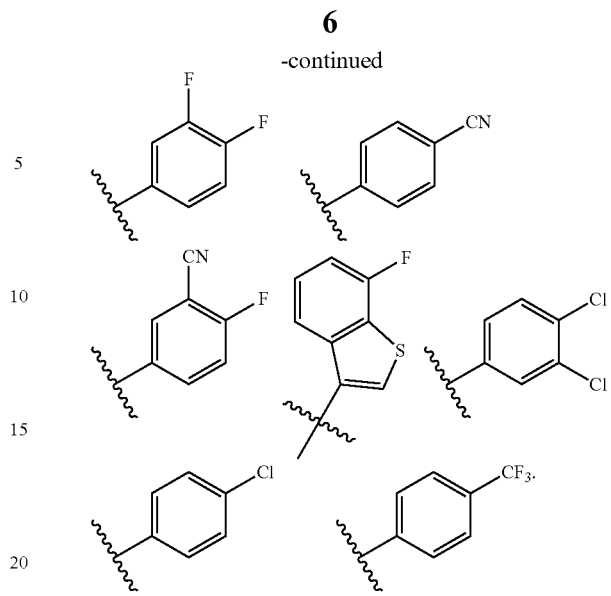
In certain embodiments of the compounds of Formula (I), A is selected from one of the following by removal of a hydrogen atom:
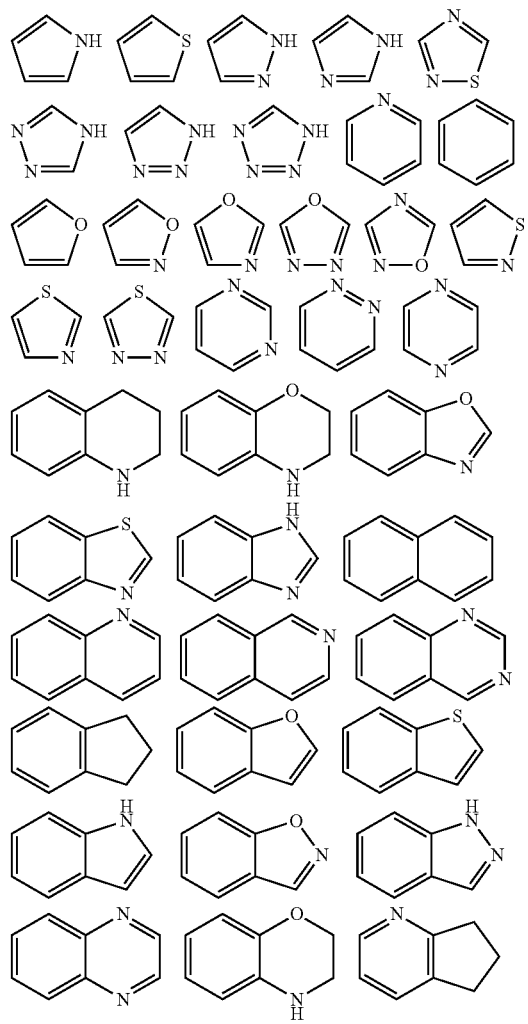

-continued
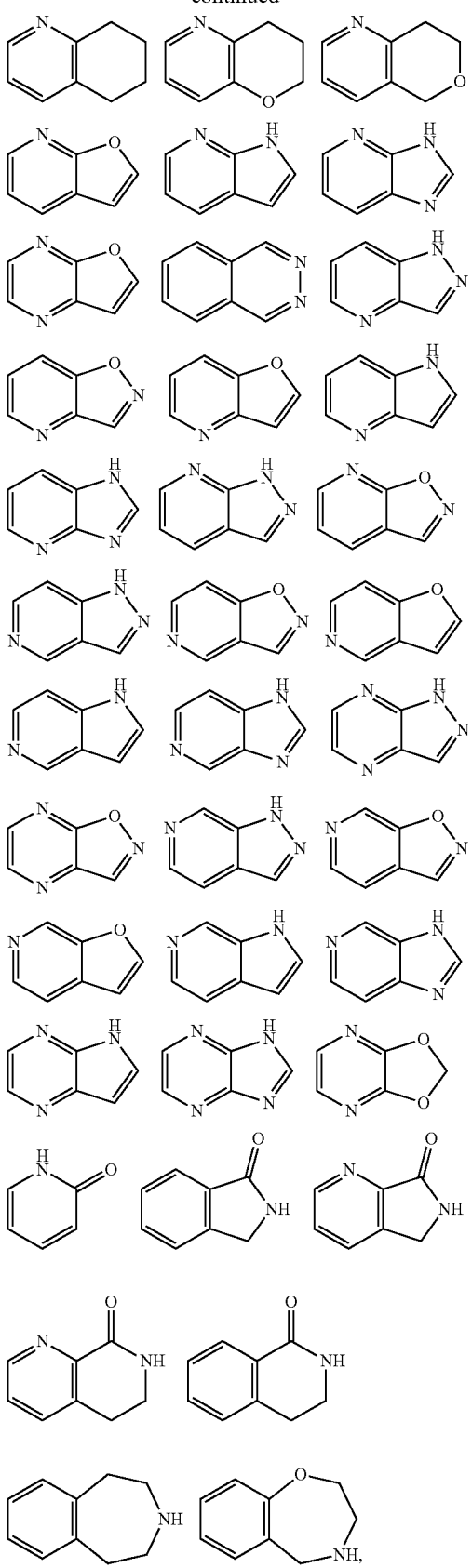
wherein each of these groups is optionally substituted.
In certain embodiments of the compounds of Formula (I), A is selected from the groups set forth below,
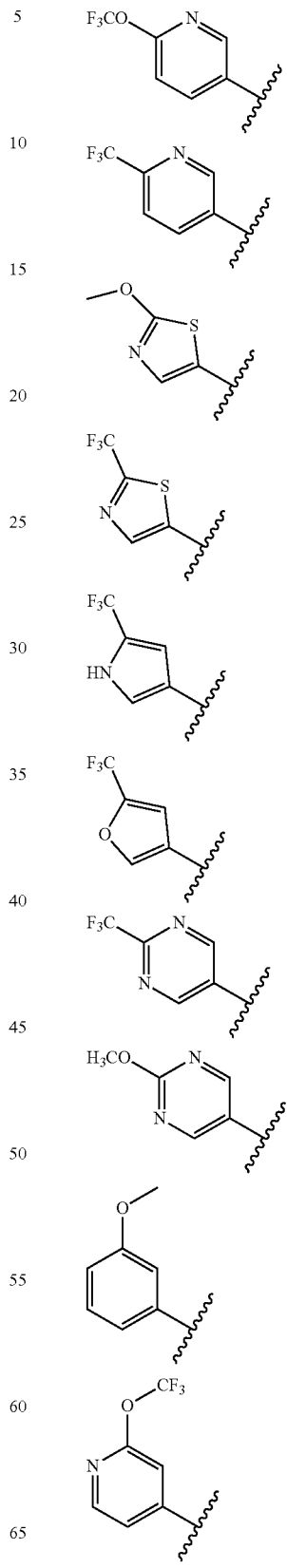

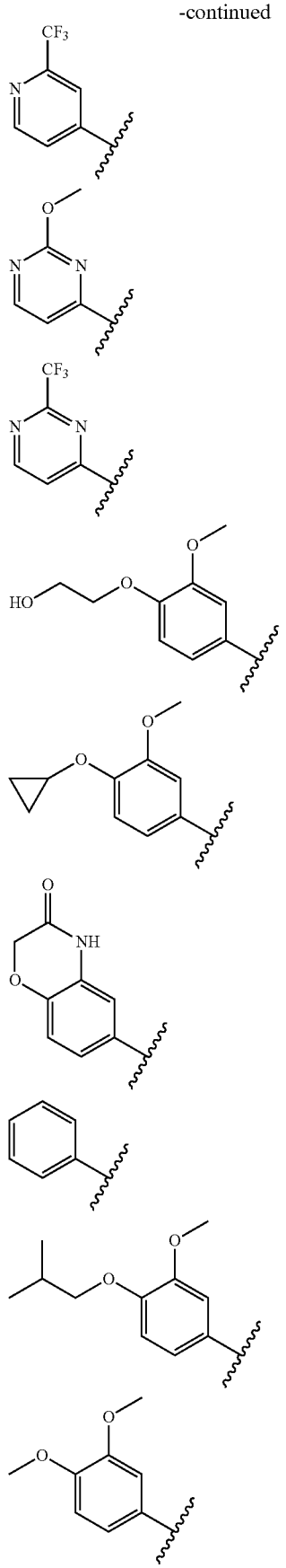
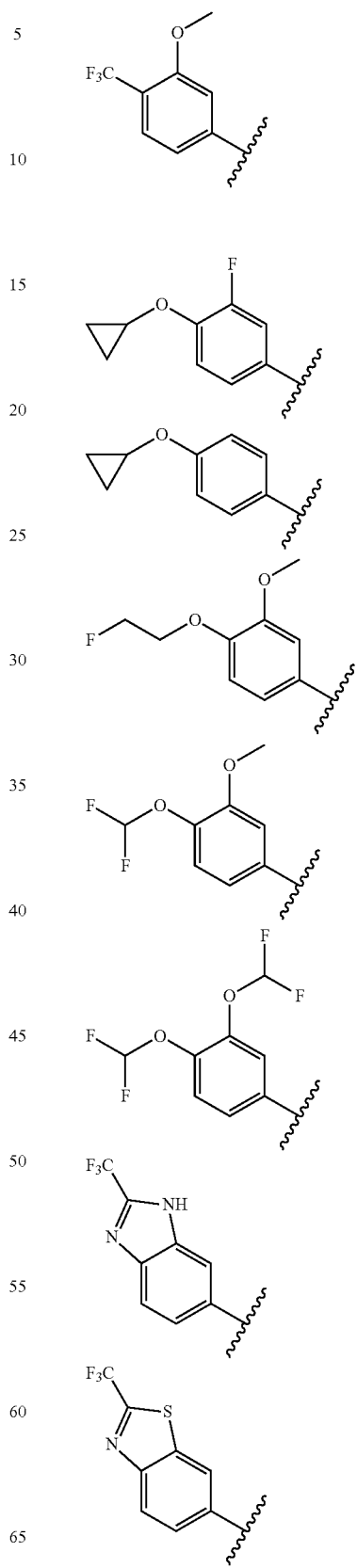

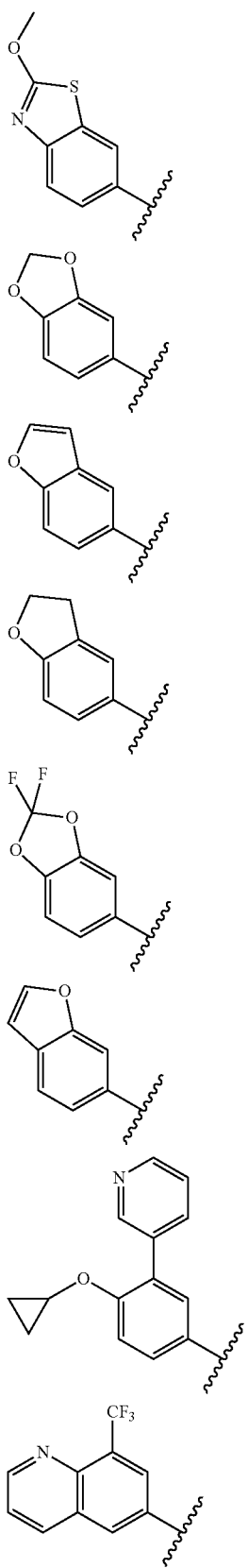
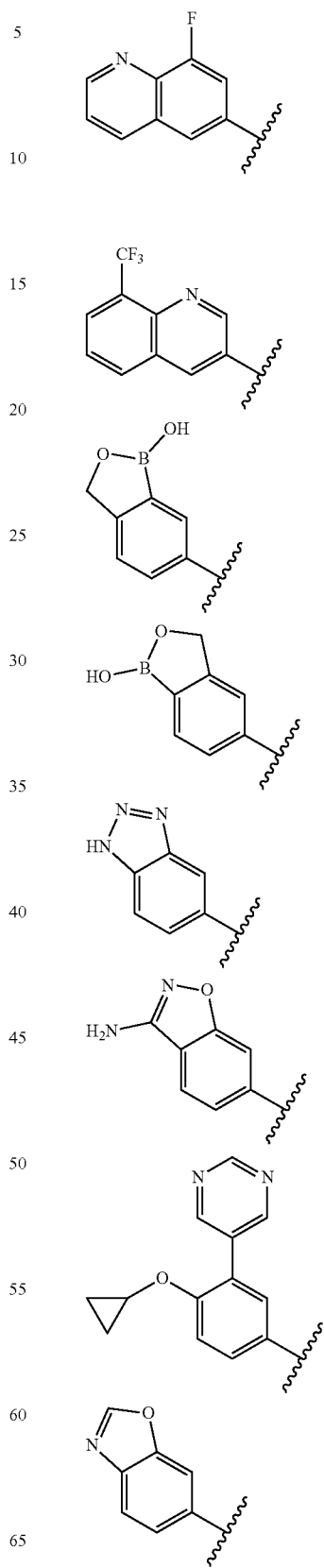

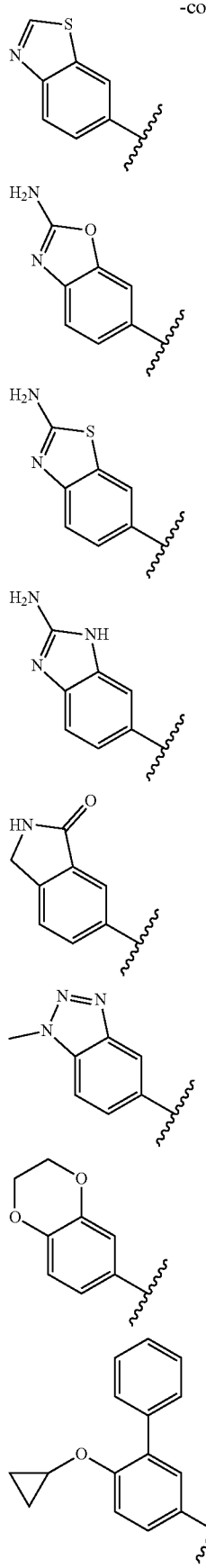
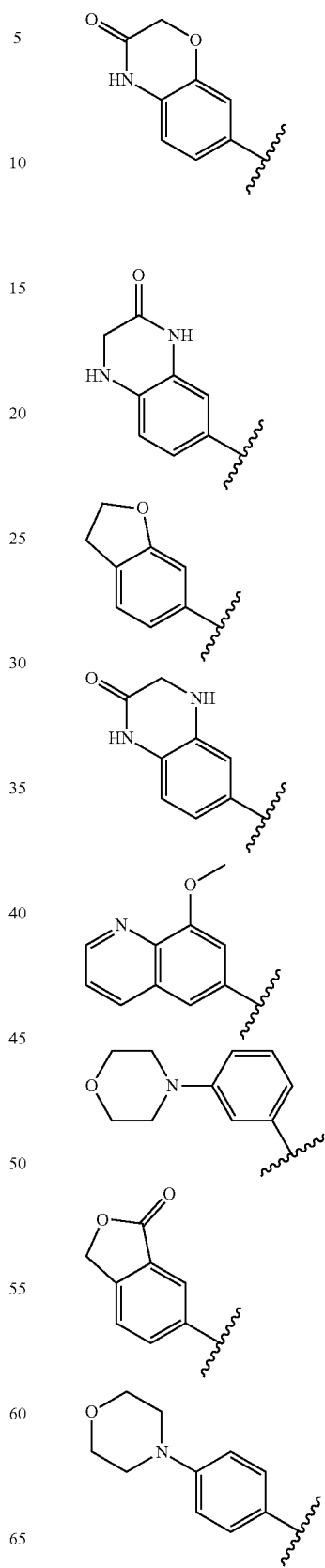

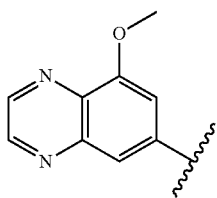
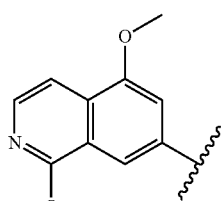
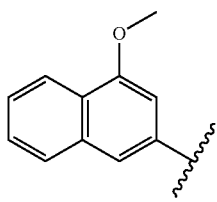
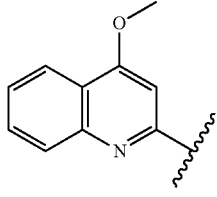
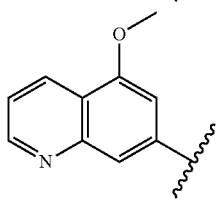
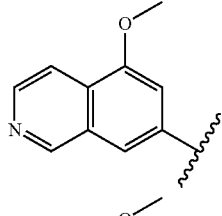
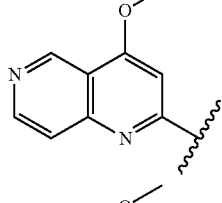
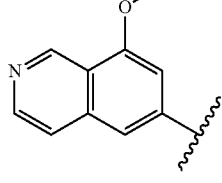
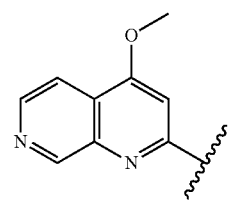
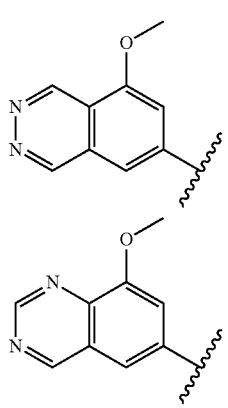
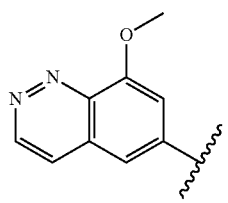
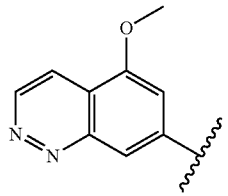
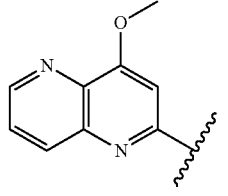
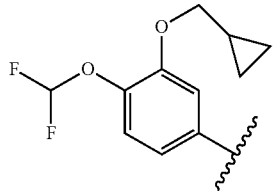
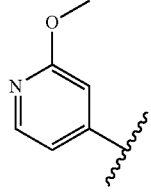

-continued

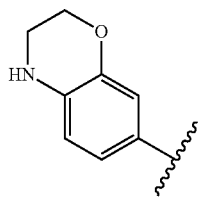

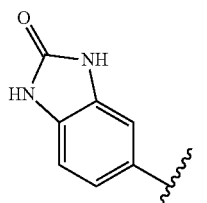

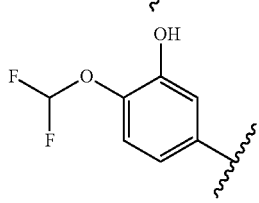

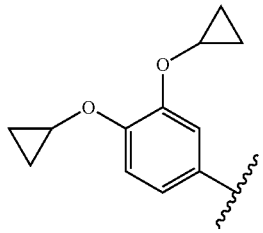

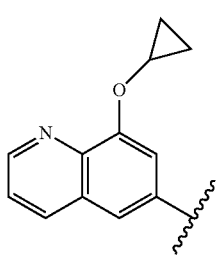

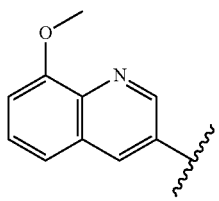

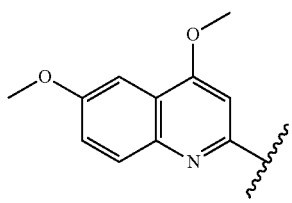

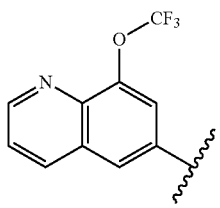

-continued

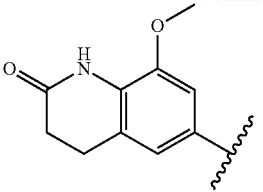

wherein B in these groups represents boron, and each of these groups is optionally further substituted.

In certain embodiments of the compounds of Formula (I), A is selected from the groups set forth below,

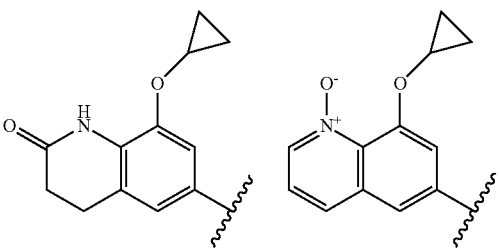

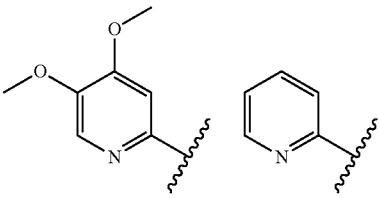

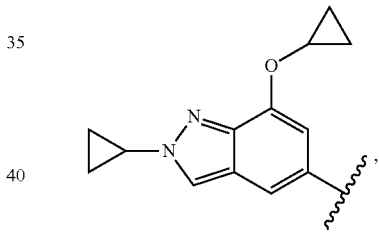

wherein each of these groups is optionally further substituted.

In certain embodiments of the compounds of Formula (I), A is selected from the groups set forth below,

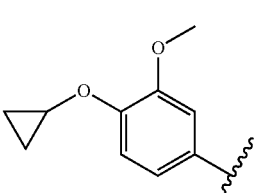

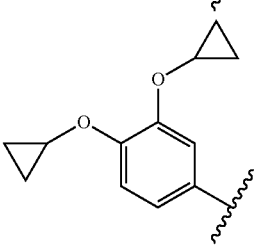

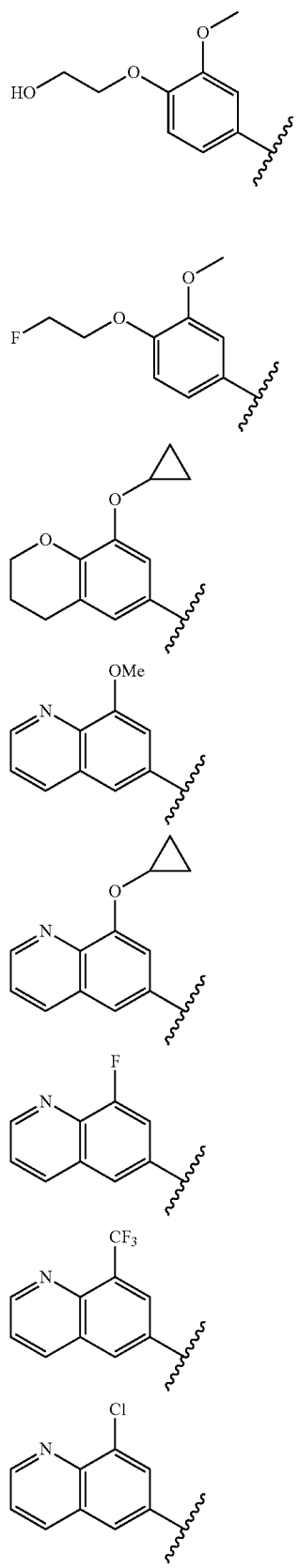
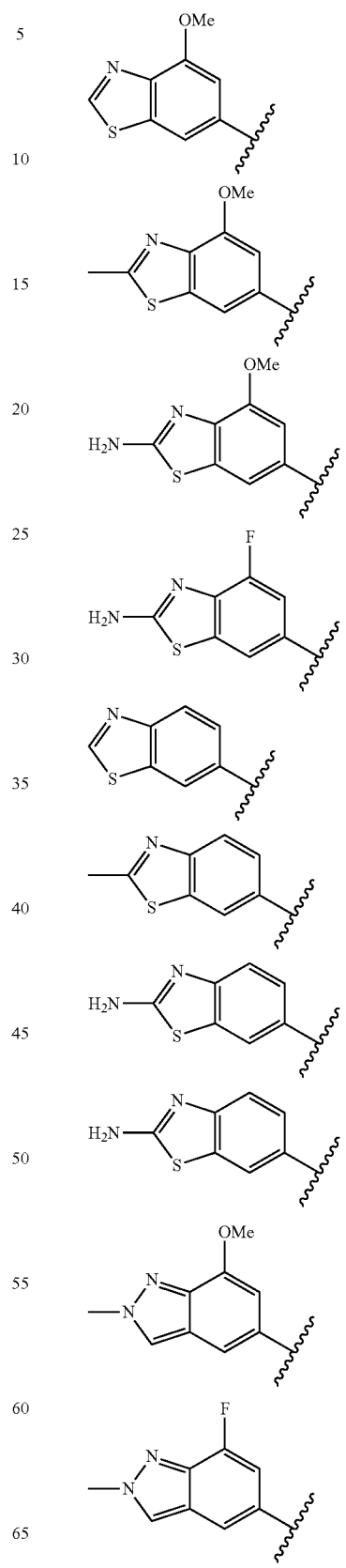

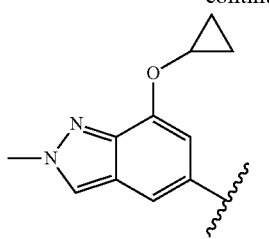
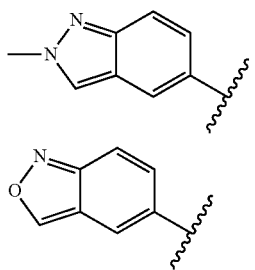
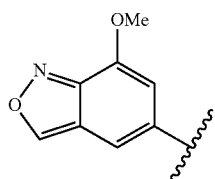
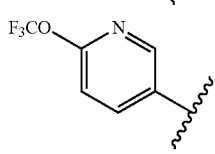
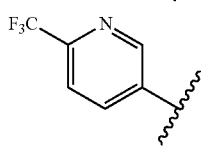
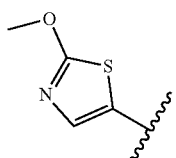
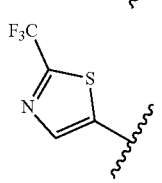
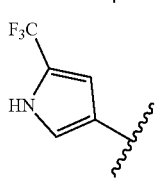
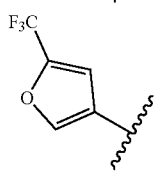
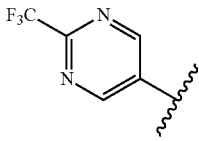
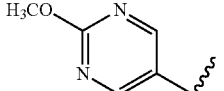
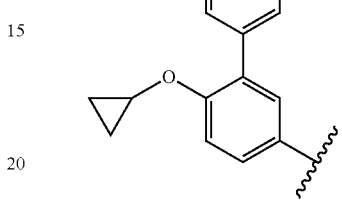
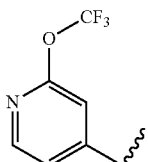
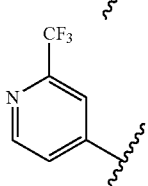
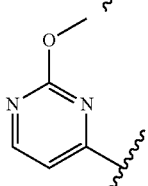
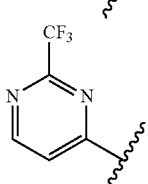
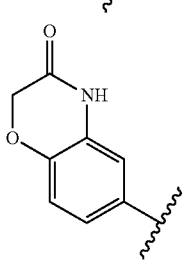
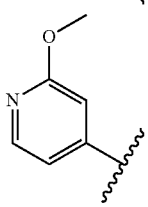

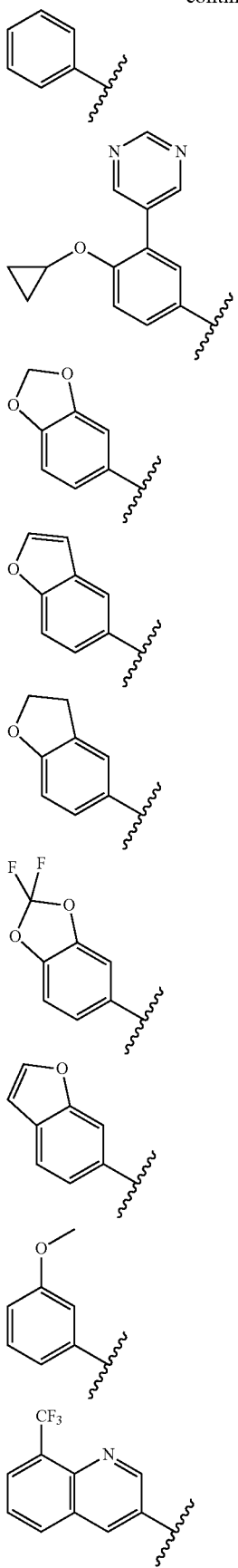
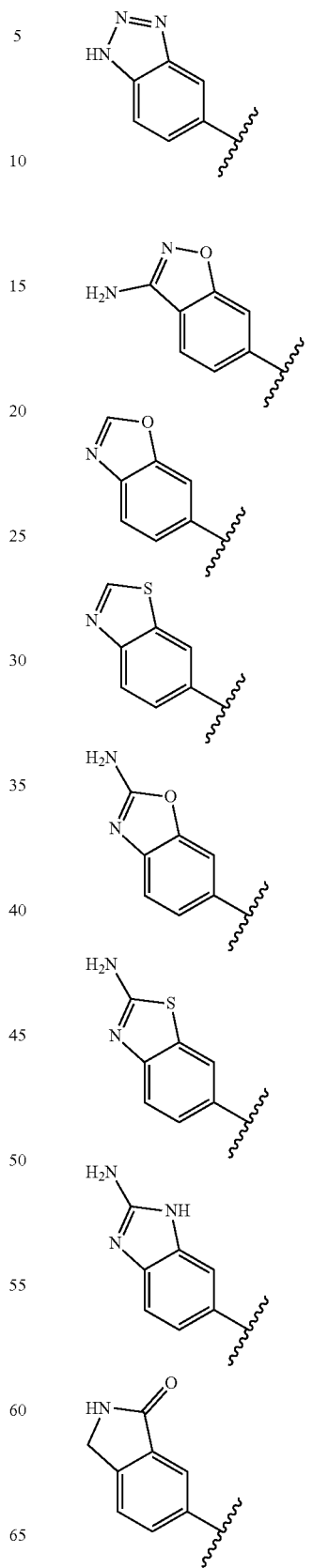

-continued
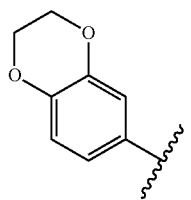
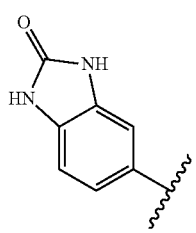
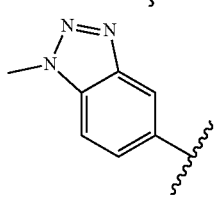
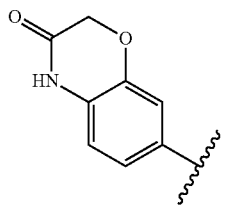
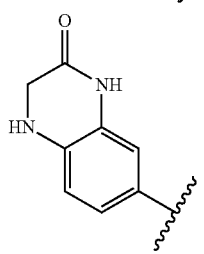
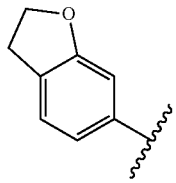
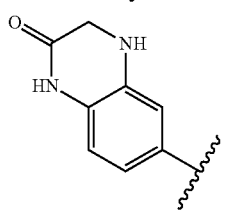
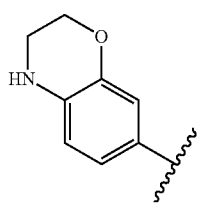
-continued
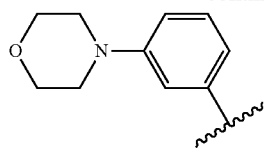
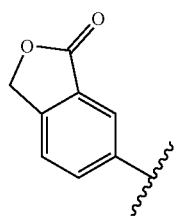
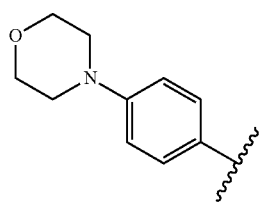
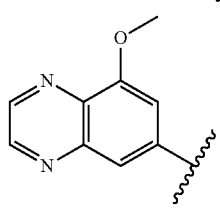
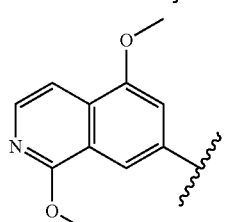
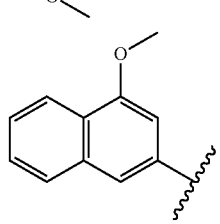
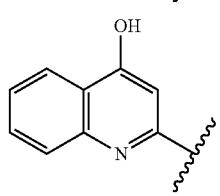
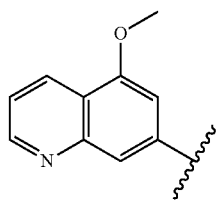

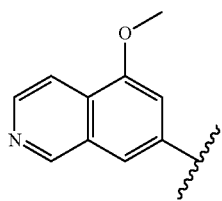
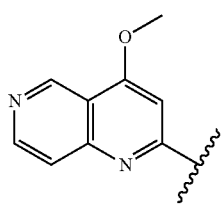
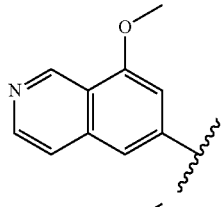
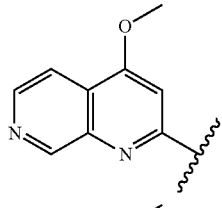
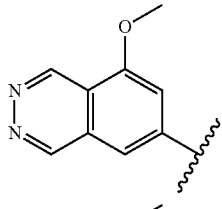
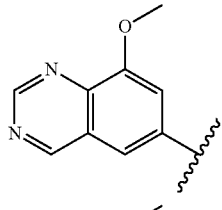
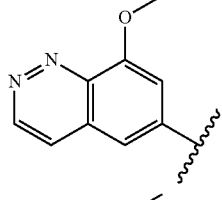
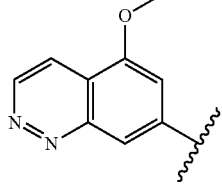

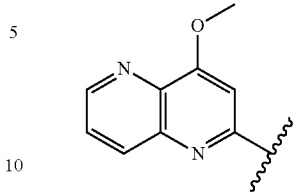

wherein each of these groups is optionally further substituted.

In one embodiment of the present invention, the compound of Formula (I) is represented by Formula (Ia) or Formula (Ib), or a pharmaceutically acceptable salt, ester or prodrug thereof:

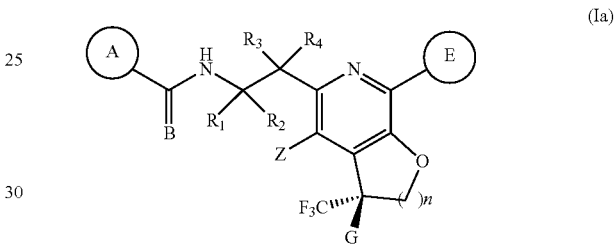

(Ia)

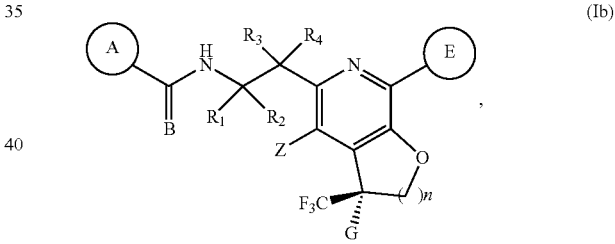

(Ib)

wherein A, B, $R_1$, $R_2$, Z, G, n, E, $R_3$, and $R_4$ are as previously defined.

In a preferred embodiment, the compound of Formula (I) has the stereochemistry shown in Formula (Ib).

In one embodiment of the present invention, the compound of Formula (I) is represented by Formula (IIa) or Formula (IIb), or a pharmaceutically acceptable salt, ester or prodrug thereof:

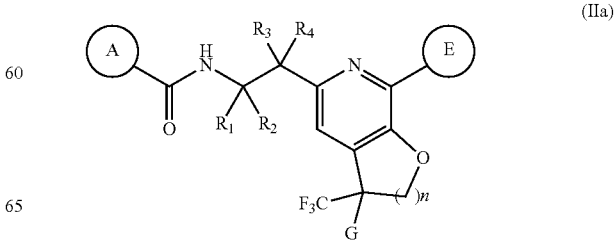

(IIa)

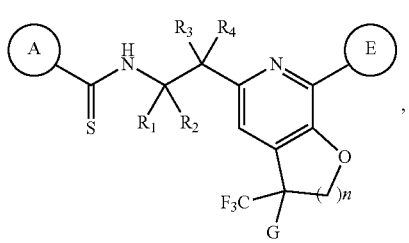
(IIb)

wherein A, $R_1$, $R_2$, G, n, E, $R_3$, and $R_4$ are as previously defined.

In one embodiment of the present invention, the compound of Formula (I) is represented by Formula (IIIa) or Formula (IIIb), or a pharmaceutically acceptable salt, ester or prodrug thereof:

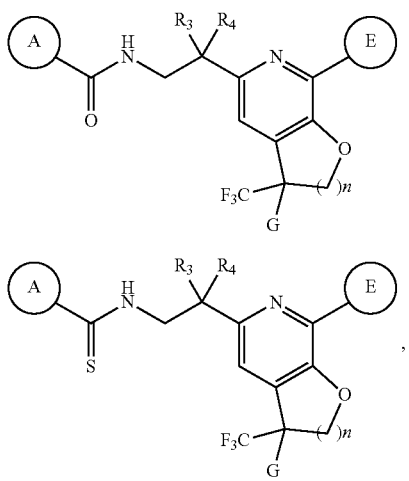
(IIIa)

(IIIb)

wherein A, G, n, E, $R_3$, and $R_4$ are as previously defined.

In one embodiment of the present invention, the compound of Formula (I) is represented by one of Formulas (IVa) to (IVd), or a pharmaceutically acceptable salt, ester or prodrug thereof:

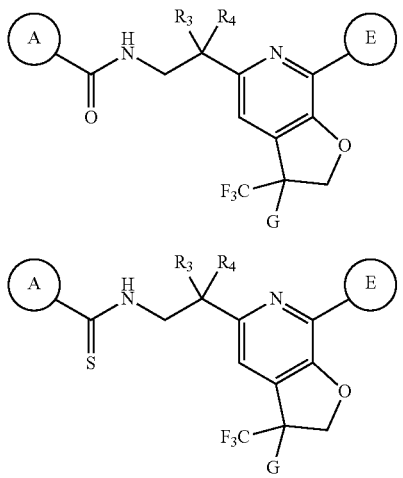
(IVa)

(IVb)

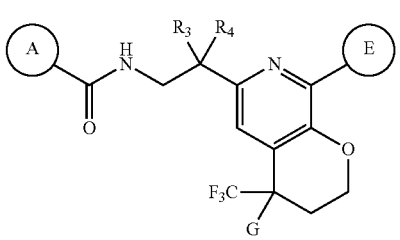
(IVc)

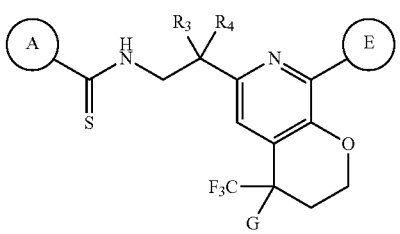
(IVd)

wherein A, G, E, $R_3$, and $R_4$ are as previously defined.

In one embodiment of the present invention, the compound of Formula (I) is represented by one of Formulas (Va) to (Vd), or a pharmaceutically acceptable salt, ester or prodrug thereof:

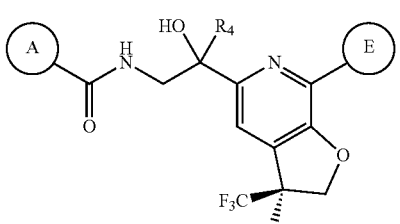
(Va)

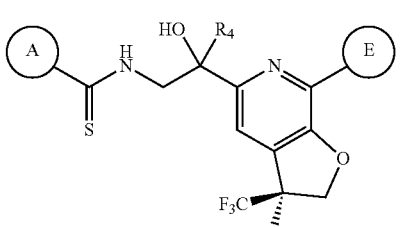
(Vb)

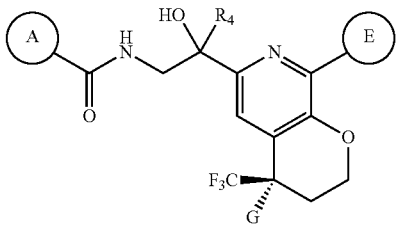
(Vc)

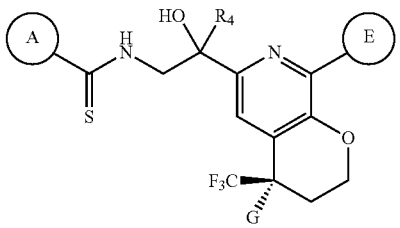
(Vd)

wherein A, G, E, and $R_4$ are as previously defined.

In one embodiment of the present invention, the compound of Formula (I) is represented by one of Formulas (Va') to (Vd'), or a pharmaceutically acceptable salt, ester or prodrug thereof:

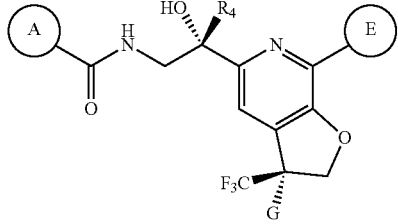
(Va')

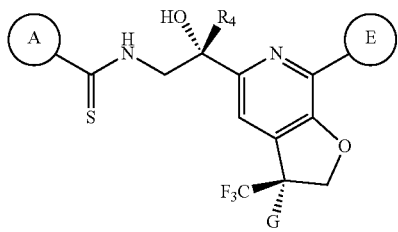
(Vb')

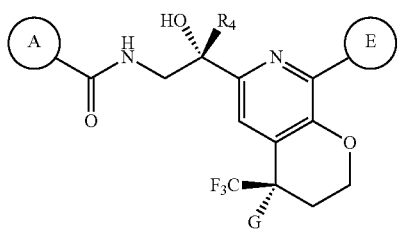
(Vc')

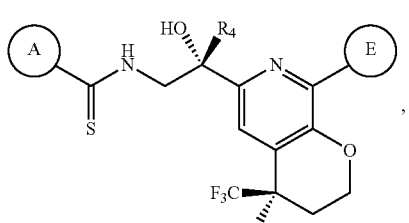
(Vd')

wherein A, G, E, and $R_4$ are as previously defined.

In one embodiment of the present invention, the compound of Formula (I) is represented by Formula (VIa) or (VIb), or a pharmaceutically acceptable salt, ester or prodrug thereof:

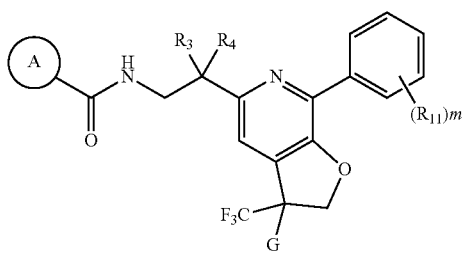
(VIa)

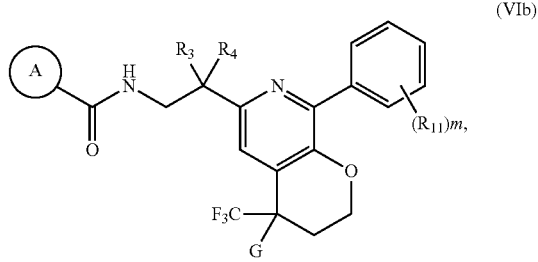
(VIb)

wherein each $R_{11}$ is independently optionally substituted —$C_1$-$C_6$ alkyl, optionally substituted $C_1$-$C_6$ alkoxyl, optionally substituted —$C_3$-$C_6$ cycloalkyl, halo, —CN, or —$NR_7R_8$; m is 0, 1, 2, 3, 4 or 5; $R_8$ is selected from the group consisting of hydrogen, optionally substituted $C_1$-$C_6$ alkyl, optionally substituted $C_3$-$C_6$ cycloalkyl, optionally substituted 3-6 membered heterocyclic, optionally substituted aryl, and optionally substituted heteroaryl; A, G, $R_3$, $R_4$ and $R_7$ are as previously defined.

In one embodiment of the present invention, the compound of Formula (I) is represented Formula (VIIa) or (VIIb), or a pharmaceutically acceptable salt, ester or prodrug thereof:

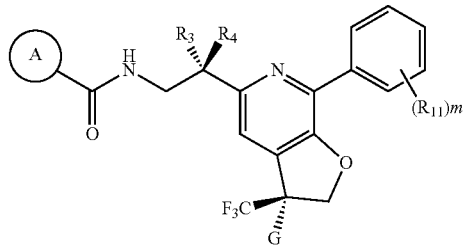
(VIIa)

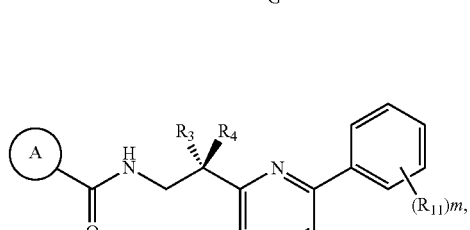
(VIIb)

wherein A, G, $R_3$, $R_4$, $R_{11}$, and m are as previously defined.

In one embodiment of the present invention, the compound of Formula (I) is represented by one of Formulas (VIIIa) to (VIIIf), or a pharmaceutically acceptable salt, ester or prodrug thereof:

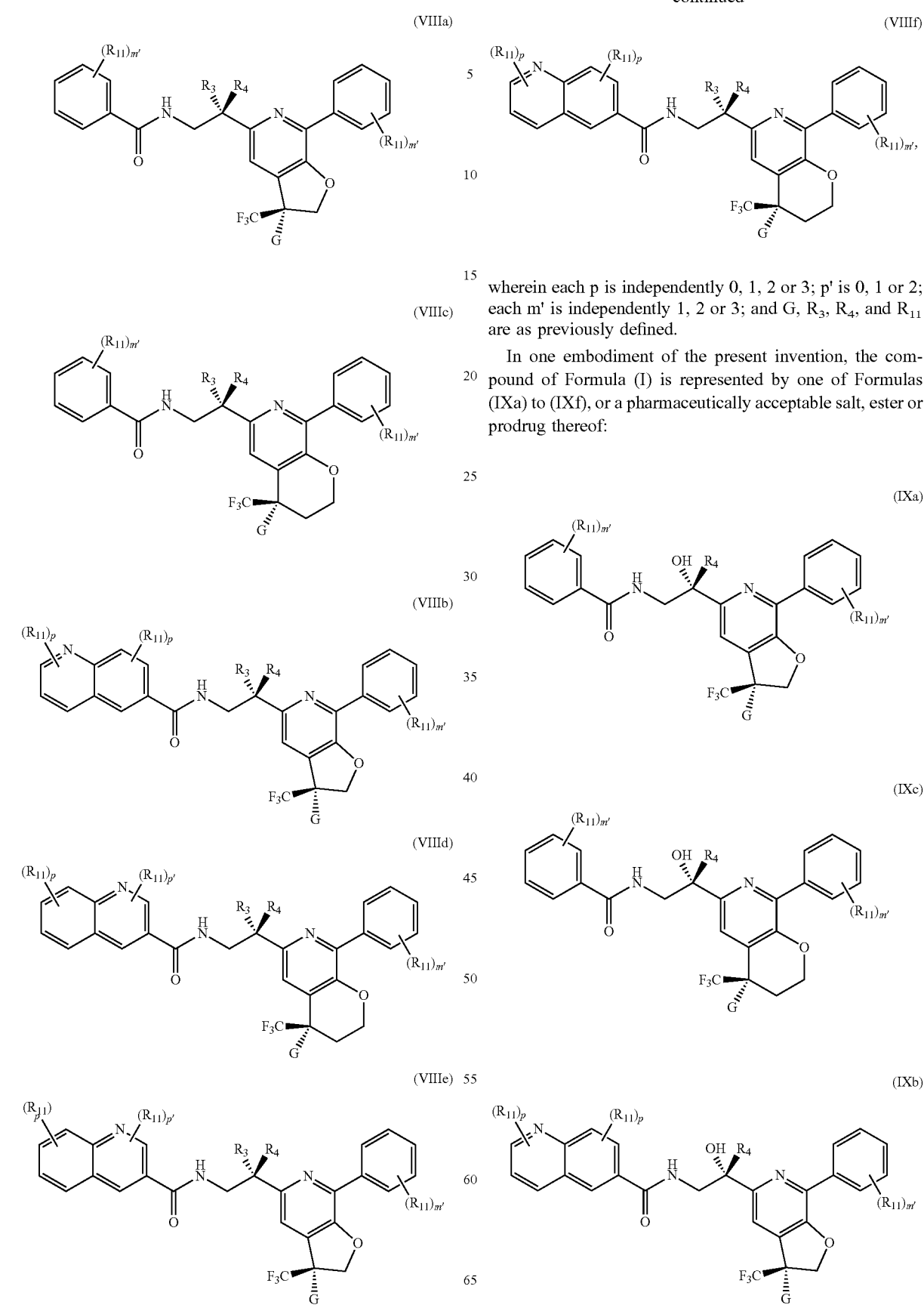
wherein each p is independently 0, 1, 2 or 3; p' is 0, 1 or 2; each m' is independently 1, 2 or 3; and G, R$_3$, R$_4$, and R$_{11}$ are as previously defined.
In one embodiment of the present invention, the compound of Formula (I) is represented by one of Formulas (IXa) to (IXf), or a pharmaceutically acceptable salt, ester or prodrug thereof:

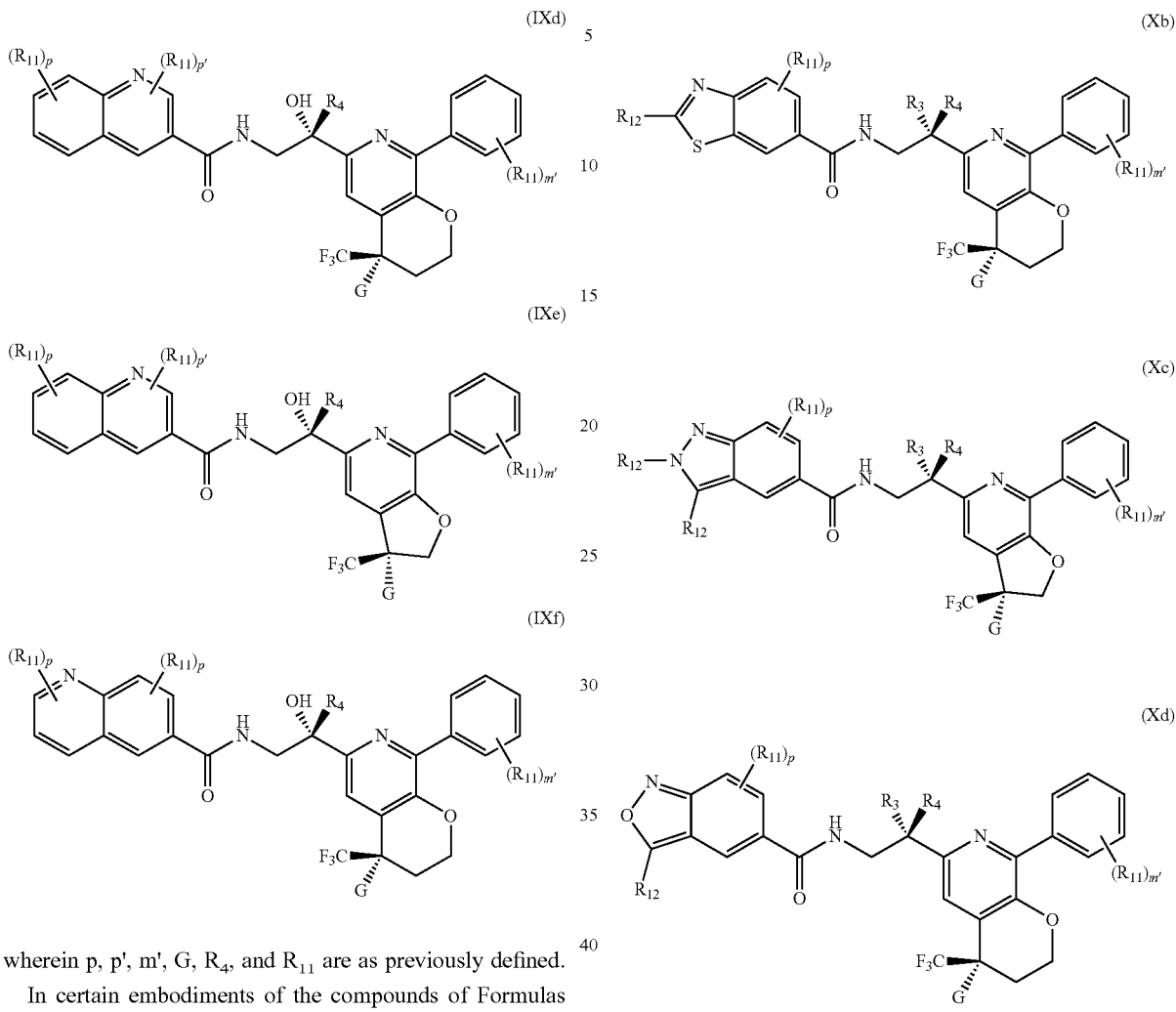

wherein p, p', m', G, R$_4$, and R$_{11}$ are as previously defined.

In certain embodiments of the compounds of Formulas (VIIIb), (VIIIf), (IXb and (IXf), at least one p is not 0. In certain embodiments, one p is 0 and the other p is 1 or 2.

In certain embodiments of the compounds of Formulas (VIIId), (VIIIe), (IXd) and (IXe), at least one of p and p' is preferably not 0. In certain embodiments, one of p and p' is 0 and the other is 1 or 2.

In one embodiment of the present invention, the compound of Formula (I) is represented by one of Formulas (Xa) to (Xe), or a pharmaceutically acceptable salt, ester or prodrug thereof:

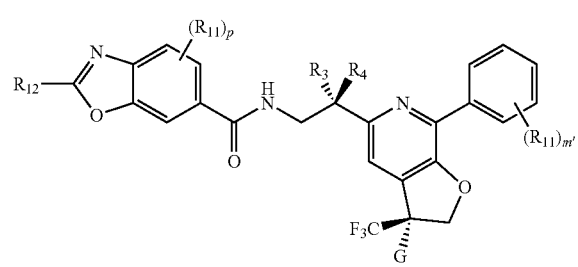

wherein each R$_{12}$ is independently hydrogen, optionally substituted —C$_1$-C$_6$ alkyl, optionally substituted C$_1$-C$_6$ alkoxyl, optionally substituted —C$_3$-C$_6$ cycloalkyl, halo, —CN, or —NR$_7$R$_8$; and p, m', G, R$_3$, R$_4$, R$_7$, R$_8$, and R$_{11}$ are as previously defined.

In one embodiment of the present invention, the compound of Formula (I) is represented by one of Formulas (Xf) to (Xm), or a pharmaceutically acceptable salt, ester or prodrug thereof:

(Xf)
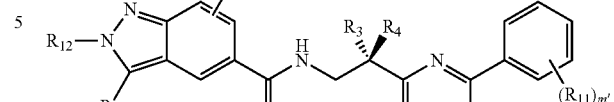
(Xk)
(Xg)
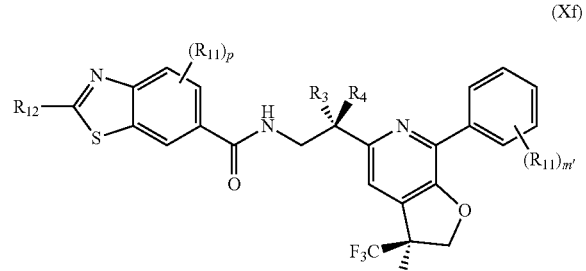
(Xm)
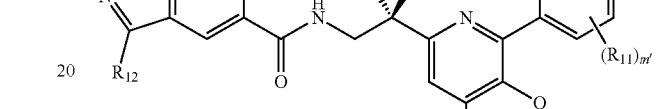
wherein p, m', G, $R_3$, $R_4$, $R_{11}$ and $R_{12}$ are as previously defined.
In certain embodiments, the compound of Formula (I) is represented by one of Formulas (XIa) to (XIe), or a pharmaceutically acceptable salt, ester or prodrug thereof:
(Xh)
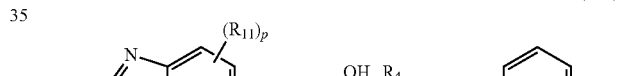
(XIa)
(Xi)
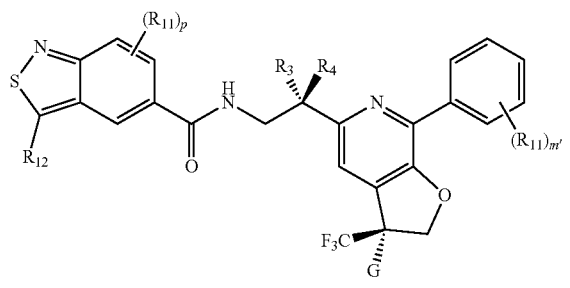
(XIb)
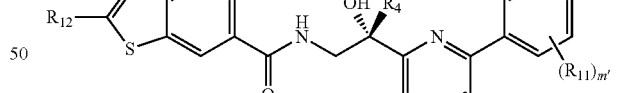
(Xj)
(XIc)
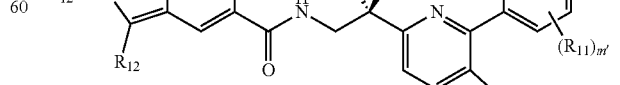

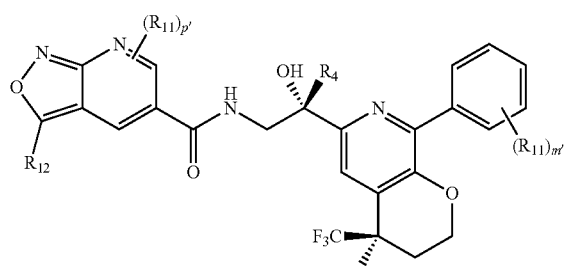
(XId)

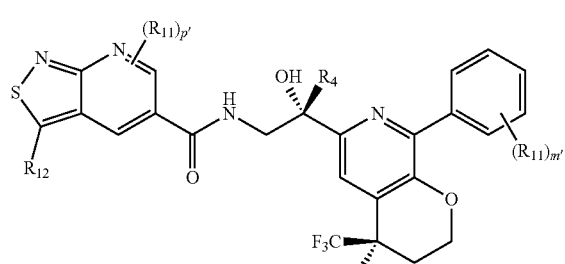
(XIe)

wherein p, p', m', G, R₄, R₁₁, and R₁₂ are as previously defined.

In one embodiment of the present invention, the compound of Formula (I) is represented by one of Formulas (XIf) to (XIm), or a pharmaceutically acceptable salt, ester or prodrug thereof:

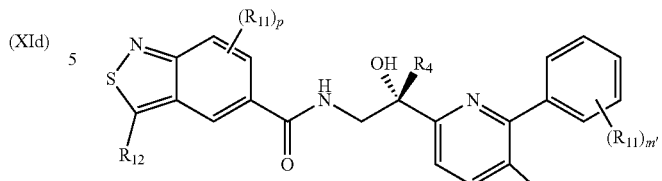
(XIf)

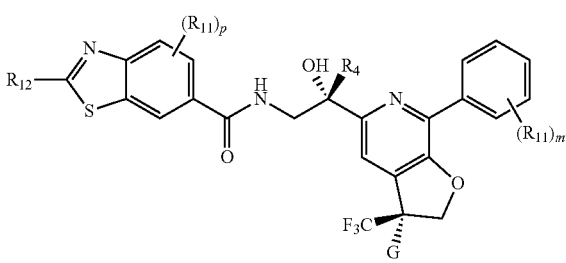
(XIg)

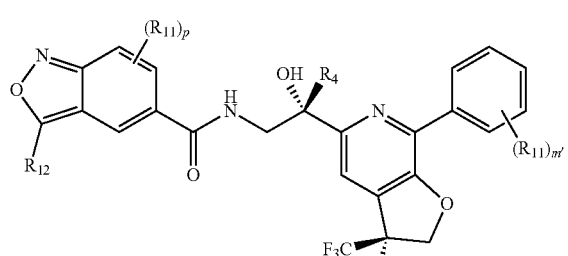

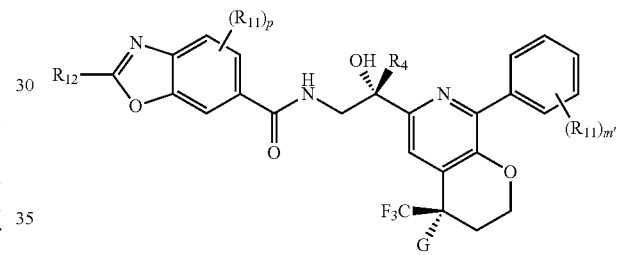
(XIh), (XIi), (XIj)

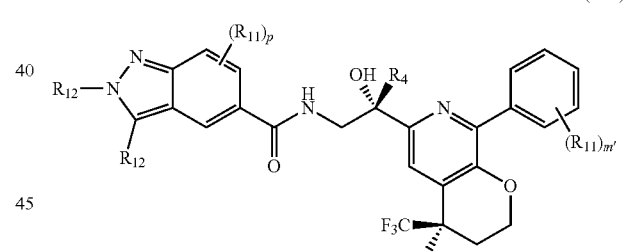
(XIk), (XIm)

wherein p, m', G, R₄, R₁₁ and R₁₂ are as previously defined. Each R₁₂ can be the same or different.

In one embodiment of the present invention, the compound of Formula (I) is represented by one of Formulas (XIIa) to (XIIb), or a pharmaceutically acceptable salt, ester or prodrug thereof:

(XIIa)

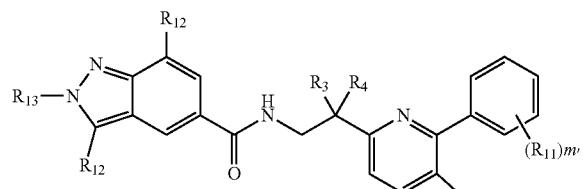

(XIIb)

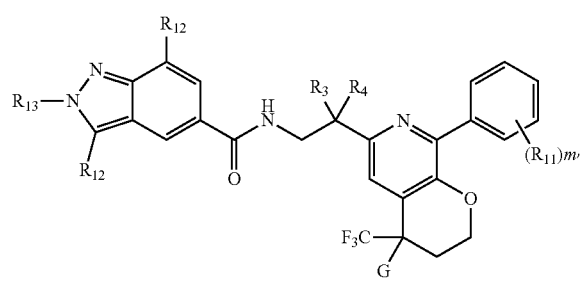

wherein each R₁₃ is independently hydrogen, halo, optionally substituted —C₁-C₆ alkyl, optionally substituted —C₃-C₆ cycloalkyl, or optionally substituted 3-6-membered heterocyclic; m', G, R₃, R₄, R₁₁, and R₁₂ are as previously defined. Preferably m' is 1, or 2.

In one embodiment of the present invention, the compound of Formula (I) is represented by one of Formulas (XIIIa) to (XIIIb), or a pharmaceutically acceptable salt, ester or prodrug thereof:

(XIIIa)

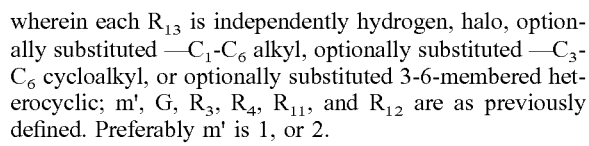

(XIIIb)

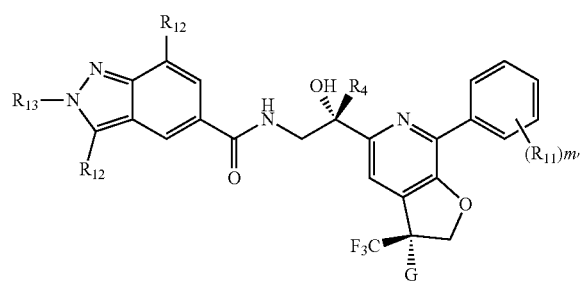

wherein m', G, R₄, R₁₁, R₁₂, and R₁₃ are as previously defined. Preferably m' is 1, or 2.

In one embodiment of the present invention, the compound of Formula (I) is represented by one of Formulas (XIVa) to (XIVb), or a pharmaceutically acceptable salt, ester or prodrug thereof:

(XIVa)

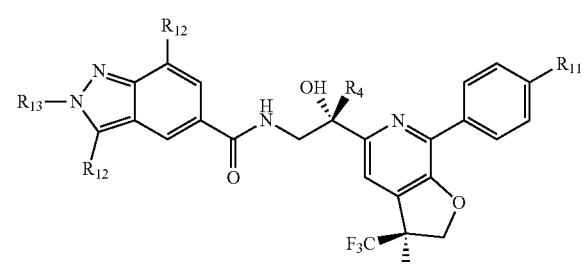

(XIVb)

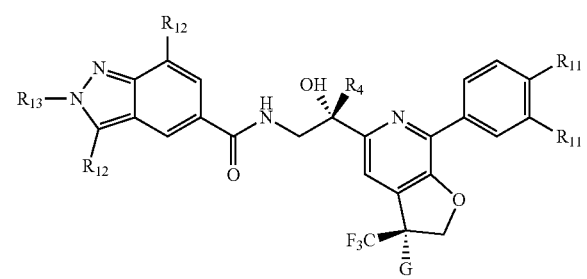

wherein G, R₄, R₁₁, R₁₂, and R₁₃ are as previously defined.

In one embodiment of the present invention, the compound of Formula (I) is represented by one of Formulas (Xc-1), (Xi-1), (Xk-1), and (Xn-1), or a pharmaceutically acceptable salt, ester or prodrug thereof:

(Xc-1)

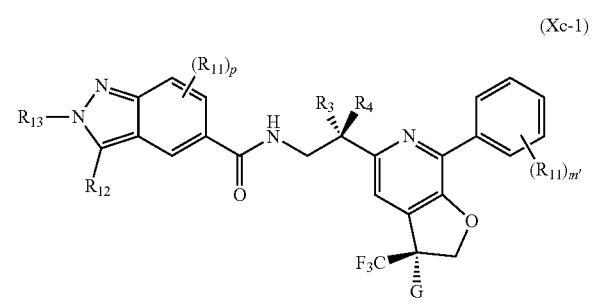

(Xk-1)

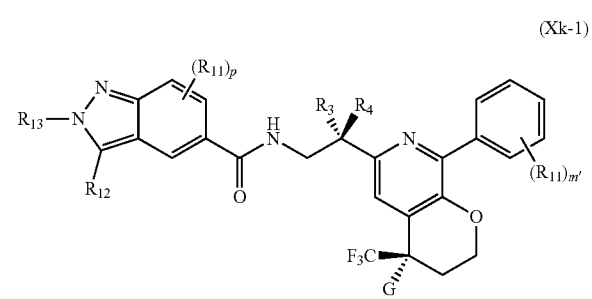

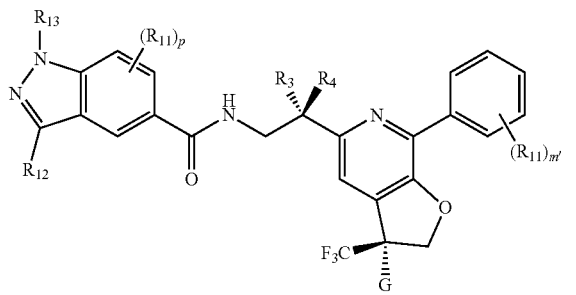

(Xi-1)

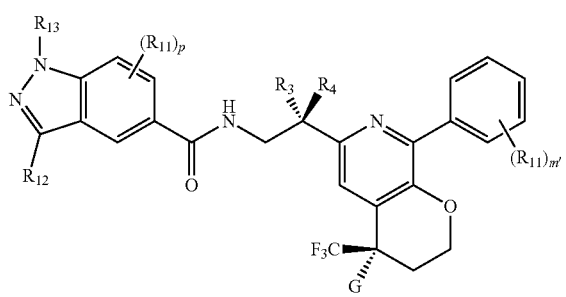

(Xm-1)

wherein m', p, G, $R_3$, $R_4$, $R_{11}$, $R_{12}$, and $R_{13}$ are as previously defined. Preferably m' is 1, or 2.

It will be appreciated that the description of the present invention herein should be construed in congruity with the laws and principles of chemical bonding. In some instances, it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In certain embodiments, the present invention provides a method for the prevention or treatment of RSV/HMPV infection and for treating RSV/HMPV infection in a subject in need thereof. The method comprises administering to the subject a therapeutically effective amount of a compound of Formula (I) or a pharmaceutically acceptable salt thereof. In certain embodiments, the subject is a human and the RSV is HRSV.

The present invention also provides the use of a compound of Formula (I) or a pharmaceutically acceptable salt thereof in the preparation of a medicament for the prevention or treatment of RSV/HMPV.

Thus, in one embodiment, a compound of formula (I), or pharmaceutically acceptable salt thereof, is combined with a steroid anti-inflammatory compound, for example budesonide or fluticasone. In a preferred embodiment, the steroid is administered in low doses to minimize immuno-suppressant effects. In another embodiment a compound of formula (I), or a pharmaceutically acceptable salt thereof, is combined with a non-steroid anti-inflammatory compound, for example leukotriene antagonists such as Singulair (Merck) or Accolate (Astra Zeneca), phosphodiesterase 4 inhibitors such as roflumilast (Altana), TNF alpha inhibitors such as Enbrel (Amgen), Remicade (Centocor), Humira (Abbott) or CDP870 (Celltech) or NSAIDS. In a further embodiment, a compound of formula (I) is combined with interleukin 8 or interleukin 9 inhibitors. The present invention thus also relates to a product containing a compound of formula (I), or a pharmaceutically acceptable salt thereof, and an anti-inflammatory compound for simultaneous, separate or sequential use in the treatment of RSV.

The present invention also relates to a combination of a compound of formula (I), or a pharmaceutically acceptable salt thereof, with an anti-influenza compound and the use of such a combination in the treatment of concomitant RSV/HMPV and influenza infections. The present invention thus also relates to a product containing a compound of formula (I), or a pharmaceutically acceptable salt thereof, and an anti-influenza compound for simultaneous, separate or sequential use in the treatment of concomitant RSV/HMPV and influenza infections. The compounds of the invention may be administered in a variety of dosage forms. Thus, they can be administered orally, for example as tablets, troches, lozenges, aqueous or oily suspensions, dispersible powders or granules. The compounds of the invention may also be administered parenterally, whether subcutaneously, intravenously, intramuscularly, intrasternally, transdermally or by infusion techniques. The compounds may also be administered as suppositories.

In an embodiment, the compounds of the invention are administered by intranasal or intrabronchial administration. The present invention also provides an inhaler or nebulizer containing a medicament which comprises (a) a derivative of the formula (I), as defined above, or a pharmaceutically acceptable salt thereof, and (b) a pharmaceutically acceptable carrier or diluent.

The present invention also provides a pharmaceutical composition containing such a benzodiazepine derivative, or a pharmaceutically acceptable salt thereof, and a pharmaceutically acceptable carrier or diluent.

The compounds of the invention are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, nontoxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The present invention also relates to the novel compounds, as defined above; or a pharmaceutically acceptable salt thereof, for use in a method of treating the human or animal body. The present invention also relates to a pharmaceutical composition comprising a novel compound as defined above and a pharmaceutically acceptable diluent or carrier. Preferably, the pharmaceutical composition comprises a pharmaceutically acceptable salt of a novel compound as defined above. A pharmaceutically acceptable salt is as defined above. The novel compounds of the invention are typically administered in the manner defined above and the compounds are typically formulated for administration in the manner defined above.

Preferably, the pharmaceutical compositions comprise optically active isomers of the novel compounds of the invention. Thus, for example, preferred novel compounds of the invention containing only one chiral center include an R enantiomer in substantially pure form, an S enantiomer in substantially pure form and enantiomeric mixtures which contain an excess of the R enantiomer or an excess of the S enantiomer. It is particularly preferred that pharmaceutical contains a compound of the invention which is a substantially pure optical isomer. For the avoidance of doubt, the novel compounds of the invention can, if desired, be used in the form of solvates.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono-, bi-, or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono-, bi-, or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl", "$C_1$-$C_6$ alkyl", "$C_1$-$C_{10}$ alkyl", "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl", "$C_2$-$C_8$ alkenyl", "$C_2$-$C_4$ alkenyl", or "$C_3$-$C_6$ alkenyl", refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl", "$C_2$-$C_8$ alkynyl", "$C_2$-$C_4$ alkynyl", or "$C_3$-$C_6$ alkynyl", refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_2$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_2$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_2$-cycloalkyl, —CONH-aryl, —CONH-heteroaryl, —CONH— heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-C-alkynyl, —OCONH—$C_3$-$C_{12}$-cycloalkyl, —OCONH-aryl, —OCONH-heteroaryl, —OCONH-heterocycloalkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_2$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_2$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably $C_1$ and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; NH$_2$; C$_1$-C$_4$-alkylamino; di(C$_1$-C$_4$-alkyl)amino; and NO$_2$. It is understood that the aryls, heteroaryls, alkyls, and the like can be further substituted. In some cases, each substituent in a substituted moiety is additionally optionally substituted when possible with one or more groups, each group being independently selected from C$_1$-C$_4$-alkyl; —CF$_3$, —OCH$_3$, —OCF$_3$, —F, —Cl, —Br, —I, —OH, —NO$_2$, —CN, and —NH$_2$.

In certain embodiments, a substituted alkyl, alkenyl or alkoxy group is substituted with one or more halogen atoms, preferably fluorine atoms. Such substituted alkyl groups include fluoromethyl, difluoromethyl and trifluoromethyl. Such substituted alkoxy groups include fluoromethoxy, difluoromethoxy and trifluoromethoxy.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but are not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T.H. Greene and P.G.M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, iso-propoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-*2, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T.H. Greene and P.G.M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P.G.M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Pharmaceutically acceptable salts can also be prepared by deprotonation of the parent compound with a suitable base, thereby forming the anionic conjugate base of the parent compound. In such salts the counter ion is a cation. Suitable cations include ammonium and metal cations, such as alkali metal cations, including $Li^+$, $Na^+$, $K^+$ and $Cs^+$, and alkaline earth metal cations, such as $Mg^{2+}$ and $Ca^{2+}$.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

In certain embodiments, the invention provides pharmaceutically acceptable prodrugs of the compounds disclosed herein. The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed.). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities. In certain embodiments, a compound of the invention can incorporate two or more groups that are metabolically removed in vivo to yield the active parent compound.

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or nonstoichiometric amounts of solvent. Some compounds have a tendency to trap a fixed molar ratio of solvent molecules in the crystalline solid state, thus forming a solvate. If the solvent is water, the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired bridged macrocyclic products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T.W. Greene and P.G.M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ACN for acetonitrile;
AD-mix-β for (9S)-(9"S)-9,9"-[1,4-Phthalazinediylbis(oxy)]bis[10,11-dihydro-6'-methoxycinchonan];
Bn for benzyl;
BOP for (Benzotriazol-1-yloxy)tris(dimethylamino)phosphonium hexafluorophosphate;
BzCl for benzoyl chloride;
Cbz for benzyloxycarbonyl;
CDI for carbonyldiimidazole;
DAST for diethylaminosulfur trifluoride;
DBU for 1,8-Diazabicycloundec-7-ene;
DCE for dichloroethane;
DCM for dichloromethane;
Dess-Martin periodinane for 1,1,1-tris(acetyloxy)-1,1-dihydro-1,2-benziodoxol-3-(1H)-one
DIAD for diisopropyl azodicarboxylate;
DIBAL-H for diisobutylaluminum hydride;
DMAP for N,N-dimethylaminopyridine;
DME for 1,2-dimethoxyethane;
DMF for N,N-dimethyl formamide;
DMSO for dimethylsulfoxide;

DPPA for diphenylphosphoryl azide or diphenyl phosphorylazidate;
dppf for 1,1'-Bis(diphenylphosphino)ferrocene;
EDCI or EDC for 1-(3-diethylaminopropyl)-3-ethylcarbodiimide hydrochloride;
EtOAc for ethyl acetate;
Ghosez's reagent for 1-Chloro-N,N,2-trimethyl-1-propenylamine;
HATU for O (7-Azabenzotriazole-1-yl)-N,N,N',N'-tetramethyluronium hexafluorophosphate;
HCl for hydrochloric acid;
Hrs for hours;
Hunig's base for diisopropylethylamine;
LDA for Lithium diisopropylamine;
MTBE for methyl tert-butyl ether;
PyBOP for (Benzotriazol-1-yloxy)tripyrrolidinophosphonium hexafluorophosphate;
Pd—C for palladium carbon;
Ph for phenyl;
rt for room temperature;
RT for reverse transcription;
RT-PCR for reverse transcription-polymerase chain reaction;
TBME for tert-butyl methyl ether;
TEA for triethylamine;
Tf$_2$O for trifluoromethanesulfonic anhydride;
TFA for trifluoroacetic acid;
THF for tetrahydrofuran;
(TMS)$_2$NH for hexamethyldisilazane;
TBS for tert-Butyldimethylsilyl;
TBDPS for tert-Butyldiphenylsilyl;
TMS for trimethylsilyl;
TPAP tetrapropylammonium perruthenate;
TPP or PPh$_3$ for triphenylphosphine;
Ts or tosyl for p-CH$_3$C$_6$H$_4$SO$_2$—;
tBOC or Boc for tert-butyloxy carbonyl; and
Xantphos for 4,5-Bis-diphenylphosphanyl-9,9-dimethyl-9H-xanthene.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1 illustrates methods to prepare a compound of Formula XII from an amine compound 1a or 1b, wherein A, R$_4$, E and G are as previously defined. Rx is an alkyl or aryl group, such as but not limited to, tBu and Ph. L$_2$ is a leaving group, such as, but not limited to —Cl, —OSu, -imidazole, or —OC$_6$F$_5$. Coupling reaction of 1a with an acid compound 2a in the presence of carboxylic acid activating reagent such as, but not limited to HATU, DIAD and organic base such as DIPEA affords compound 3a. Alternatively, compound 1a reacts with an activated carboxylic acid derivative 2b, under standard amide formation conditions to afford compound 3a. Cleavage of the sulfinamide group with acids such as, but not limited to, HCl or TFA, forms compound 3b. Alternatively, amide formation between compound 1b and an acid compound 2a, or an activated carboxylic acid derivative 2b provides compound 3b directly. Compound 3b is converted to a compound of Formula XII through appropriate functional group transformations.

Scheme 1

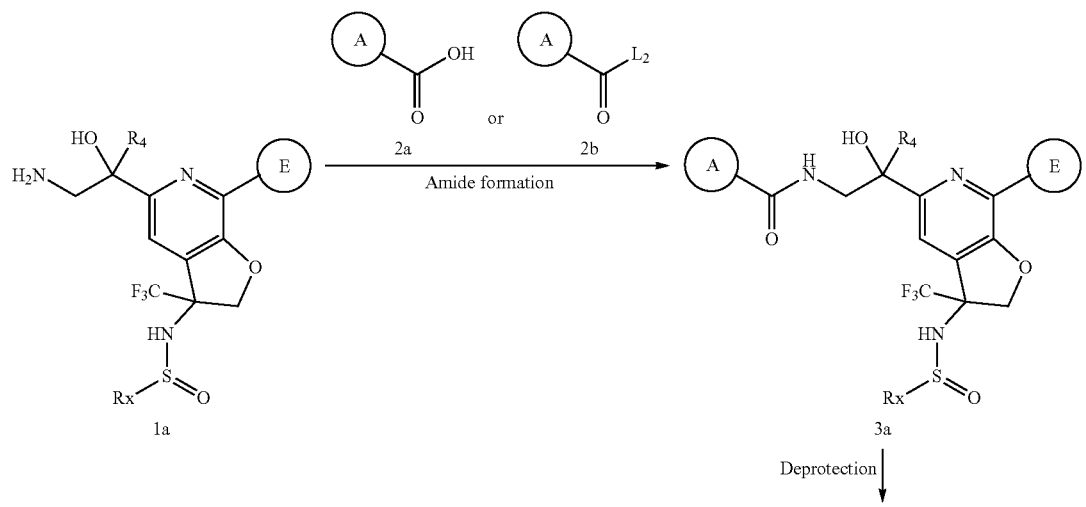

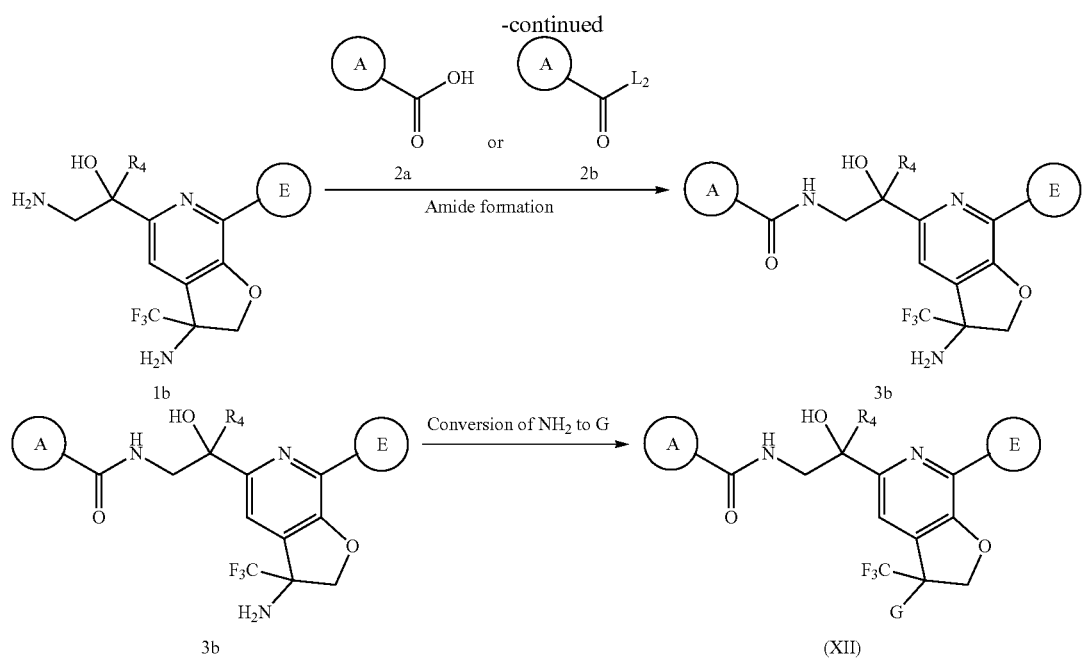

Scheme 2 demonstrates the preparation of compound 1a and 1b from compound 4. A metal catalyzed coupling reaction of compound 4 with compound 5, wherein M includes, nor limited to boronic acid, boronic ester, SnMe$_3$, or SnBu$_3$, provides olefin compound 6. Compound 6 is then converted to compound 8 either through a dihydroxylation/epoxide formation sequence or directly through epoxidation. Using appropriate chiral dihydroxylation reagents and/or ligands, compound 7 can be prepared in a stereoselective or stereospecific fashion. Similarly, the epoxidation of compound 6 can be carried out asymmetrically with appropriate chiral epoxidation reagents and/or ligands to form chiral epoxide 8. Reaction of ammonia with compound 8 affords compound 1a. Alternatively, the diol compound 7 is converted to compound 9, whereas L is a leaving group, such as, but not limited to Cl, Br, I, OMs, or OTs. Displacement of L of compound 9 with ammonia provides compound 1a, which is converted to compound 1b by removal of the sulfinamide group under acidic conditions.

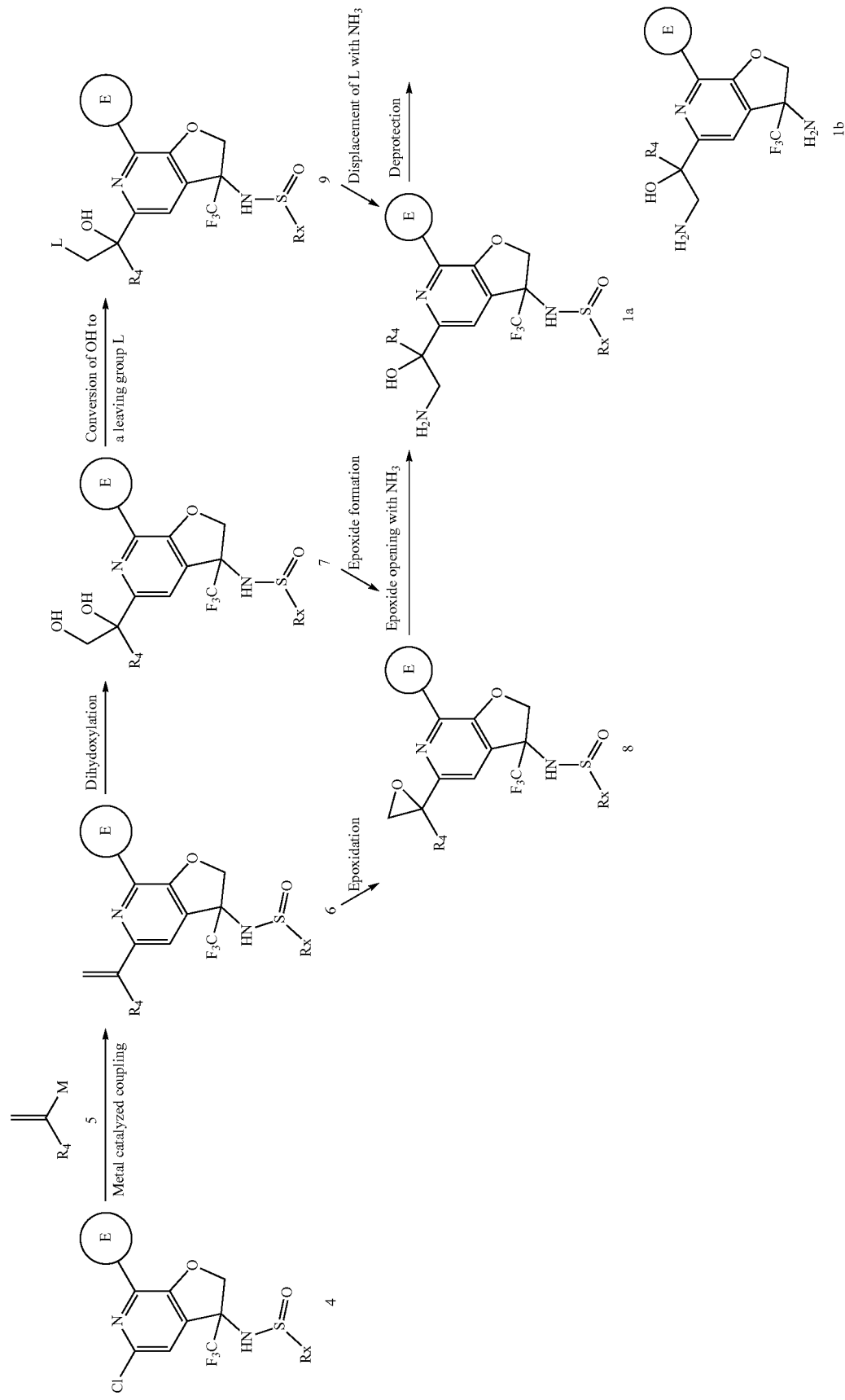
Scheme 2

Scheme 3 shows the preparation of compound 4 from compound 13 and 15, wherein E, M and Rx are as previously defined. Protection of the OH group of compound 10 gives compound 11, wherein PG$_1$ is an appropriate HO protecting group, such as, but not limited to MOM, MEM, SEM, TES, TBS, or TBDPS. Compound 11 undergoes a standard meta-catalyzed arylation reaction with compound 12 to give compound 13. Ketimine compound 16 is prepared by reacting CF$_3$ ketone compound 14 with sulfinamide compound 15 in the presence of Ti(OEt)$_4$ upon heating. Compound 13 is then treated with a strong base, such as, but not limited to nBuLi, LDA, or LHMDS, to form an anion, which is quenched with ketimine compound 16 at a lower temperature, such as at or below 60° C. to provide compound 17 as a mixture of diastereomers. Under certain conditions with appropriate base, solvent and reaction temperature, compound 17 can be prepared stereoselectively from enantiomerically pure compound 16. Ozonolysis of olefin compound 17 followed by hydride reduction affords alcohol compound 18, which is then converted to diol compound 19 upon treatment with a weak acid, such as but not limited to citric acid. An intramolecular cyclization of compound 19 under Mitsunobu reaction conditions affords compound 4.

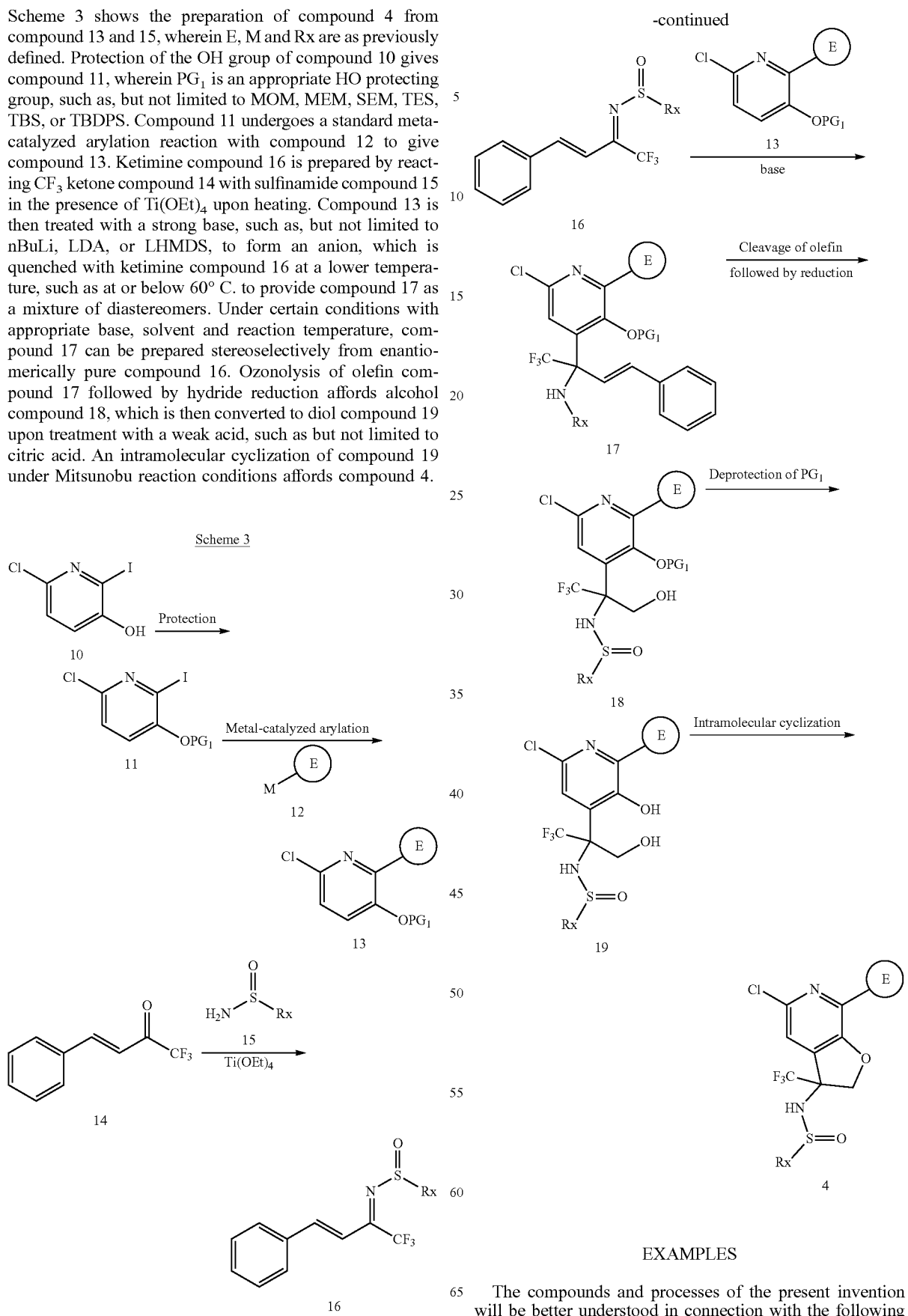

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1: (R)—N—((R)-5-((S)-3-amino-1,1,1-trifluoro-2-hydroxypropan-2-yl)-7-(4-fluorophenyl)-3-(trifluoromethyl)-2,3-dihydrofuro[2,3-c]pyridin-3-yl)-2-methylpropane-2-sulfinamide Example 1

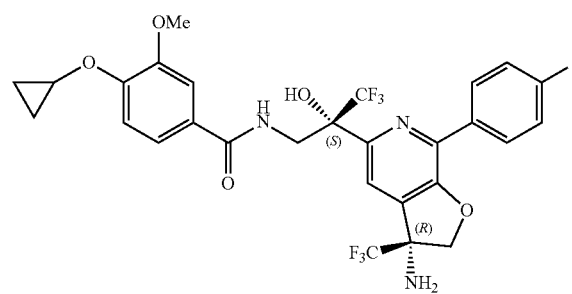

Step 1~2: Synthesis of 6-chloro-2-(4-fluorophenyl)-3-(methoxymethoxy)pyridine (compound 1-3

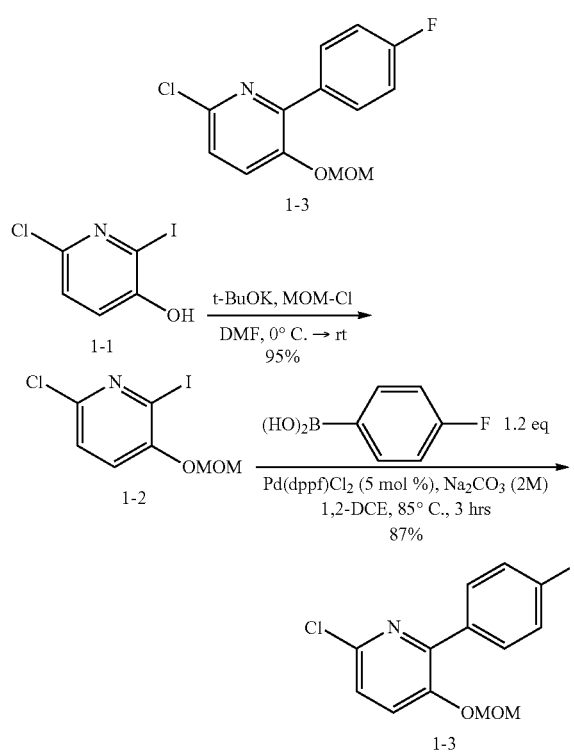

Step 1: Potassium tert-butoxide (23.09 g, 206 mmol) was added portion-wise to a solution of 6-chloro-2-iodopyridin-3-ol (1-1) (43.8 g, 171 mmol) in DMF (214 mL) at 0° C. The reaction was stirred for 20 min at 0° C. MOM-Cl (18.2 mL, 19.3 g, 240 mmol) was added dropwise, and the reaction was stirred for 1 h at 0° C., then for 2 h at rt. The reaction was quenched with H$_2$O (400 mL) and diluted with MTBE (400 mL). The layers were separated, and the aqueous layer was extracted with MTBE (1×200 mL). The combined organic layers were washed with brine (2×500 mL), dried (MgSO$_4$), and concentrated under reduced pressure to provide 6-chloro-2-iodo-3-(methoxymethoxy)pyridine (1-2) (49.3 g, 165 mmol, 96% yield) as an orange oil that solidified upon standing: $^1$H NMR (400 MHz, Chloroform-d) δ 7.26 (d, J=8.5 Hz, 1H), 7.19 (d, J=8.5 Hz, 1H), 5.24 (s, 2H), 3.51 (s, 3H); LC-MS, ES$^+$ (m/z): 299.83 [M+H]$^+$.

Step 2: A mixture of 6-chloro-2-iodo-3-(methoxymethoxy)pyridine (1-2) (27.8 g, 93 mmol), (4-fluorophenyl)boronic acid (15.59 g, 111 mmol), Na$_2$CO$_3$ (93 mL, 186 mmol), and PdCl$_2$(dppf) (3.40 g, 4.64 mmol) in DCE (928 mL) was sparged with N$_2$ for 20 minutes. The reaction was then heated at 85° C. under N$_2$ for ~3 hrs and monitored by LC-MS. After cooling to rt, the reaction was quenched with H$_2$O and diluted with CH$_2$Cl$_2$. Layers were separated and the aqueous layer was extracted with CH$_2$Cl$_2$ (2×). Combined organic layers were dried (Na$_2$SO$_4$) and concentrated to give a brown solid. Purified by SiO$_2$ column chromatography with 0 to 15% EtOAc/cyclohexane provided compound 1-3 (21.5 g, 80 mmol, 87% yield) as a white solid. $^1$H NMR (400 MHz, Chloroform-d) δ 7.98-7.91 (m, 2H), 7.54 (d, J=8.7 Hz, 1H), 7.21 (dd, J=8.7, 0.6 Hz, 1H), 7.17-7.08 (m, 2H), 5.19 (s, 2H), 3.45 (d, J=0.6 Hz, 3H); LC-MS, ES$^+$ (m/z): 268.02 [M+H]$^+$.

Step 3~5: Synthesis of (R)-2-methyl-N-((2E Z,3)-1,1,1-trifluoro-4-phenylbut-3-en-2-ylidene)propane-2-sulfinamide (compound 1-7)

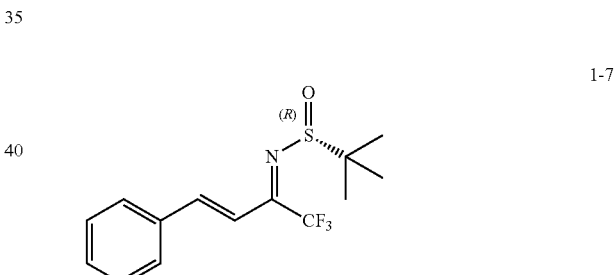

Step 3: Synthesis of (D)-1,1,1-trifluoro-4-phenyl-but-3-en-2-ol (compound 1-5)

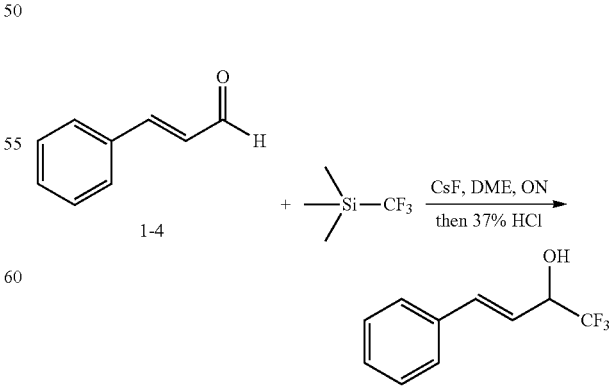

To a solution of trans-cinnamaldehyde (1-4) (13 mL, 103 mmol) in 1,2-dimethoxyethane (250 mL) was added trimethyl(trifluoromethyl)silane (2M in THF, 54.2 mL, 108 mmol), followed by cesium fluoride (124 mg, 0.816 mmol). The mixture was stirred at rt for 16 hrs. 37% hydrochloric acid (8.48 mL, 103 mmol) and water (8.37 mL, 465 mmol) were then added. The mixture was stirred for 20 min and partitioned in MTBE and brine. The organic layer was separated, dried over MgSO$_4$ and concentrated in vacuo. The crude product 1-5 (24 g, 119 mmol, 115% yield) as a pale yellow oil was used directly in the next step. $^1$H NMR (400 MHz, DMSO-d$_6$) δ 7.52-7.44 (m, 2H), 7.37-7.33 (m, 2H), 7.31-7.24 (m, 1H), 6.85 (d, J=15.8 Hz, 1H), 6.54 (d, J=6.0 Hz, 1H), 6.25 (dd, J=15.9, 6.4 Hz, 1H), 4.69 (p, J=6.7 Hz, 1H), 3.41 (s, 1H).

Step 4: Synthesis of (E)-1,1,1-trifluoro-4-phenylbut-3-en-2-one (compound 1-6)

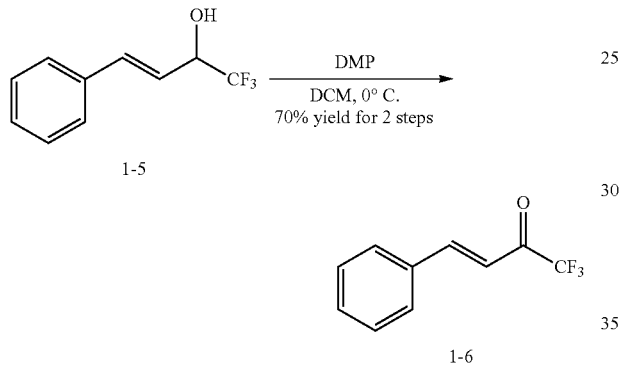

To a solution of compound 1-5 (crude from last step ~24 g, 119 mmol) in DCM (400 mL) at 0° C. was added Dess-Martin periodinane (50.3 g, 119 mmol). The resulting mixture was stirred at 0° C. for 2 hrs, diluted with DCM, and filtered through a silica gel plug (60 g). The filtrate was concentrated in vacuo. Purification of the residue on silica gel with 0-20% EtOAc in hexane provided the desired product 1-6 as a pale-yellow oil (16.6 g, 70% yield from compound 1-4 in 2 steps). $^1$H NMR (400 MHz, DMSO-d$_6$) δ 7.89 (d, J=16.0 Hz, 1H), 7.82-7.72 (m, 2H), 7.44-7.30 (m, 3H), 7.25 (d, J=16.0 Hz, 1H).

Step 5: Synthesis of (R)-2-methyl-N-((2Z,3E)-1,1,1-trifluoro-4-phenylbut-3-en-2-ylidene)propane-2-sulfinamide (compound 1-7)

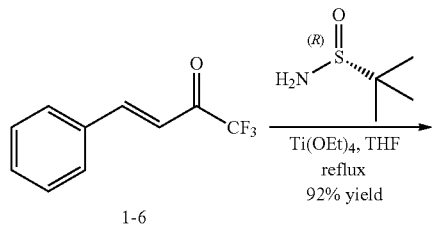

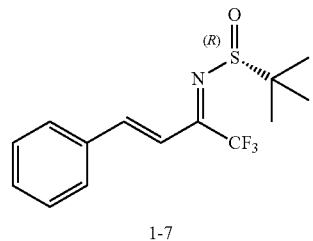

To a solution of (E)-1,1,1-trifluoro-4-phenylbut-3-en-2-one (1-6) (2 g, 9.99 mmol) in anhydrous THF (25 mL) at rt under N$_2$ was added tetraethoxytitanium (5.24 mL, 24.98 mmol), followed by (R)-2-methylpropane-2-sulfinamide (1.453 g, 11.99 mmol). The mixture was heated at 76° C. for 4 hrs, cooled to rt, diluted with ethyl acetate, and quenched with water (60 mL). The resulting suspension was filtered through celite and the filter cake was rinsed with ethyl acetate (3×). The combined filtrates were washed with brine, dried over MgSO$_4$, and concentrated in vacuo. Purification of the residue on silica gel with 0-20% EtOAc/hexane provided the desired compound 1-7 (2.8 g, 92% yield) as a yellow oil. $^1$H NMR (400 MHz, Chloroform-d) δ 8.08 (d, J=17.0 Hz, 1H), 7.63-7.49 (m, 2H), 7.43-7.36 (m, 3H), 7.32 (d, J=17.0 Hz, 1H), 1.35 (s, 9H).

Step 6~9: Synthesis of (R)—N—((R)-5-chloro-7-(4-fluorophenyl)-3-(trifluoromethyl)-2,3-dihydrofuro[2,3-c]pyridin-3-yl)-2-methylpropane-2-sulfinamide (compound 1-11)

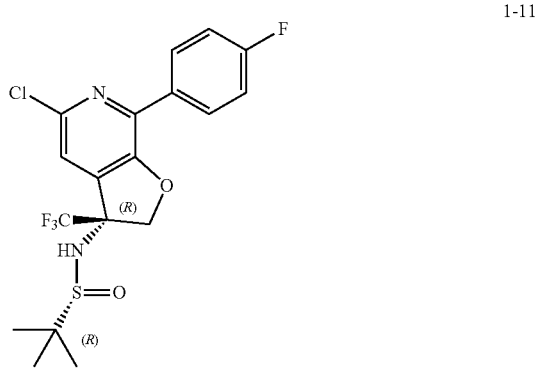

Step 6: Synthesis of Compound 1-8 and 1-8a

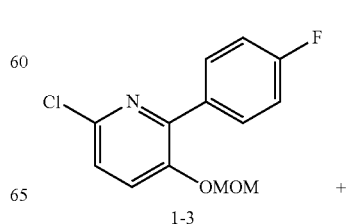 +

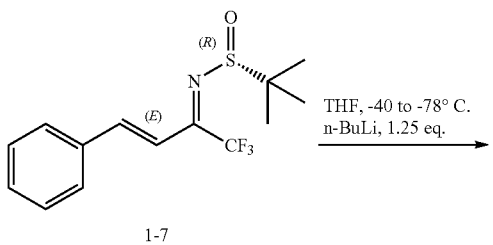

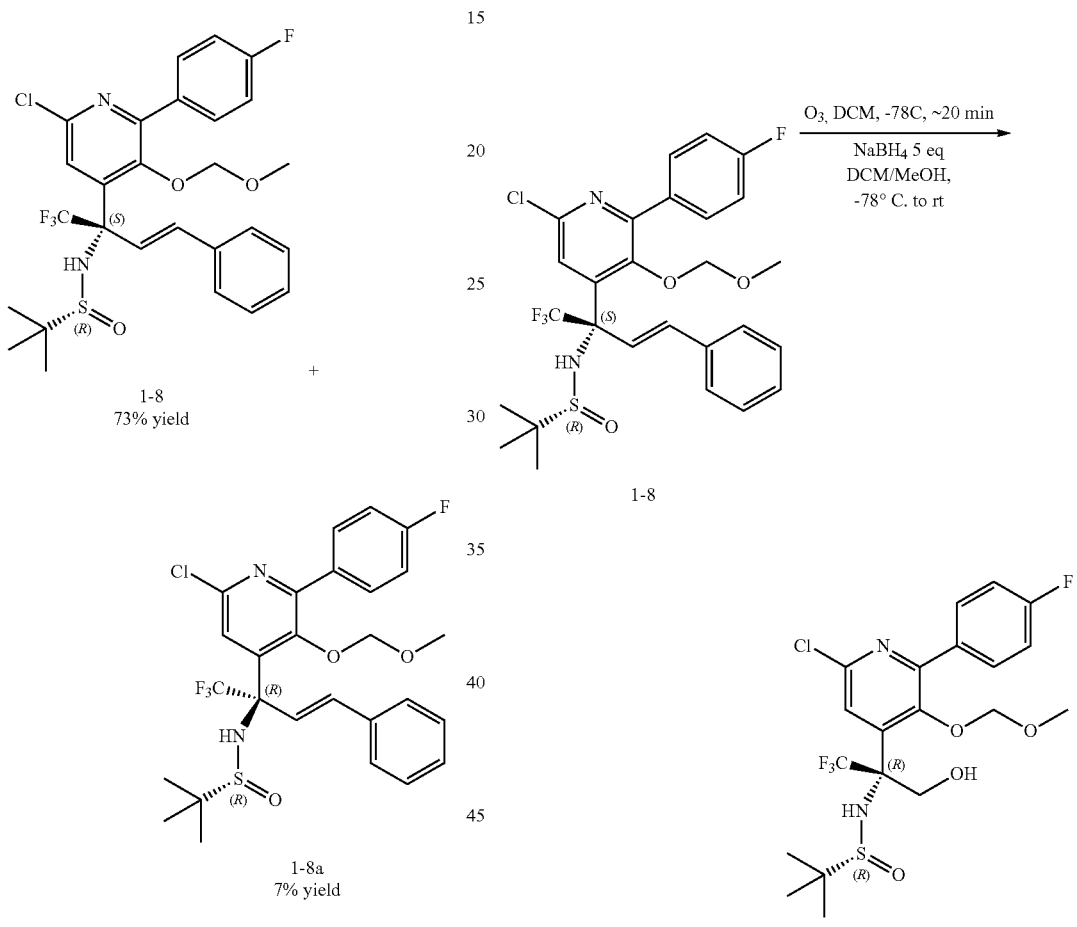

3H), 7.35 (s, 1H), 7.23-7.11 (m, 3H), 6.98 (d, J=16.8 Hz, 1H), 6.57 (d, J=16.8 Hz, 1H), 4.73 (d, J=3.8 Hz, 1H), 4.64 (d, J=3.8 Hz, 1H), 3.26 (s, 3H), 1.32 (s, 9H).

Analytical data for the minor isomer 1-8a: LC-MS, ES$^+$ (m/z): 571.1 [M+H]$^+$. $^1$H NMR (400 MHz, Chloroform-d) δ 7.80-7.72 (m, 2H), 7.50-7.31 (m, 6H), 7.12 (t, J=8.7 Hz, 2H), 6.74 (d, J=16.3 Hz, 1H), 6.34 (d, J=16.3 Hz, 1H), 4.80 (d, J=4.4 Hz, 1H), 4.47 (d, J=4.4 Hz, 1H), 3.29 (s, 3H), 1.26 (s, 9H).

Step 7: Synthesis of Compound 1-9

To a solution of compound 1-3 (5.27 g, 19.67 mmol) in anhydrous THF (76 mL) at −78° C. under N$_2$ was added n-butyllithium (2.5 M in hexanes, 7.57 mL, 18.91 mmol) dropwise. The resulting solution was stirred at −78° C. for ~30 min, and then at −40° C. for 60 min. After recooling to −78° C., a solution of compound 7 (4.59 g, 15.13 mmol) in anhydrous diethyl ether (30 mL) was added dropwise. The resulting mixture was stirred at −78° C. for 1 h, quenched with sat. NH$_4$Cl, and extracted with EtOAc (2×). The combined organics were washed with water, brine, dried over Na$_2$SO$_4$ and concentrated in vacuo. Purification of the residue on silica gel with 0-35% EtOAc/cyclohexane provided the minor diastereomer 1-8a (630 mg, 7% yield) and the major isomer 1-8 (6.3 g, 73% yield).

Analytical data for the major diastereomer 1-8: LC-MS, ES$^+$ (m/z): 571.1 [M+H]$^+$. $^1$H NMR (400 MHz, Chloroform-d) δ 7.87-7.77 (m, 2H), 7.59-7.51 (m, 2H), 7.44-7.36 (m, Compound 1-8 (6.3 g, 11.03 mmol) was dissolved in DCM (138 mL) and cooled to −78° C. The solution was treated with ozone until TLC and LC-MS showed complete consumption of the starting material (in about ~20 min), The excess ozone was removed with blowing O2 followed by N$_2$ through the solution. At −78° C., sodium borohydride (2.08 g, 55.2 mmol) was added followed by addition of MeOH (10 mL). The reaction was stirred at −78° C. for ~15 min and then at rt for 30 min. The mixture was then cooled to 0° C. and quenched with sat. NH$_4$Cl. The organic layer was separated and the aqueous layer was extracted with DCM (1×). The combined organic layers were washed with brine, dried over Na$_2$SO$_4$, and concentrated to provide the crude solid product 1-9 (~6.3 g crude) which was directly used in the next step. LC-MS, ES$^+$ (m/z): 499.3 [M+H]$^+$.

Step 8: Synthesis of Compound 1-10

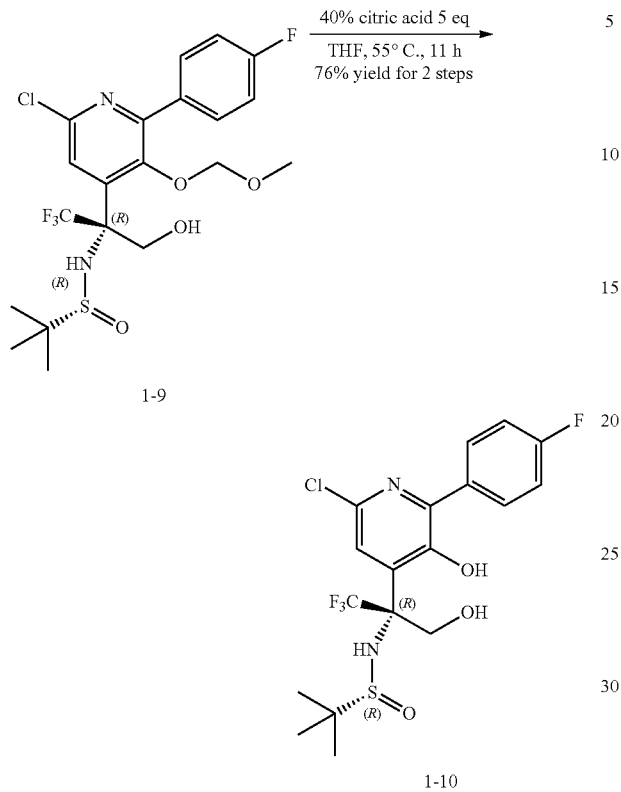

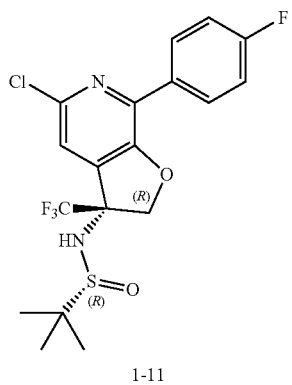

To a solution of compound 1-9 (6.3 g crude, ~11 mmol) in THF (18.31 mL) at rt was added a solution of citric acid monohydrate (11.54 g, 54.9 mmol) in water (18.3 mL). The mixture was heated at 53-55° C. and monitored by LC-MS. After heating for 12 hrs, the reaction was diluted with EtOAc (200 mL), washed with water, brine, dried over $Na_2SO_4$ and concentrated. Purification of the residue on silica gel with 0-45% EtOAc/cyclohexane provided the desired product 1-10 (3.84 g, 76% yield from compound 1-8 in 2 steps). LC-MS, ES$^+$ (m/z): 455.1 [M+H]$^+$; $^1$H NMR (400 MHz, Chloroform-d) δ 8.55 (brs, 1H), 7.92-7.83 (m, 2H), 7.29 (s, 1H), 7.19-7.09 (m, 2H), 5.12 (s, 1H), 4.63 (d, J=13.3 Hz, 1H), 4.38 (d, J=13.3 Hz, 1H), 1.33 (s, 9H).

Step 9: Synthesis of Compound 1-11

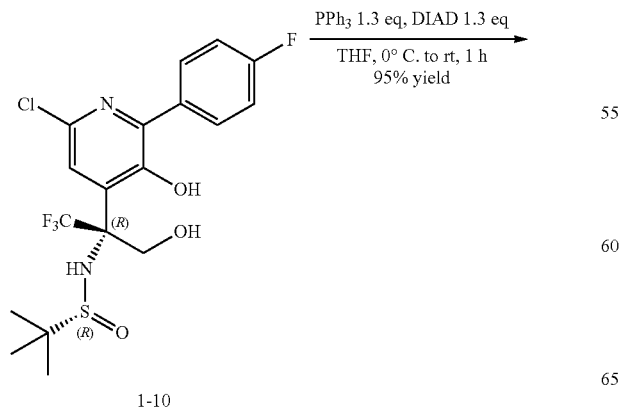

To a solution of compound 1-10 (3.84 g, 8.44 mmol) in dry THF (84 mL) at 0° C. was added triphenylphosphine (2.88 g, 10.97 mmol) followed by dropwise addition of DIAD (2.155 mL, 10.97 mmol). After stirring for 30 min at rt, the reaction mixture was concentrated. Purification of the residue on silica gel with 0-30% EtOAc/cyclohexane provided the desired product 1-11 (3.5 g, 95% yield). LC-MS, ES$^+$ (m/z): 437.2 [M+H]$^+$. $^1$H NMR (400 MHz, Chloroform-d) δ 8.26-8.20 (m, 2H), 7.31 (s, 1H), 7.21-7.08 (m, 2H), 5.13 (d, J=11.1 Hz, 1H), 4.97 (d, J=11.0 Hz, 1H), 3.81 (s, 1H), 1.25 (s, 9H).

Step 10: Synthesis of (R)—N—((R)-7-(4-fluorophenyl)-3-(trifluoromethyl)-5-(3,3,3-trifluoroprop-1-en-2-yl)-2,3-dihydrofuro[2,3-c]pyridin-3-yl)-2-methyl-propane-2-sulfinamide (compound 1-12)

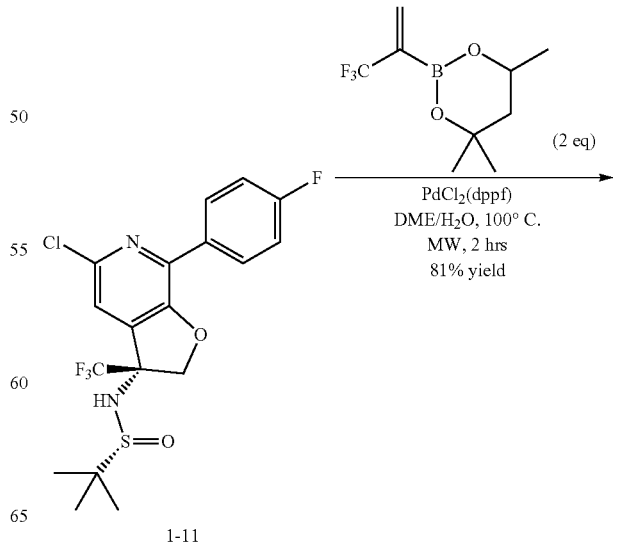

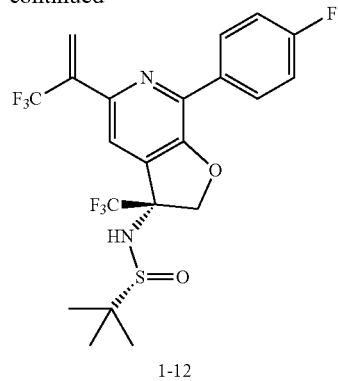

1-12

To a mixture of (R)—N—((R)-5-chloro-7-(4-fluorophenyl)-3-(trifluoromethyl)-2,3-dihydrofuro[2,3-c]pyridin-3-yl)-2-methylpropane-2-sulfinamide (1-11) (500 mg, 1.145 mmol) in 1,2-dimethoxyethane (6.1 mL) and water (1.5 mL) were added cesium carbonate (1.12 g, 3.43 mmol) and 4,4,6-trimethyl-2-(3,3,3-trifluoroprop-1-en-2-yl)-1,3,2-dioxaborinane (0.38 mL, 1.717 mmol). The mixture was degassed by budding through $N_2$ for 10 min. $PdCl_2$(dppf)-$CH_2Cl_2$ adduct (93 mg, 0.114 mmol) was added. The resulting mixture was stirred at 100° C. under microwave for 2 hrs. LC-MS indicated still some starting material remaining. Additional portions of 4,4,6-trimethyl-2-(3,3,3-trifluoroprop-1-en-2-yl)-1,3,2-dioxaborinane (0.13 mL, 0.57 mmol) and $PdCl_2$(dppf)-$CH_2Cl_2$ adduct (46 mg, 0.056 mmol) were added. The reaction mixture was heated at 100° C. under microwave for additional 1 h until LC-MS showed only very little starting material remained. The reaction mixture was then diluted with EtOAc, washed with water (2×), brine, dried over $Na_2SO_4$ and concentrated. Purification of the residue on silica gel with 0-30% EtOAc/cyclohexane provided the desired product 1-12 (460 mg, 81% yield). LC-MS (m/z): 497.5 [M+1]. $^1$H NMR (400 MHz, Chloroform-d) δ 8.36-8.25 (m, 2H), 7.49 (s, 1H), 7.22-7.07 (m, 2H), 6.54 (q, J=1.9 Hz, 1H), 6.14 (t, J=1.3 Hz, 1H), 5.13 (d, J=11.0 Hz, 1H), 4.99 (d, J=11.0 Hz, 1H), 3.85 (s, 1H), 1.24 (s, 9H).

Step 11: Synthesis of (R)—N—((R)-7-(4-fluorophenyl)-5-((R)-1,1,1-trifluoro-2,3-dihydroxypropan-2-yl)-3-(trifluoromethyl)-2,3-dihydrofuro[2,3-c]pyridin-3-yl)-2-methylpropane-2-sulfinamide (compound 1-13)

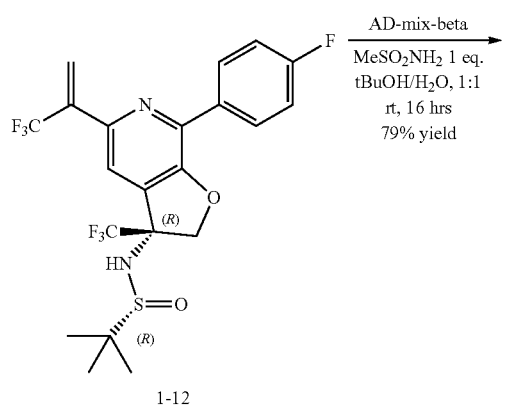

1-12

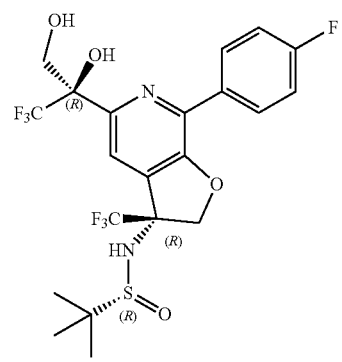

1-13

To a mixture of compound 1-12 (894 mg, 1.801 mmol) and methanesulfonamide (171 mg, 1.80 mmol) in t-BuOH (9.0 mL) and water (9.0 mL) was added AD-mix-beta (2.81 g). The mixture was stirred vigorously at rt for 16 hrs, until LC-MS showed complete consumption of sm. Work-up: the reaction mixture was quenched with sat. $Na_2SO_3$ (~50 mL), and extracted with EtOAc (3×). The combined organic layers were washed with water (2×), brine (2×), dried over $Na_2SO_4$ and concentrated in vacuo. Purification of the residue on silica gel with 0-50% EtOAc/cyclohexane provided the desired product 1-13 (750 mg, 79% yield). LC-MS (m/z): 531.5 [M+1]. $^1$H NMR (400 MHz, Chloroform-d) δ 8.22-8.18 (m, 2H), 7.58 (s, 1H), 7.22-7.11 (m, 2H), 5.07 (d, J=11.2 Hz, 1H), 4.94 (d, J=11.2 Hz, 1H), 4.29-4.21 (m, 2H), 4.15-4.02 (m, 2H), 1.27 (s, 9H).

Step 12: Synthesis of (R)—N—((R)-7-(4-fluorophenyl)-3-(trifluoromethyl)-5-((R)-2-(trifluoromethyl)oxiran-2-yl)-2,3-dihydrofuro[2,3-c]pyridin-3-yl)-2-methylpropane-2-sulfinamide (compound 1-14) and (R)-7-(4-fluorophenyl)-3-(trifluoromethyl)-5-((R)-2-(trifluoromethyl)oxiran-2-yl)-2,3-dihydrofuro[2,3-c]pyridin-3-amine (compound 1-15)

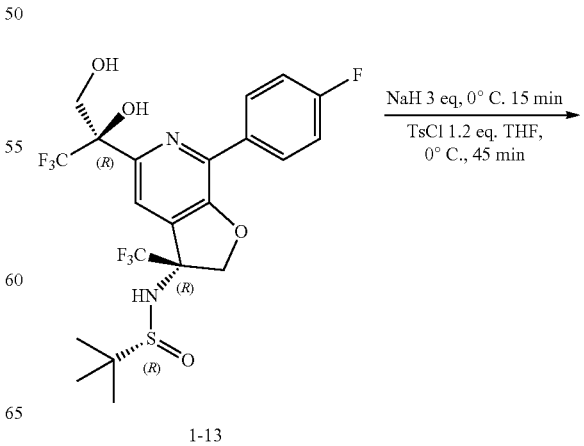

1-13

-continued

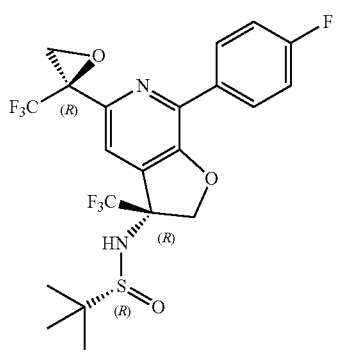

1-14
68% yield

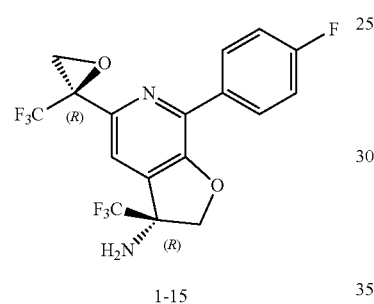

1-15
17% yield

To a solution of compound 1-13 (352 mg, 0.66 mmol) in anhydrous THE (22 mL) at 0° C. was added NaH, 60% dispersion in mineral oil (80 mg, 1.99 mmol). After stirring for ~15 min at 0° C., p-toluenesulfonyl chloride (152 mg, 0.796 mmol) was added. The reaction mixture was stirred at 0° C. for ~1 h. The reaction was quenched with water (22 mL) and concentrated under vacuum to remove most of THF. The resulting solution was extracted with EtOAc (2×30 mL). The combined organic layers were washed with brine, dried over $Na_2SO_4$, and concentrated. Purification of the residue on silica gel with 0-60% EtOAc/cyclohexane provided compound 1-15 (100 mg, 17% yield) and compound 1-14 (482 mg, 68% yield).

Analytical data for 1-15: LC-MS, $ES^+$ (m/z): 409.1.5 [M+1]. $^1$H NMR (400 MHz, Chloroform-d) δ 8.34-8.21 (m, 2H), 7.45 (s, 1H), 7.21-7.10 (m, 2H), 4.96 (d, J=10.5 Hz, 1H), 4.51 (dt, J=10.4, 1.5 Hz, 1H), 3.49 (d, J=5.2 Hz, 1H), 3.17 (dq, J=5.3, 1.5 Hz, 1H).

Analytical data for 1-14: LC-MS, $ES^+$ (m/z): 513.5 [M+1]. H-NMR $^1$H NMR (400 MHz, Chloroform-d) δ 8.34-8.24 (m, 2H), 7.48 (s, 1H), 7.21-7.12 (m, 2H), 5.18 (dd, J=11.1, 1.4 Hz, 1H), 5.00 (d, J=11.0 Hz, 1H), 3.79 (s, 1H), 3.49 (d, J=5.2 Hz, 1H), 3.16 (dd, J=5.3, 1.5 Hz, 1H), 1.24 (s, 9H).

Step 13: Synthesis of (R)—N—((R)-5-((S)-3-amino-1,1,1-trifluoro-2-hydroxypropan-2-yl)-7-(4-fluorophenyl)-3-(trifluoromethyl)-2,3-dihydrofuro[2,3-c]pyridin-3-yl)-2-methylpropane-2-sulfinamide (compound 1-16)

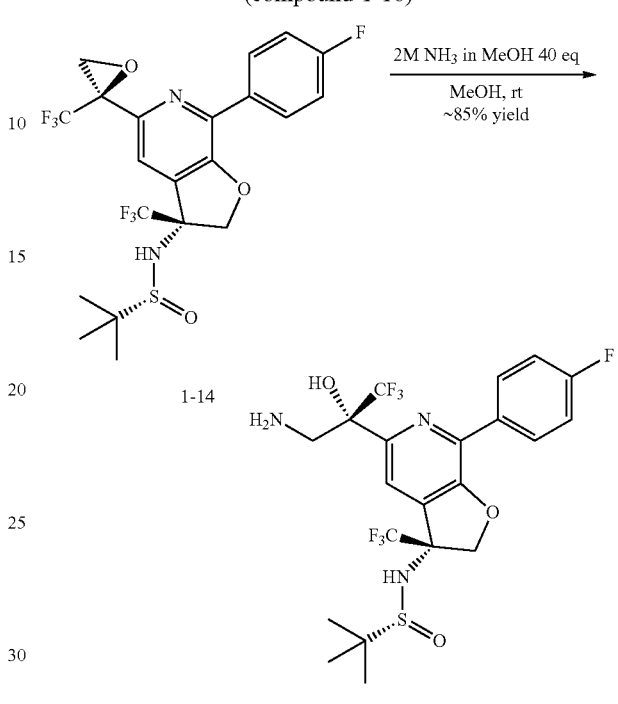

Compound 1-14 (480 mg, 0.937 mmol) was dissolved in ammonia (2N in MeOH, 18.73 mL, 37.5 mmol) at rt. The reaction mixture was stirred at rt for 2 hrs, and then concentrated to remove the solvent and ammonia. The crude product 1-16 (506 mg) was used directly without further purification. LC-MS, $ES^+$ (m/z): 530.4 [M+1].

Step 14: Synthesis of (R)—N—((R)-5-((S)-3-amino-1,1,1-trifluoro-2-hydroxypropan-2-yl)-7-(4-fluorophenyl)-3-(trifluoromethyl)-2,3-dihydrofuro[2,3-c]pyridin-3-yl)-2-methylpropane-2-sulfinamide (compound 1-17) from compound 1-15

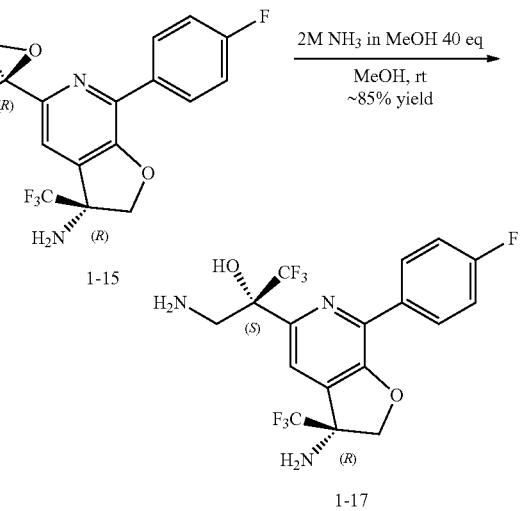

Compound 1-15 (100 mg, 0.245 mmol) was dissolved in ammonia (2N in MeOH, 4.90 mL, 9.80 mmol) at rt. The reaction mixture was stirred at rt for 2 hrs, and then concentrated to remove the solvent and ammonia. The crude product 1-17 was used directly for the next reaction. LC-MS, ES+ (m/z): 426.2 [M+1].

Step 15: Synthesis of (R)—N—((R)-5-((S)-3-amino-1,1,1-trifluoro-2-hydroxypropan-2-yl)-7-(4-fluorophenyl)-3-(trifluoromethyl)-2,3-dihydrofuro[2,3-c]pyridin-3-yl)-2-methylpropane-2-sulfinamide (compound 1-17) from compound 1-16

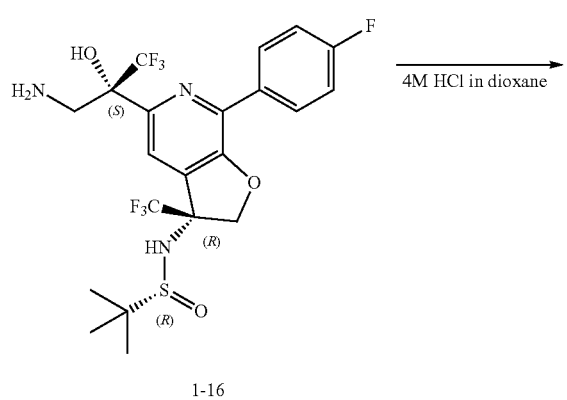

1-16

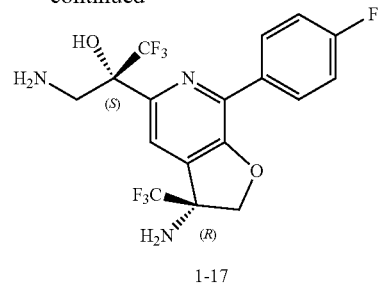

1-17

To a solution of compound 1-16 (crude, 375 mg, 0.708 mmol) in dry MeOH (2.36 mL) at rt was added 4M HCl in dioxane (177 μl, 7.08 mmol). After stirring at rt for 15 min, the reaction mixture was concentrated to dryness. The residue was quenched with sat NaHCO₃, and extracted with EtOAc (3×). The combined organics were dried and concentrated to provide the crude compound 1-17 (322 mg). LC-MS, ES+ (m/z): 426.2 [M+1].

Step 16: Synthesis of (R)—N—((R)-5-((S)-3-amino-1,1,1-trifluoro-2-hydroxypropan-2-yl)-7-(4-fluorophenyl)-3-(trifluoromethyl)-2,3-dihydrofuro[2,3-c]pyridin-3-yl)-2-methylpropane-2-sulfinamide (Example 1)

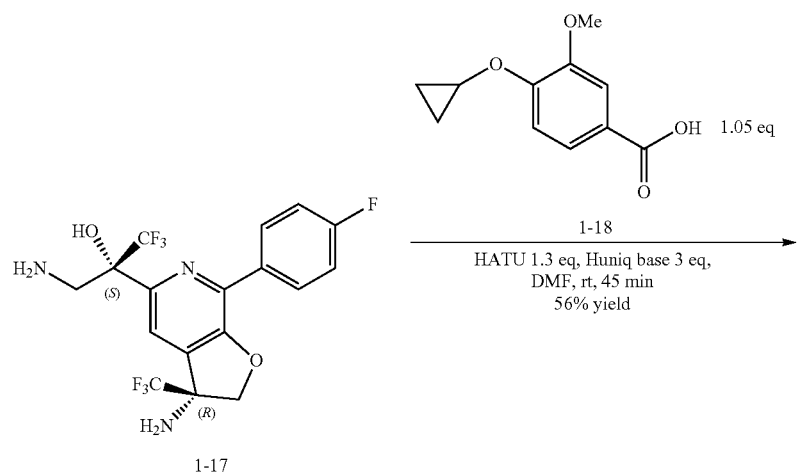

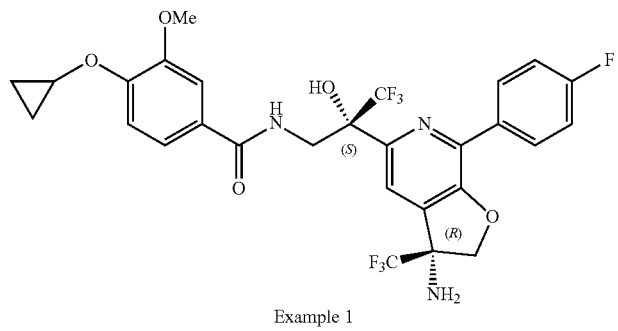

Example 1

To a solution of compound 1-17 (162 mg, 0.381 mmol) in dry DMF (2.54 mL) at rt were added 4-cyclopropoxy-3-methoxybenzoic acid (1-18) (83 mg, 0.400 mmol), and Hunig's base (199 μl, 1.143 mmol). HATU (188 mg, 0.495 mmol) was then added in one portion, the reaction was stirred at room temperature and monitored by LC-MS. After 30-45 min at rt, the reaction mixture was diluted with EtOAc, washed with water, brine, dried and concentrated. Purification of the residue on silica gel with 0-30% EtOAc/cyclohexane provided the desired Example 1 (161 mg, 69% yield). LC-MS, ES$^+$ (m/z): 616.5 [M+H]$^+$. 1H NMR (400 MHz, Chloroform-d) δ 8.23-8.09 (m, 2H), 7.80 (s, 1H), 7.21-7.08 (m, 4H), 7.04 (dd, J=8.4, 2.1 Hz, 1H), 6.49 (brs, 1H), 6.37 (dd, J=8.7, 3.9 Hz, 1H), 4.93 (d, J=10.4 Hz, 1H), 4.71 (dd, J=14.2, 8.6 Hz, 1H), 4.49 (dt, J=10.4, 1.5 Hz, 1H), 3.90 (dd, J=14.2, 3.9 Hz, 1H), 3.79 (s, 3H), 3.71 (tt, J=5.9, 3.4 Hz, 1H), 0.88-0.68 (m, 4H).

Example 2: N—((R)-2-((R)-3-amino-7-(4-fluorophenyl)-3-(trifluoromethyl)-2,3-dihydrofuro[2,3-c]pyridin-5-yl)-3,3,3-trifluoro-2-hydroxypropyl)-4-cyclopropoxy-3-methoxybenzamide

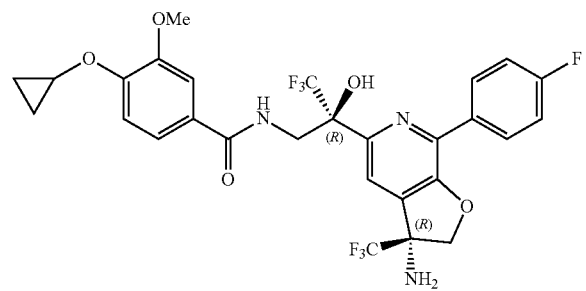

Example 2

Following the similar procedures in Example 1, Ad-Mix-alpha was used to replace Ad-Mix-beta in Step 11 to provide Example 2. LC-MS, ES$^+$ (m/z): 616.4 [M+H]$^+$; $^1$H NMR (400 MHz, Chloroform-d) δ 8.24-8.07 (m, 2H), 7.76 (s, 1H), 7.24 (d, J=2.0 Hz, 1H), 7.21-7.12 (m, 3H), 6.42-6.30 (m, 1H), 4.93 (d, J=10.4 Hz, 1H), 4.64 (dd, J=14.3, 7.8 Hz, 1H), 4.53 (d, J=10.4 Hz, 1H), 4.06 (dd, J=14.3, 4.3 Hz, 1H), 3.83 (s, 3H), 3.73 (dt, J=5.9, 2.8 Hz, 1H), 0.90-0.70 (m, 4H).

Example 3: N—((S)-2-((S)-3-amino-7-(4-fluorophenyl)-3-(trifluoromethyl)-2,3-dihydrofuro[2,3-c]pyridin-5-yl)-3,3,3-trifluoro-2-hydroxypropyl)-4-cyclopropoxy-3-methoxybenzamide

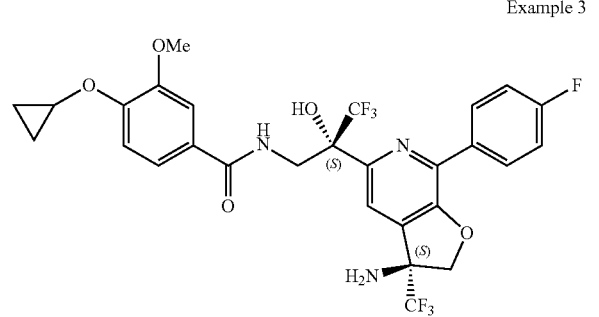

Example 3

Following the similar procedures in Example 1, (S)-2-methylpropane-2-sulfinamide was used to replace (R)-2-methylpropane-2-sulfinamide in Step 5 to provide Example 3. LC-MS, ES$^+$ (m/z): 616.2 [M+H]$^+$; $^1$H NMR (400 MHz, Chloroform-d) δ 8.28-8.03 (m, 2H), 7.76 (s, 1H), 7.23 (d, J=2.0 Hz, 1H), 7.21-7.11 (m, 3H), 7.08 (dd, J=8.3, 2.0 Hz, 1H), 6.47 (s, 1H), 6.42-6.30 (m, 1H), 4.93 (d, J=10.4 Hz, 1H), 4.63 (dd, J=14.3, 7.9 Hz, 1H), 4.52 (d, J=10.4 Hz, 1H), 4.06 (dd, J=14.3, 4.3 Hz, 1H), 3.82 (s, 3H), 3.72 (tt, J=5.8, 3.2 Hz, 1H), 0.90-0.70 (m, 4H).

Example 4: N—((R)-2-((S)-3-amino-7-(4-fluorophenyl)-3-(trifluoromethyl)-2,3-dihydrofuro[2,3-c]pyridin-5-yl)-3,3,3-trifluoro-2-hydroxypropyl)-4-cyclopropoxy-3-methoxybenzamide

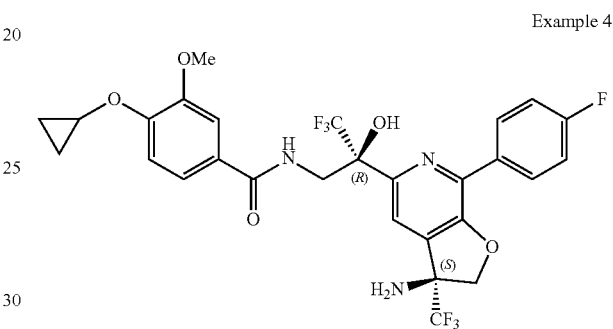

Example 4

Following the similar procedures in Example 1, (S)-2-methylpropane-2-sulfinamide was used to replace (R)-2-methylpropane-2-sulfinamide in Step 5 and Ad-Mix-alpha was used to replace Ad-Mix-beta in Step 11 to provide Example 4. LC-MS, ES$^+$ (m/z): 616.2 [M+H]$^+$; $^1$H NMR (400 MHz, Chloroform-d) δ 8.22-8.13 (m, 2H), 7.79 (s, 1H), 7.22-7.09 (m, 4H), 7.03 (dd, J=8.3, 2.1 Hz, 1H), 6.49 (brs, 1H), 6.35 (dd, J=8.8, 3.9 Hz, 1H), 4.93 (d, J=10.4 Hz, 1H), 4.71 (dd, J=14.2, 8.7 Hz, 1H), 4.49 (dt, J=10.4, 1.5 Hz, 1H), 3.90 (dd, J=14.2, 3.9 Hz, 1H), 3.79 (s, 3H), 3.71 (tt, J=6.0, 3.4 Hz, 1H), 0.87-0.73 (m, 4H).

Example 5: N—((S)-2-((R)-3-amino-7-(4-fluorophenyl)-3-(trifluoromethyl)-2,3-dihydrofuro[2,3-c]pyridin-5-yl)-3,3,3-trifluoro-2-hydroxypropyl)-8-methoxyquinoline-6-carboxamide

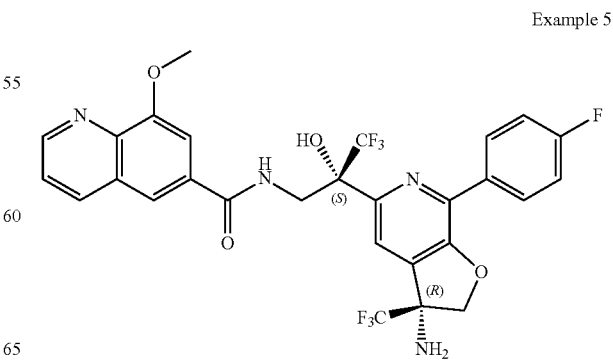

Example 5

Following the similar procedures in Example 1, 8-methoxyquinoline-6-carboxylic acid was used to replace 4-cyclopropoxy-3-methoxybenzoic acid in Step 16 to provide Example 5. LC-MS, ES+ (m/z): 611.4 [M+H]+; 1H NMR (400 MHz, Chloroform-d) δ 8.96 (dd, J=4.3, 1.7 Hz, 1H), 8.22-8.13 (m, 2H), 8.04 (dd, J=8.4, 1.7 Hz, 1H), 7.80 (s, 1H), 7.50-7.42 (m, 2H), 7.24 (d, J=1.7 Hz, 1H), 7.19-7.11 (m, 2H), 6.60 (d, J=7.3 Hz, 1H), 6.48 (s, 1H), 4.93 (d, J=10.3 Hz, 1H), 4.77 (dd, J=14.2, 8.7 Hz, 1H), 4.50 (d, J=10.4 Hz, 1H), 4.04 (s, 3H), 3.95 (dd, J=14.2, 3.8 Hz, 1H).

Example 6: N—((S)-2-((S)-3-amino-7-(4-fluorophenyl)-3-(trifluoromethyl)-2,3-dihydrofuro[2,3-c]pyridin-5-yl)-3,3,3-trifluoro-2-hydroxypropyl)-8-methoxyquinoline-6-carboxamide Example 6

Following the similar procedures in Example 1, (S)-2-methylpropane-2-sulfinamide was used to replace (R)-2-methylpropane-2-sulfinamide in Step 5 and 8-methoxyquinoline-6-carboxylic acid was used to replace 4-cyclopropoxy-3-methoxybenzoic acid in Step 16 to provide Example 6. 611.4 [M+H]+; 1H NMR (400 MHz, Chloroform-d) δ 8.96 (dd, J=4.3, 1.7 Hz, 1H), 8.21-8.12 (m, 2H), 8.09 (dd, J=8.4, 1.6 Hz, 1H), 7.75 (s, 1H), 7.52 (d, J=1.7 Hz, 1H), 7.46 (dd, J=8.3, 4.2 Hz, 1H), 7.31 (d, J=1.7 Hz, 1H), 7.20-7.09 (m, 2H), 6.59 (dd, J=8.3, 3.9 Hz, 1H), 6.42 (s, 1H), 4.94 (d, J=10.5 Hz, 1H), 4.74 (dd, J=14.2, 8.4 Hz, 1H), 4.52 (d, J=10.4 Hz, 1H), 4.11-4.02 (m, 1H), 4.06 (s, 3H).

Example 7: N—((S)-2-((R)-3-amino-7-(4-fluorophenyl)-3-(trifluoromethyl)-2,3-dihydrofuro[2,3-c]pyridin-5-yl)-2-hydroxypropyl)-4-cyclopropoxy-3-methoxybenzamide Example 7

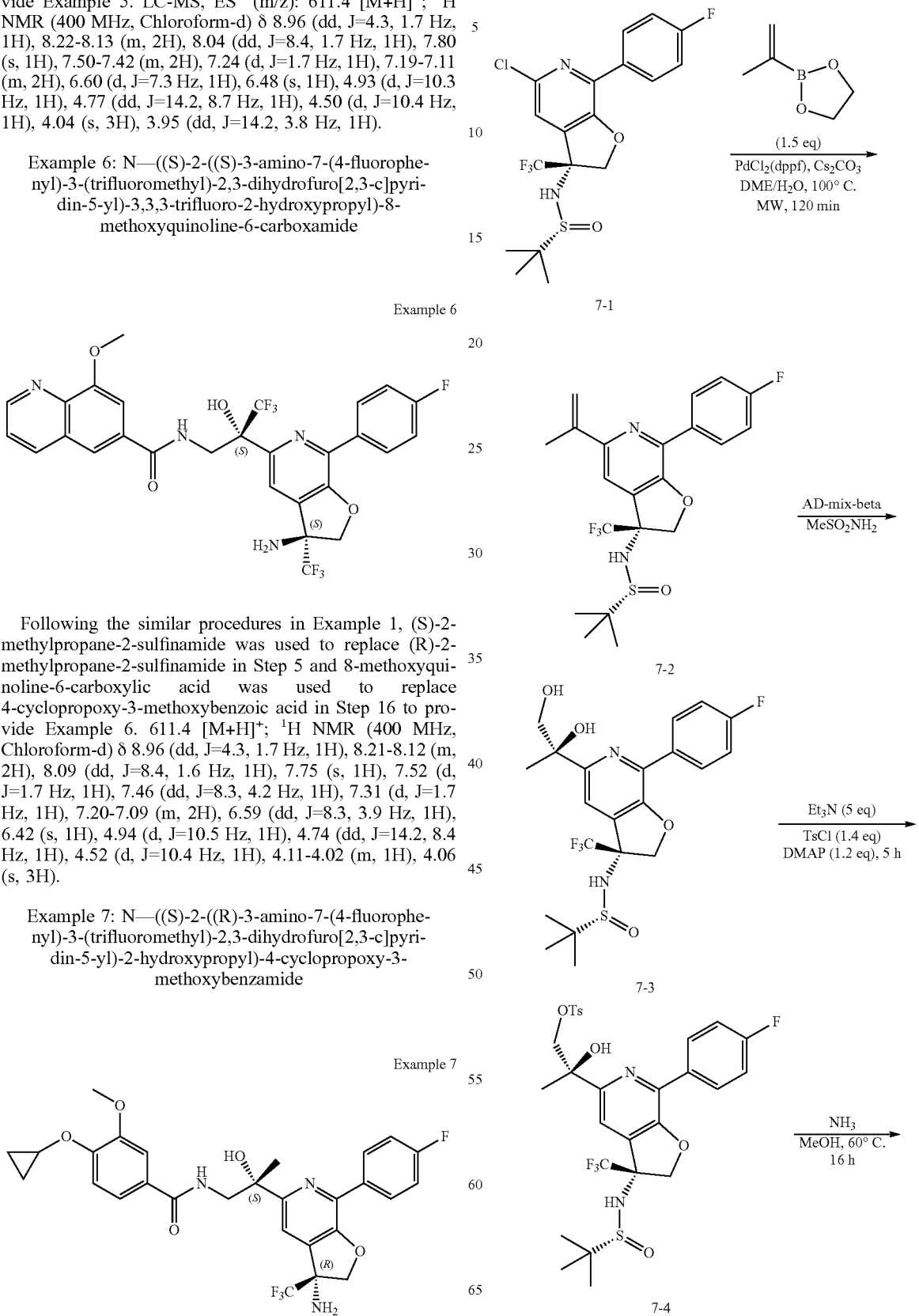

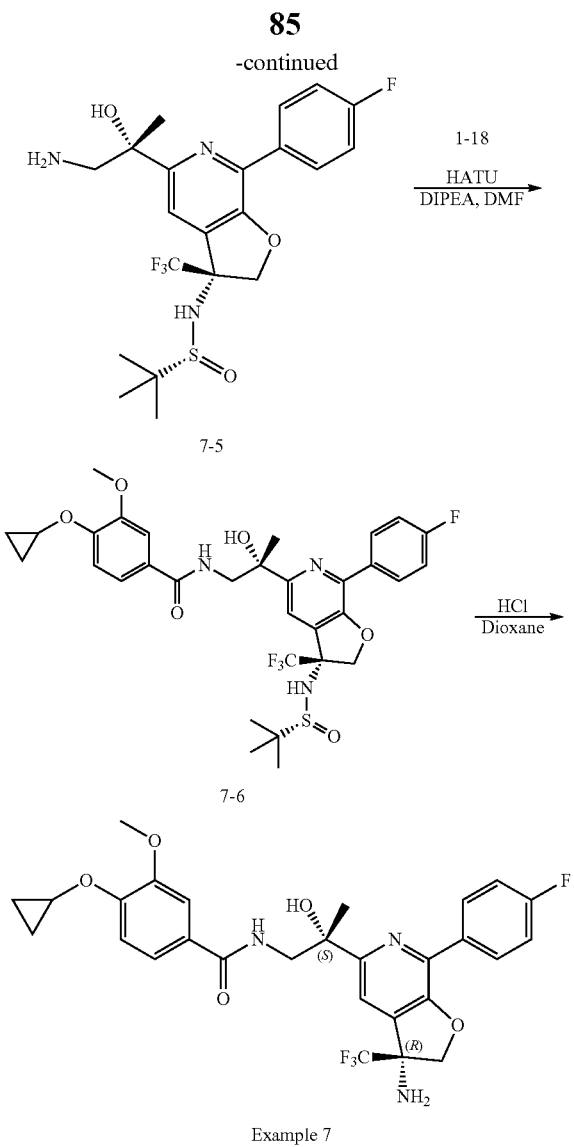

Example 7

Step 1: Synthesis of Compound 7-2

Compound 7-1 (300 mg, 0.687 mmol), 4,4,5,5-tetramethyl-2-(prop-1-en-2-yl)-1,3,2-dioxaborolane (173 μL, 1.030 mmol), and $Cs_2CO_3$ (448 mg, 1.373 mmol) in 1,2-DME (8 mL)/$H_2O$ (2 mL) were combined in a microwave vial and degassed 5 min with $N_2$. $PdCl_2(dppf)$-$CH_2Cl_2$ (56.1 mg, 0.069 mmol) was added. The reaction mixture was heated under microwave at 100° C. for 2 hrs. LCMS suggested complete conversion to the desired product. The reaction mixture was quenched with $H_2O$/brine and extracted with EtOAc (3×). The combined organic layers were washed with brine, dried ($Na_2SO_4$), and concentrated to give an orange oil, which was purified by $SiO_2$ column chromatography eluting with 0 to 50% EtOAc/cyclohexane to give compound 7-2 as a pale yellow amorphous solid (252 mg, 83%). LC-MS, $ES^+$ (m/z): 443.5 $[M+H]^+$; $^1H$ NMR (400 MHz, DMSO-$d_6$) δ 8.33-8.23 (m, 2H), 7.69 (s, 1H), 7.42-7.31 (m, 2H), 6.79 (s, 1H), 5.88 (d, J=1.3 Hz, 1H), 5.39-5.34 (m, 1H), 5.08 (d, J=11.0 Hz, 1H), 5.01 (d, J=11.0 Hz, 1H), 2.23 (s, 3H), 1.07 (s, 9H).

Step 2: Synthesis of Compound 7-3

AD-Mix-beta (3.59 g, 4.61 mmol) and methanesulfonamide (0.219 g, 2.305 mmol) were added to a solution of 7-2 (1.02 g, 2.305 mmol) in t-BuOH (11.53 mL)/$H_2O$ (11.53 mL). The reaction mixture was vigorously stirred overnight at rt. Reaction was then quenched with sat. $Na_2SO_3$ and diluted with EtOAc. Layers were separated and the organic layer was washed with brine, dried ($Na_2SO_4$), filtered, and concentrated to give a crude product, which was purified by silica gel column using cyclohexane/EtOAc (100/0 to 40/60) to give the desired product 7-3 as a white foam (840 mg, 76%). LC-MS, $ES^+$ (m/z): 477.4 [M+H]; $^1H$ NMR (400 MHz, DMSO-$d_6$) δ 8.28-8.18 (m, 2H), 7.77 (s, 1H), 7.40-7.30 (m, 2H), 6.82 (s, 1H), 5.23 (s, 1H), 5.01 (d, J=10.8 Hz, 1H), 4.91 (d, J=10.7 Hz, 1H), 4.62 (t, J=5.9 Hz, 1H), 3.68 (dd, J=10.7, 6.3 Hz, 1H), 3.62 (dd, J=10.7, 5.7 Hz, 1H), 1.42 (s, 3H), 1.01 (s, 9H).

Step 3: Synthesis of Compound 7-4

To a solution of 7-3 (800 mg, 1.679 mmol) in DCM (16 mL) at rt under $N_2$ was added triethylamine (702 μL, 5.04 mmol), followed by addition of p-toluenesulfonyl chloride (384 mg, 2.015 mmol) and DMAP (205 mg, 1.679 mmol). The reaction mixture was stirred at rt for 4 hrs, more TsCl (38 mg, 0.2 mmol) and DMAP (40 mg) were added, stirred for another 2 hrs, and then concentrated. The pale yellow mixture was loaded directly on a silica gel column and eluted with cyclohexane/EtOAc (100/0 to 40/60, 10 min) to give 7-4 as a pale yellow solid (860 mg, 81%). LC-MS, $ES^+$ (m/z): 631.5 [M+H]; $^1H$ NMR (400 MHz, DMSO-$d_6$) δ 8.08-8.00 (m, 2H), 7.72 (s, 1H), 7.50-7.43 (m, 2H), 7.36-7.26 (m, 2H), 7.19 (d, J=8.0 Hz, 2H), 6.83 (s, 1H), 5.94 (s, 1H), 5.05 (d, J=10.9 Hz, 1H), 4.97 (d, J=10.8 Hz, 1H), 4.30 (d, J=9.3 Hz, 1H), 4.23 (d, J=9.3 Hz, 1H), 2.18 (s, 3H), 1.38 (s, 3H), 1.00 (s, 9H).

Step 4: Synthesis of Compound 7-5

Compound 7-4 (0.86 g, 1.364 mmol) was dissolved in 7N ammonia in MeOH solution (12.08 mL, 85 mmol) at room temperature. The reaction mixture was heated in a sealed tube at 60° C. for 16 hrs, and then concentrated to remove the solvent and ammonia. The crude product 7-5 (850 mg, quart.) was used directly for the next reaction.

Step 5: Synthesis of Compound 7-6

To a solution of 7-5 (350 mg, 0.736 mmol) and 4-cyclopropoxy-3-methoxybenzoic acid (1-18) (161 mg, 0.773 mmol) in dry DMF (10 mL) at rt was added Hunig's base (513 μL, 2.94 mmol), followed by addition of HATU (364 mg, 0.957 mmol). The resulting mixture was stirred at rt for 2 hrs, diluted with EtOAc, washed with water, brine (2×), dried over $Na_2SO_4$ and concentrated. The crude was purified by $SiO_2$ column chromatography eluting with cyclohexane/acetone (100/0 to 60/40) to give 7-6 as a colorless oil (460 mg, 94%). LC-MS, $ES^+$ (m/z): 666.3 [M+H]; $^1H$ NMR (400 MHz, DMSO-$d_6$) δ 8.29-8.15 (m, 3H), 7.81 (s, 1H), 7.39 (dd, J=8.4, 2.0 Hz, 1H), 7.39-7.31 (m, 3H), 7.23 (d, J=8.4 Hz, 1H), 6.82 (s, 1H), 5.89 (s, 1H), 5.02 (d, J=10.8 Hz, 1H), 4.90 (d, J=10.8 Hz, 1H), 3.91-3.73 (m, 2H), 3.73 (s, 3H), 3.64 (dd, J=13.3, 6.1 Hz, 1H), 1.51 (s, 3H), 1.02 (s, 9H), 0.84-0.75 (m, 2H), 0.67 (q, J=3.8, 2.5 Hz, 2H).

Step 6: Synthesis of Example 7

Compound 7-6 (0.46 g, 0.691 mmol) was dissolved in 4M HCl in dioxane (8.64 mL, 34.6 mmol), and the solution was stirred at rt for 50 min. The resulting white slurry was concentrated to dryness, treated with sat. NaHCO₃, and extracted with EtOAc (3×). The combined organic layers were washed with brine, dried over Na₂SO₄, and concentrated. The residue was purified by silica gel chromatography using cyclohexane/EtOAc (100/0 to 30/70) to give Example 7 as a white solid (300 mg. 77%). LC-MS, ES⁺ (m/z): 562.4 [M+H]; ¹H NMR (400 MHz, DMSO-d₆) δ 8.30-8.18 (m, 3H), 7.80 (s, 1H), 7.43-7.35 (m, 1H), 7.39-7.30 (m, 3H), 7.23 (dd, J=8.4, 0.8 Hz, 1H), 5.85 (d, J=0.8 Hz, 1H), 4.89 (d, J=10.4 Hz, 1H), 4.50 (d, J=10.4 Hz, 1H), 3.87 (tt, J=6.1, 3.0 Hz, 1H), 3.85-3.73 (m, 1H), 3.74 (s, 3H), 3.60 (dd, J=13.4, 5.9 Hz, 1H), 3.07 (s, 2H), 1.51 (s, 3H), 0.86-0.62 (m, 4H).

Example 8: N—((S)-2-(R)-3-amino-7-(4-fluorophenyl)-3-(trifluoromethyl)-2,3-dihydrofuro[2,3-c]pyridin-5-yl)-3-fluoro-2-hydroxypropyl)-4-cyclopropoxy-3-methoxybenzamide

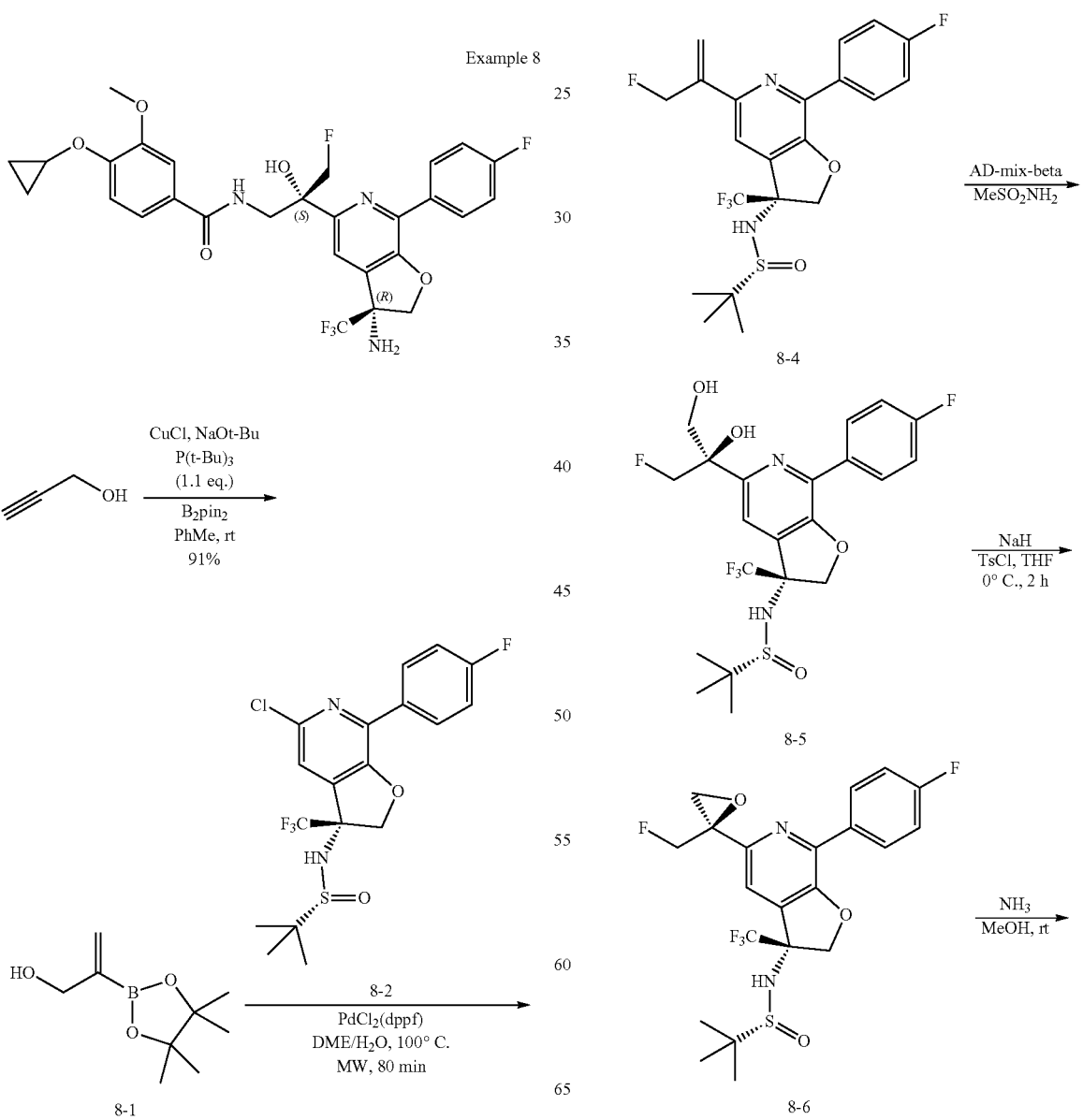

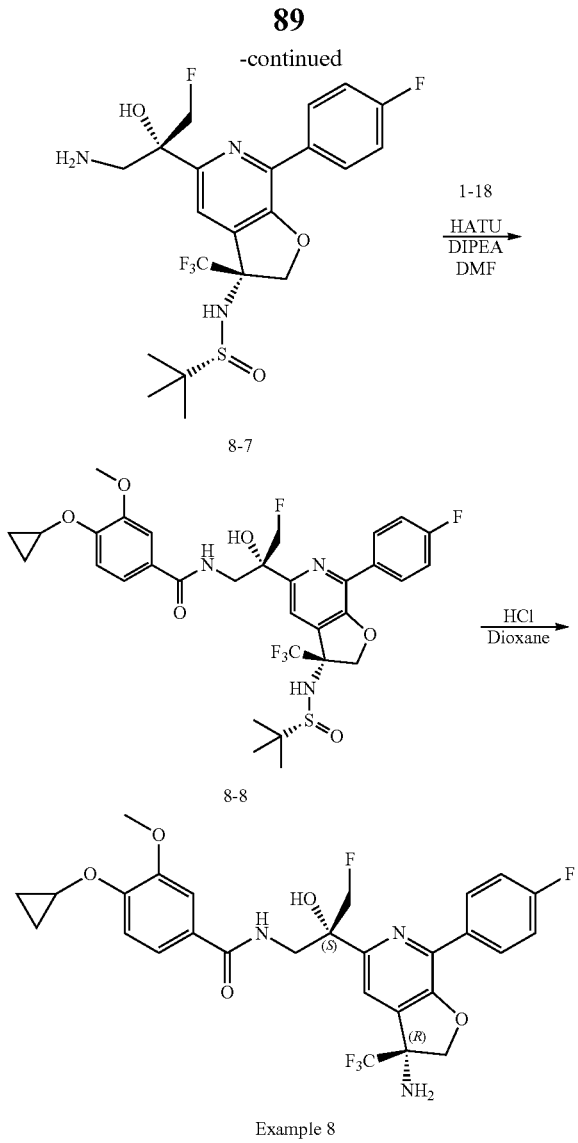

Example 8

Step 1: Synthesis of Compound 8-1

To a mixture of sodium tert-butoxide (129 mg, 1.338 mmol), copper(I) chloride (88 mg, 0.892 mmol), and bis(pinacolato)diboron (2491 mg, 9.81 mmol) in toluene (12.0 mL) at 0° C. was added a solution of tri-t-butylphosphine (1.070 mL, 1.070 mmol) in toluene (6.00 mL), followed by addition of a solution of prop-2-yn-1-ol (0.519 mL, 8.92 mmol) in toluene (6.00 mL). The reaction mixture was warmed up to rt and stirred for 1 h, and then cooled to 0° C., quenched with HCl in MeOH (1.25 M, 15 mL), and concentrated to give a yellow suspension, which was suspended in DCM and filtered through celite, rinsing with DCM. The filtrate was concentrated to give 3.26 g of a yellow oil, which was purified by column chromatography eluting with cyclohexane/EtOAc (0% EtOAc→25% EtOAc, 40 g column) to give compound 8-1 (1.5 g, 8.15 mmol, 91% yield) as a white wax.

Step 2: Synthesis of Compound 8-3

Compound 8-1 (190 mg, 1.03 mmol), 8-2 (300 mg, 0.687 mmol), and $Cs_2CO_3$ (448 mg, 1.373 mmol) in 1,2-DME (4 mL)/$H_2O$ (1 mL) were combined in a microwave vial and degassed 10 min with $N_2$. $PdCl_2(dppf)$-$CH_2Cl_2$ (56.1 mg, 0.069 mmol) was added, the vial was then sealed and heated in the microwave at 100° C. for 1.5 hrs. The reaction mixture was then quenched with $H_2O$/brine and diluted with EtOAc. Layers were separated and the aqueous layer was extracted with EtOAc (2×). The combined organic layers were dried ($Na_2SO_4$), filtered, and concentrated to give an orange oil, which was purified by column chromatography eluting with cyclohexane/acetone (100/0 to 70/30) to give 8-3 as a pale yellow amorphous solid (107 mg, 34%). LC-MS, $ES^+$ (m/z): 459.3 $[M+H]^+$.

Step 3: DAST (57.6 μL, 0.436 mmol) was added to a solution of 8-3 (100 mg, 0.218 mmol) in DCM (8 mL) at 0° C. in a plastic vial. The reaction mixture was stirred at 0° C. for 2 hrs, and then quenched carefully with sat. $NaHCO_3$ and diluted with $CH_2Cl_2$. Layers were separated and the aqueous layer was extracted with $CH_2Cl_2$ (2×). The combined organic layers were dried ($Na_2SO_4$), filtered, and concentrated to give a yellow residue, which was purified by column chromatography eluting with cyclohexane/EtOAc (0% EtOAc→50% EtOAc) to give the desired product 8-4 as a pale yellow oil (20 mg, 20%). LC-MS, $ES^+$ (m/z): 461.3 $[M+H]^+$.

Step 4: AD-Mix-beta (64.3 mg, 0.083 mmol) and methanesulfonamide (3.92 mg, 0.041 mmol) were added to a solution of 8-4 (19 mg, 0.041 mmol) in t-BuOH (0.206 mL)/$H_2O$ (0.206 mL) at rt. The reaction mixture was vigorously stirred overnight at rt, and the quenched with sat. $Na_2SO_3$ and diluted with EtOAc. The combined organic layers were washed with brine, dried ($Na_2SO_4$), filtered, and concentrated to give a crude product, which was purified by silica gel column chromatography using cyclohexane/EtOAc (100/0 to 40/60) to give the desired product 8-5 as a pale yellow oil (9 mg, 44%). LC-MS, $ES^+$ (m/z): 495.2 [M+H]; $^1$H-NMR (400 MHz, $CDCl_3$) δ 8.26-8.18 (m, 2H), 7.60 (s, 1H), 7.20 (t, J=8.7 Hz, 2H), 5.28 (d, J=11.5 Hz, 1H), 5.06 (s, 1H), 5.02 (d, J=11.5 Hz, 1H), 4.76-4.57 (m, 2H), 4.00 (s, 2H), 1.43 (s, 9H).

Step 5: Synthesis of Compound 8-6

To a solution of compound 8-5 (9 mg, 0.018 mmol in dry THF (0.8 mL) at 0° C. was added NaH (60% oil dispersion, 2.184 mg, 0.055 mmol), followed by addition of p-toluenesulfonyl chloride (4.16 mg, 0.022 mmol). The reaction mixture was stirred at 0° C. for 2 hrs, quenched with water, and extracted with ethyl acetate (3×). The combined organic layers were washed with brine, dried over $Na_2SO_4$, and concentrated. The crude product 8-6 was used directly for the next reaction. LC-MS, $ES^+$ (m/z): 477.3 $[M+H]^+$.

Step 6: Synthesis of Compound 8-7

Crude compound 8-6 (9 mg, 0.019 mmol) was dissolved in ammonia solution (7N) in MeOH (216 μL, 1.511 mmol) at rt. The reaction mixture was stirred at rt for 16 hrs, and then concentrated to remove the solvent and ammonia. The crude product 8-7 was used directly for the next reaction. LC-MS, $ES^+$ (m/z): 494.2 $[M+H]^+$.

Step 7: Synthesis of Compound 8-8

To a solution of 8-7 (9 mg, 0.018 mmol) and 4-cyclopropoxy-3-methoxybenzoic acid (1-18) (3.99 mg, 0.019 mmol) in dry DMF (0.18 mL) at rt was added Hunig's base (12.7 μL, 0.073 mmol), followed by addition of HATU (9.01 mg, 0.024 mmol). The resulting mixture was stirred at rt for 3 hrs, diluted with EtOAc, washed with water, brine (2×), dried over Na₂SO₄ and concentrated. The crude product was purified by silica gel chromatography eluting with cyclohexane/acetone (100/0 to 60/40, 10 min) to afford compound 8-8 as a colorless oil (6 mg, 50% over three steps). LC-MS, ES⁺ (m/z): 684.2 [M+H]⁺.

Step 8: Synthesis of Example 8

Compound 8-8 (6 mg, 8.78 µmol) was dissolved in 4M HCl in dioxane (219 µL, 0.878 mmol), and the solution was stirred at rt for 15 min. The reaction mixture was then concentrated to dryness, treated with sat. NaHCO₃, and extracted with EtOAc (2×). The combined organic layers were washed with brine, dried over Na₂SO₄, and concentrated. The residue was purified by chromatography on silica gel using DCM/MeOH (100/0 to 90/10, 10 min) to give the desired Example 8 as a white solid (4 mg, 79%). LC-MS, ES⁺ (m/z): 580.4 [M+H]⁺.

Example 9: N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-4-cyclopropoxy-3-methoxybenzamide Example 9

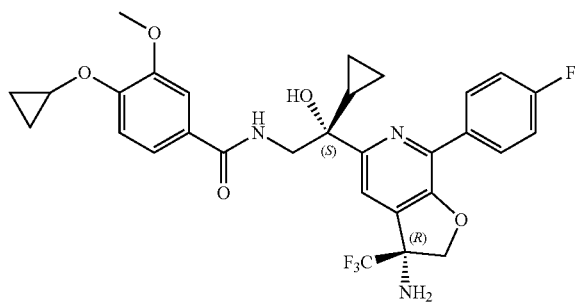

Example 9 was prepared by a similar method as for Example 7. LC-MS, ES⁺ (m/z): 558.2 [M+H]⁺; ¹H NMR (400 MHz, DMSO-d₆) δ 8.24 (d, J=6.0 Hz, 1H), 8.17 (dd, J=8.8, 5.6 Hz, 2H), 7.61 (s, 1H), 7.29-7.18 (m, 4H), 7.12 (d, J=8.3 Hz, 1H), 5.67 (s, 1H), 4.77 (d, J=10.4 Hz, 1H), 4.38 (d, J=10.3 Hz, 1H), 3.86-3.69 (m, 3H), 3.62 (s, 3H), 2.97 (s, 2H), 1.43 (s, 1H), 0.68 (d, J=6.8 Hz, 2H), 0.55 (s, 2H), 0.42 (s, 1H), 0.28 (d, J=8.2 Hz, 1H), 0.15 (s, 1H), 0.00 (m, 1H).

Example 10: (N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-8-methoxyquinoline-6-carboxamide Example 10

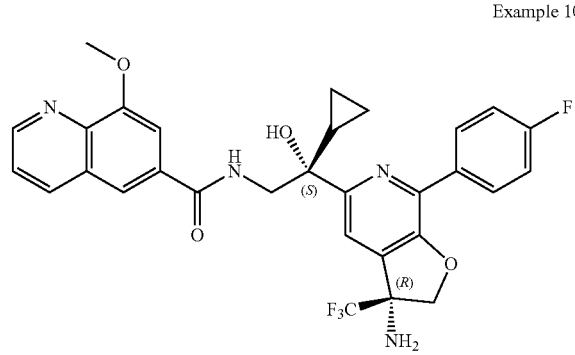

Example 10 was prepared by a similar method as for Example 7. LC-MS, ES⁺ (m/z): 583.4 [M+H]⁺; ¹H NMR (400 MHz, DMSO-d₆) δ 8.76 (dd, J=4.2, 1.7 Hz, 1H), 8.45 (t, J=5.8 Hz, 1H), 8.14 (ddd, J=8.6, 5.3, 3.6 Hz, 3H), 7.72 (d, J=1.7 Hz, 1H), 7.60 (s, 1H), 7.45 (dd, J=8.3, 4.1 Hz, 1H), 7.28 (d, J=1.7 Hz, 1H), 7.18 (t, J=8.9 Hz, 2H), 5.48 (s, 1H), 4.73 (d, J=10.4 Hz, 1H), 4.35 (d, J=10.5 Hz, 1H), 3.81 (s, 5H), 2.92 (s, 2H), 1.49-1.39 (m, 1H), 0.44 (dd, J=9.7, 4.6 Hz, 1H), 0.27 (s, 1H), 0.16 (dd, J=9.4, 4.3 Hz, 1H), 0.00 (m, 1H).

Example 11: N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-8-cyclopropoxyquinoline-6-carboxamide Example 11

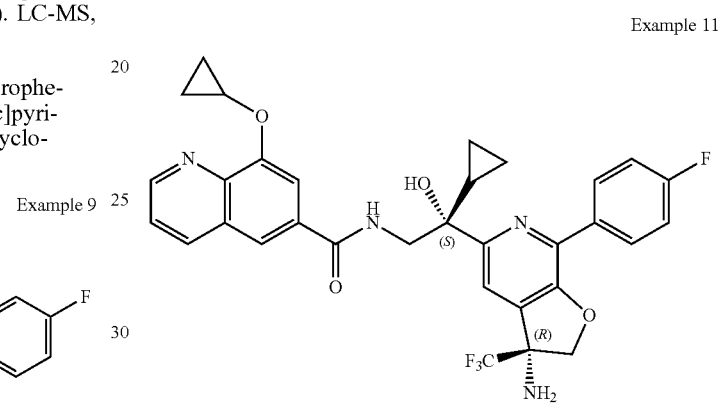

Example 11 was prepared by a similar method as for Example 7. LC-MS, ES⁺ (m/z): 609.3 [M+H]⁺; ¹H NMR (400 MHz, DMSO-d₆) δ 8.74 (dd, J=4.2, 1.7 Hz, 1H), 8.41 (t, J=5.9 Hz, 1H), 8.18-8.09 (m, 3H), 7.72 (d, J=1.7 Hz, 1H), 7.60 (d, J=1.8 Hz, 2H), 7.45 (dd, J=8.3, 4.2 Hz, 1H), 7.22-7.09 (m, 2H), 5.47 (s, 1H), 4.72 (d, J=10.4 Hz, 1H), 4.35 (d, J=10.4 Hz, 1H), 3.86 (p, J=3.1 Hz, 1H), 3.83-3.78 (m, 2H), 2.92 (s, 2H), 1.42 (m, 1H), 0.71 (d, J=6.1 Hz, 2H), 0.61 (s, 2H), 0.49-0.41 (m, 1H), 0.27 (dd, J=9.0, 5.0 Hz, 1H), 0.17 (dt, J=10.0, 4.8 Hz, 1H), 0.00 (m, 1H).

Example 12: N—((S)-2-((R)-3-amino-7-(4-fluorophenyl)-3-(trifluoromethyl)-2,3-dihydrofuro[2,3-c]pyridin-5-yl)-2-hydroxy-3,3-dimethylbutyl)-4-cyclopropoxy-3-methoxybenzamide Example 12

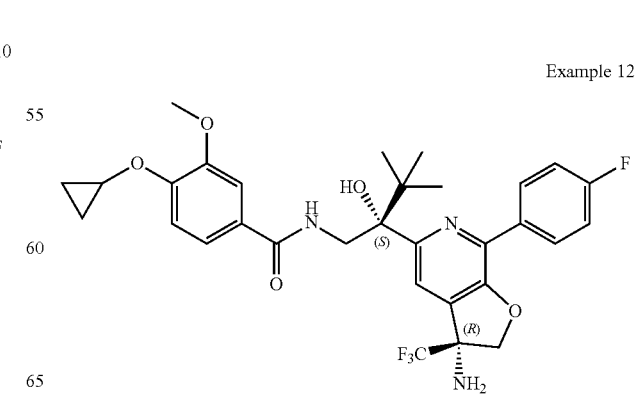

Example 12 was prepared by a similar method as for Example 7. LC-MS, ES+ (m/z): 604.6 [M+H]+; 1H NMR (400 MHz, DMSO-d6) δ 8.28 (dd, J=8.9, 5.7 Hz, 2H), 7.84 (s, 1H), 7.76 (s, 1H), 7.34 (t, J=8.9 Hz, 2H), 7.18-7.08 (m, 3H), 5.80 (s, 1H), 4.87 (d, J=10.4 Hz, 1H), 4.51 (d, J=10.5 Hz, 1H), 4.39 (dd, J=13.5, 7.2 Hz, 1H), 3.82 (dq, J=6.0, 3.0 Hz, 1H), 3.77-3.69 (m, 1H), 3.64 (s, 3H), 3.02 (s, 2H), 0.99 (s, 9H), 0.74 (t, J=6.4 Hz, 2H), 0.62 (s, 2H).

Example 13: 2-(((R)-5-((S)-3-(4-cyclopropoxy-3-methoxybenzamido)-1,1,1-trifluoro-2-hydroxypropan-2-yl)-7-(4-fluorophenyl)-3-(trifluoromethyl)-2,3-dihydrofuro[2,3-c]pyridin-3-yl)amino)-2-oxoethyl acetate 0° C. and monitored by LC-MS. After stirring at 0° C. for 2 hrs, another portion of 2-chloro-2-oxoethyl acetate (21.3 mg, 0.156 mmol) was added and the reaction was warmed to rt and stirred overnight.

Work-up: the reaction mixture was diluted with DCM, washed with water, brine, dried over Na2SO4, and concentrated. Purification of the residue on silica gel with 0-50% EtOAc/cyclohexane provided the desired Example 13 (15 mg, 32% yield). LC-MS, ES+ (m/z): 716.4 [M+H]+.

Example 14: 4-cyclopropoxy-3-methoxy-N—((S)-3,3,3-trifluoro-2-((R)-7-(4-fluorophenyl)-3-(2-hydroxyacetamido)-3-(trifluoromethyl)-2,3-dihydrofuro[2,3-c]pyridin-5-yl)-2-hydroxypropyl)benzamide

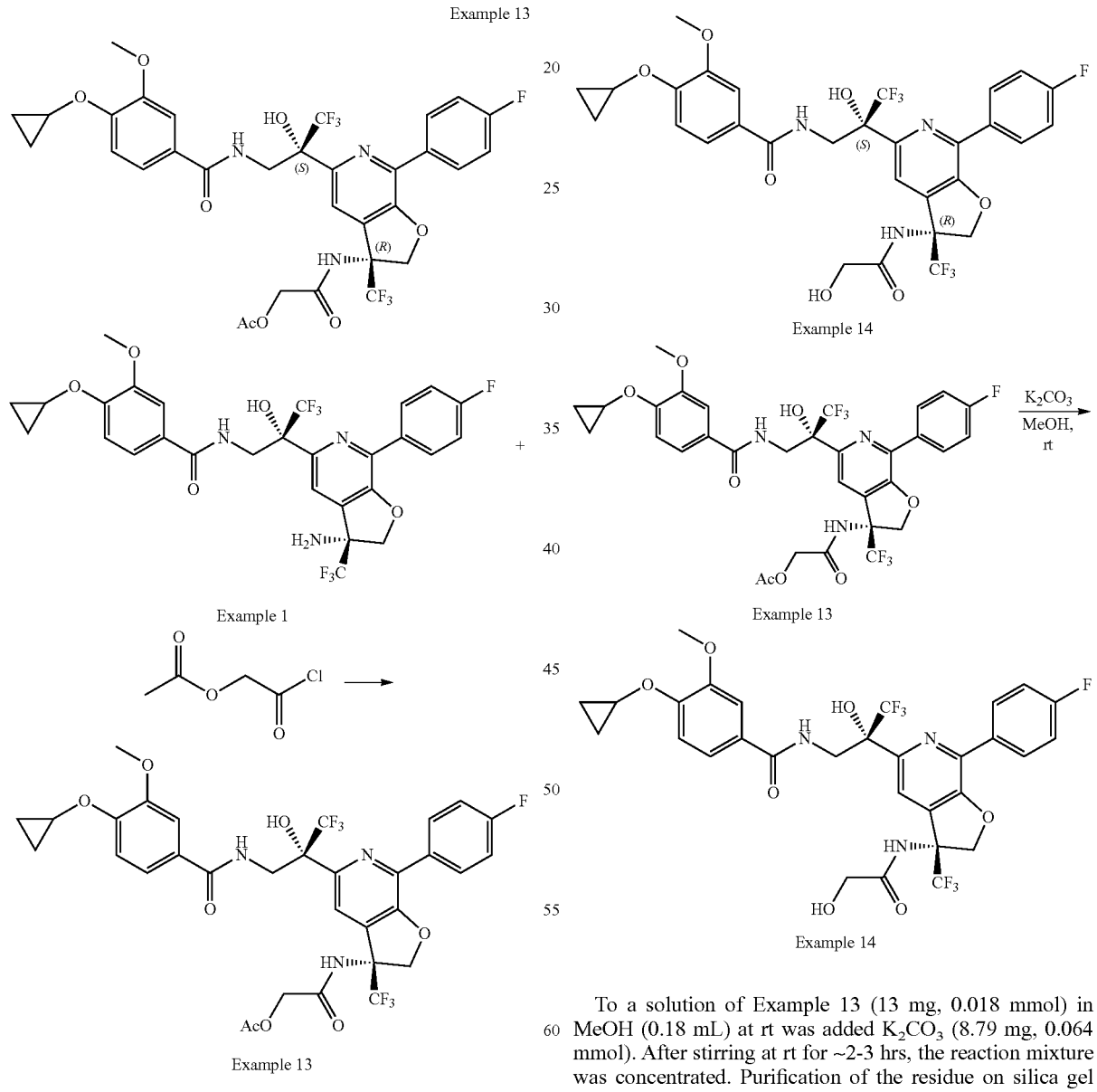

To a solution of Example 1 (40 mg, 0.065 mmol) in dry DCM (0.33 mL) at 0° C. was added triethylamine (54.3 μL, 0.390 mmol), followed by addition of 2-chloro-2-oxoethyl acetate (14.2 mg, 0.104 mmol). The reaction was stirred at To a solution of Example 13 (13 mg, 0.018 mmol) in MeOH (0.18 mL) at rt was added K2CO3 (8.79 mg, 0.064 mmol). After stirring at rt for ~2-3 hrs, the reaction mixture was concentrated. Purification of the residue on silica gel with 0-70% EtOAc/cyclohexane provided the desired Example 14 (8 mg, 65% yield). LC-MS, ES+ (m/z): 674.3 [M+H]+. 1H NMR (400 MHz, Chloroform-d) δ 8.26-8.17 (m, 2H), 7.71 (s, 1H), 7.47 (s, 1H), 7.24-7.14 (m, 2H), 7.12 (d, J=8.3 Hz, 1H), 6.91-6.82 (m, 2H), 6.37 (s, 1H), 6.31 (d, J=10.4 Hz, 1H), 5.29 (d, J=11.0 Hz, 1H), 5.05 (d, J=11.1 Hz, 1H), 4.91 (dd, J=14.2, 10.1 Hz, 1H), 4.50 (brs, 1H), 3.89 (dd, J=16.2, 6.7 Hz, 1H), 3.74 (s, 3H), 3.70 (tt, J=6.0, 3.4 Hz, 1H), 3.63 (dd, J=14.2, 3.1 Hz, 1H), 3.55 (d, J=16.0 Hz, 1H), 0.85-0.73 (m, 4H).

Example 15: methyl ((R)-5-((S)-1-(4-cyclopropoxy-3-methoxybenzamido)-2-hydroxypropan-2-yl)-7-(4-fluorophenyl)-3-(trifluoromethyl)-2,3-dihydrofuro[2,3-c]pyridin-3-yl)carbamate

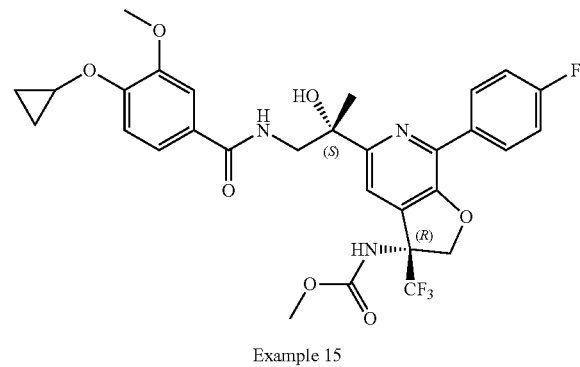

Example 15

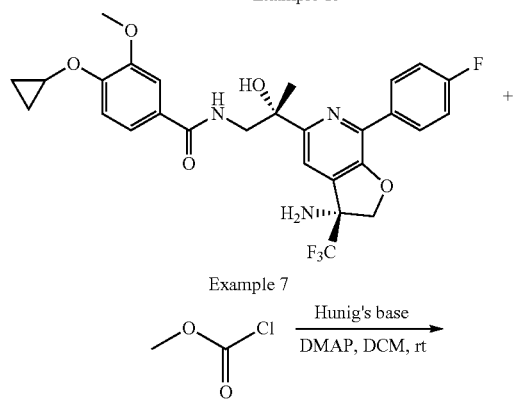

Example 7

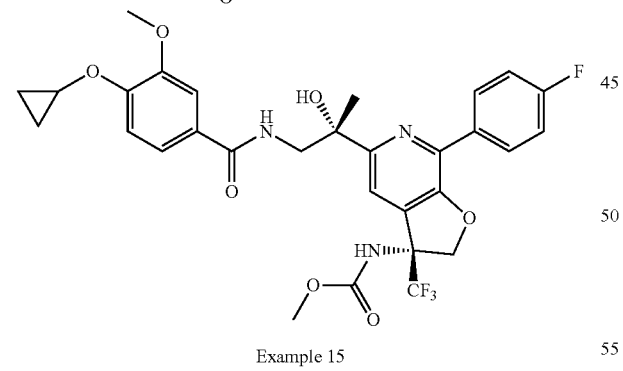

Example 15

To a solution of Example 7 (26 mg, 0.046 mmol) in dry DCM (0.23 mL) at rt was added Hunig's base (48.5 µl, 0.278 mmol), followed by addition of methyl chloroformate (8.75 mg, 0.093 mmol). After stirring at rt for 45 min, another portion of methyl chloroformate (8.75 mg, 0.093 mmol) was added followed by addition of DMAP (5.66 mg, 0.046 mmol). The reaction mixture was stirred at rt o/n. Work-up: the reaction mixture was diluted with DCM, washed with sat NaHCO₃, water, brine, dried over Na₂SO₄ and concentrated. Purification of the residue on silica gel with 0-70% EtOAc/cyclohexane provided the desired Example 15 (5 mg, 17% yield). LC-MS, ES⁺ (m/z): 620.2 [M+H]⁺; 1H NMR (400 MHz, Chloroform-d) δ 8.25-8.12 (m, 2H), 7.66 (s, 1H), 7.22-7.12 (m, 3H), 7.10 (d, J=8.3 Hz, 1H), 7.05 (d, J=8.6 Hz, 1H), 6.53 (s, 1H), 6.33 (s, 1H), 5.74 (s, 1H), 5.22 (d, J=11.8 Hz, 1H), 5.10 (d, J=11.3 Hz, 1H), 4.34 (dd, J=14.0, 8.7 Hz, 1H), 3.79 (s, 3H), 3.75-3.70 (m, 1H), 3.70 (s, 3H), 3.56 (dd, J=14.1, 4.0 Hz, 1H), 1.65 (s, 3H), 0.88-0.74 (m, 4H).

Example 16: N—((S)-2-((R)-3-amino-7-(4-fluorophenyl)-3-(trifluoromethyl)-2,3-dihydrofuro[2,3-c]pyridin-5-yl)-2-hydroxypropyl)-8-cyclopropoxyquinoline-6-carboxamide

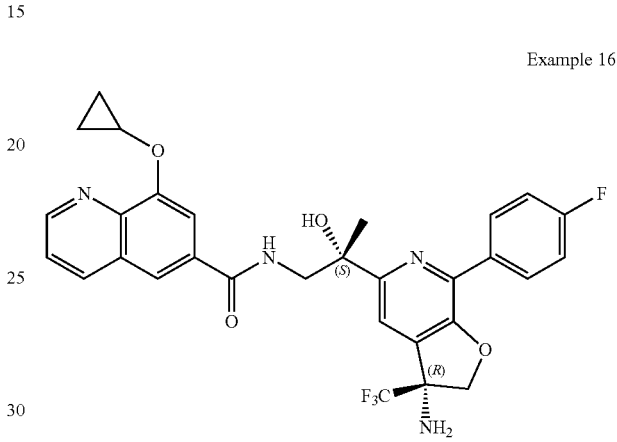

Example 16

Example 16 was prepared by a similar method as for Example 7. LC-MS, ES⁺ (m/z): 583.33 [M+H]⁺; ¹H NMR (400 MHz, DMSO-d₆) δ 8.90 (dd, J=4.2, 1.7 Hz, 1H), 8.48 (t, J=6.0 Hz, 1H), 8.31-8.23 (m, 3H), 7.95 (d, J=1.7 Hz, 1H), 7.85-7.77 (m, 2H), 7.60 (dd, J=8.3, 4.2 Hz, 1H), 7.37-7.28 (m, 2H), 5.79 (s, 1H), 4.89 (d, J=10.4 Hz, 1H), 4.50 (d, J=10.5 Hz, 1H), 4.09-3.99 (m, 1H), 3.86 (dd, J=13.3, 5.8 Hz, 1H), 3.71 (dd, J=13.3, 6.1 Hz, 1H), 3.07 (s, 2H), 1.57 (s, 3H), 0.86 (t, J=5.8 Hz, 2H), 0.77 (s, 2H).

Example 17: N—((S)-2-((R)-3-amino-7-(4-fluorophenyl)-3-(trifluoromethyl)-2,3-dihydrofuro[2,3-c]pyridin-5-yl)-2-hydroxypropyl)-8-methoxyquinoline-6-carboxamide

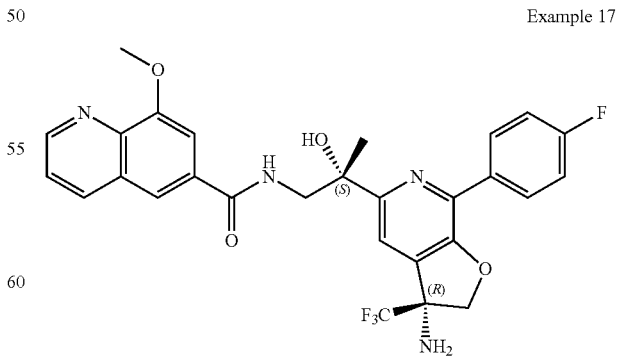

Example 17

Example 17 was prepared by a similar method as for Example 7. LC-MS, ES⁺ (m/z): 557.22 [M+H]⁺; ¹H NMR (400 MHz, DMSO-d₆) δ 8.91 (dd, J=4.1, 1.7 Hz, 1H), 8.51

(t, J=6.0 Hz, 1H), 8.33-8.23 (m, 3H), 7.94 (d, J=1.7 Hz, 1H), 7.82 (s, 1H), 7.61 (dd, J=8.3, 4.2 Hz, 1H), 7.48 (d, J=1.7 Hz, 1H), 7.32 (t, J=8.9 Hz, 2H), 5.78 (s, 1H), 4.89 (d, J=10.4 Hz, 1H), 4.50 (d, J=10.4 Hz, 1H), 3.97 (s, 3H), 3.85 (dd, J=13.4, 5.8 Hz, 1H), 3.71 (dd, J=13.3, 6.2 Hz, 1H), 3.06 (s, 2H), 1.57 (s, 3H).

Example 18: N—((S)-2-((R)-3-amino-7-(4-fluorophenyl)-3-(trifluoromethyl)-2,3-dihydrofuro[2,3-c]pyridin-5-yl)-2-hydroxypropyl)-4-cyclopropoxy-3-(pyridin-3-yl)benzamide Example 18

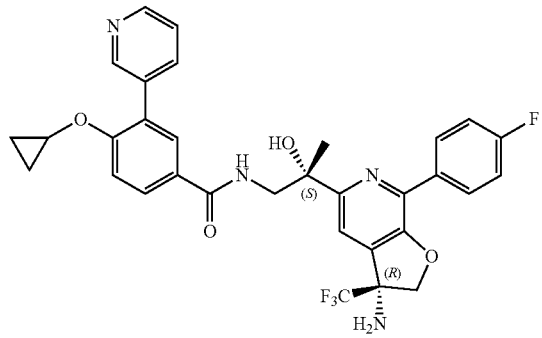

Step 1~4: Synthesis of 4-cyclopropoxy-3-(pyridin-3-yl)benzoic acid (18-6)

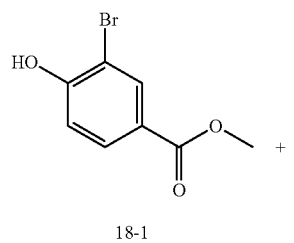

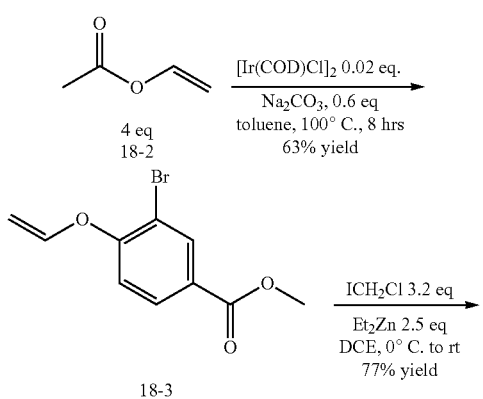

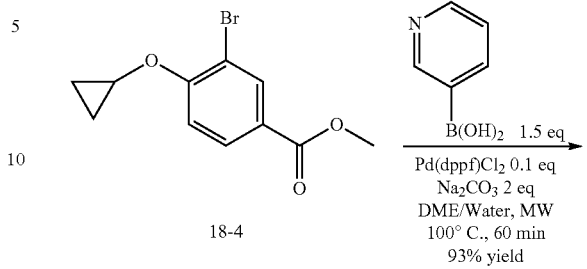

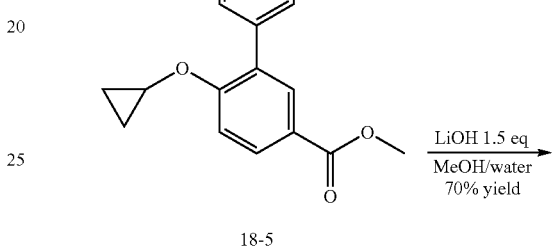

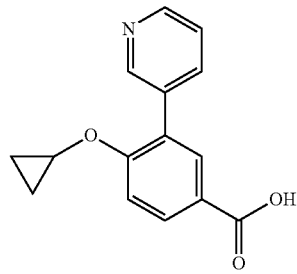

Compound 18-6 was prepared according to the above scheme under standard conditions. LC-MS, ES+ (m/z): 256.2 [M+H]+;

Step 5-6: Synthesis of Example 18

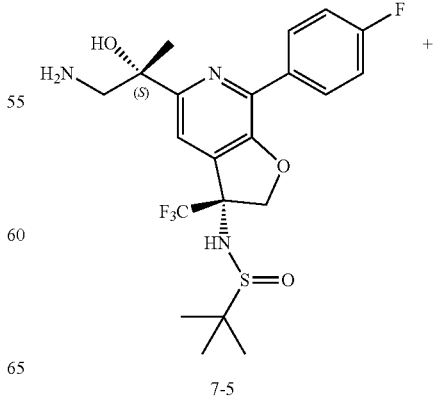

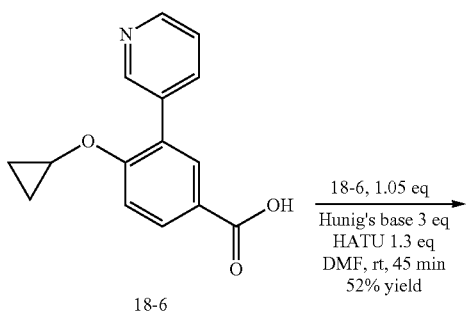

18-6

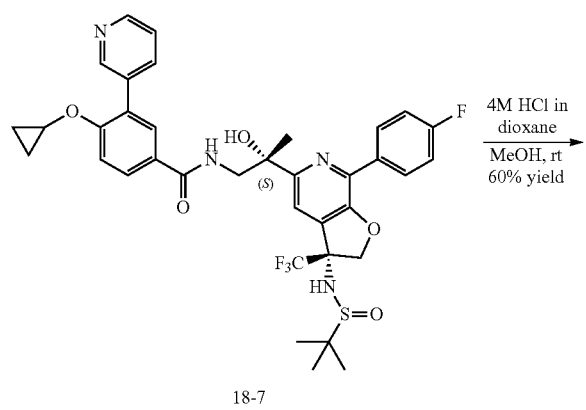

18-7

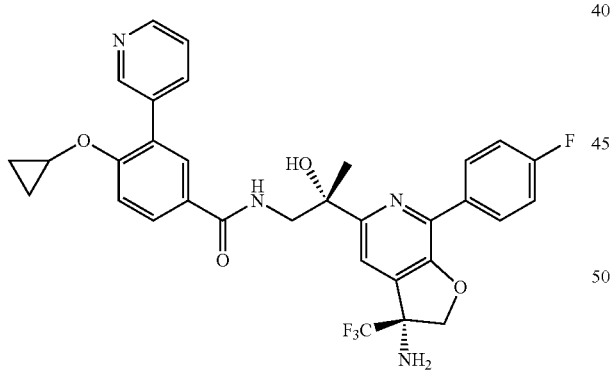

Example 18

As shown in the above scheme, Example 18 was prepared by a similar method as for Example 7. LC-MS, ES+ (m/z): 609.26 [M+H]+; 1H NMR (400 MHz, Chloroform-d) δ 8.73-8.60 (m, 1H), 8.53 (d, J=4.9 Hz, 1H), 8.17 (dd, J=8.7, 5.5 Hz, 2H), 7.77 (d, J=8.0 Hz, 1H), 7.63 (d, J=8.5 Hz, 1H), 7.58 (s, 2H), 7.33 (dd, J=8.0, 4.9 Hz, 1H), 7.29 (d, J=8.6 Hz, 1H), 7.11 (t, J=8.6 Hz, 2H), 6.64 (d, J=6.1 Hz, 1H), 4.89 (d, J=10.3 Hz, 1H), 4.48 (d, J=10.4 Hz, 1H), 4.07 (dd, J=13.4, 6.9 Hz, 1H), 3.81-3.65 (m, 2H), 1.62 (s, 3H), 0.82-0.76 (m, 2H), 0.73-0.69 (m, 2H).

Example 19: N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-3,4-dicyclopropoxybenzamide

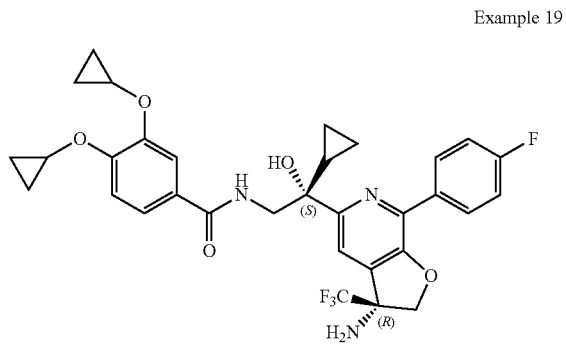

Example 19

Example 19 was prepared by a similar method as for Example 7. LC-MS, ES+ (m/z): 614.3 [M+H]+; 1H NMR (400 MHz, DMSO-d6) δ 8.23-8.12 (m, 3H), 7.61 (s, 1H), 7.49 (d, J=2.1 Hz, 1H), 7.28-7.16 (m, 3H), 7.11 (dd, J=8.4, 4.7 Hz, 1H), 5.65 (s, 1H), 4.77 (d, J=10.4 Hz, 1H), 4.38 (d, J=10.5 Hz, 1H), 3.90-3.61 (m, 3H), 2.96 (s, 2H), 1.44-1.36 (m, 1H), 1.24-1.11 (m, 1H), 0.70-0.58 (m, 4H), 0.58-0.48 (m, 4H), 0.47-0.38 (m, 1H), 0.31-0.24 (m, 1H), 0.21-0.11 (m, 1H), 0.04-0.06 (m, 1H).

Example 20: N—((S)-2-((R)-3-amino-7-(4-fluorophenyl)-3-(trifluoromethyl)-2,3-dihydrofuro[2,3-c]pyridin-5-yl)-2-hydroxypropyl)-3,4-dicyclopropoxybenzamide

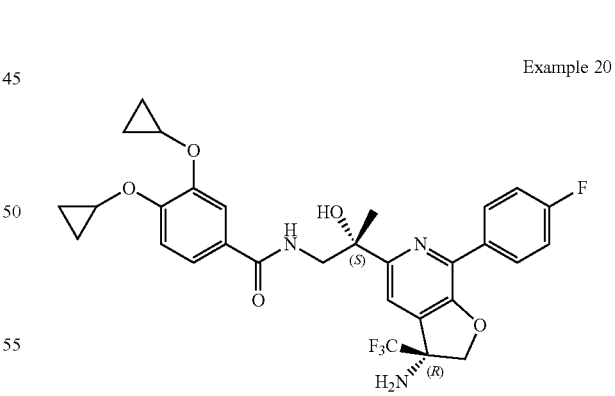

Example 20

Example 20 was prepared by a similar method as for Example 7. LC-MS, ES+ (m/z): 588.3[M+H]+; 1H NMR (400 MHz, DMSO-d6) δ 8.30-8.22 (m, 2H), 8.19 (t, J=5.7 Hz, 1H), 7.80 (s, 1H), 7.64 (d, J=2.0 Hz, 1H), 7.44-7.30 (m, 3H), 7.22 (dd, J=8.4, 4.9 Hz, 1H), 5.85 (s, 1H), 4.89 (d, J=10.4 Hz, 1H), 4.50 (d, J=10.4 Hz, 1H), 3.90-3.74 (m, 2H), 3.61 (dd, J=13.4, 5.9 Hz, 1H), 3.07 (s, 2H), 1.50 (d, J=3.3 Hz, 3H), 1.30 (t, J=7.3 Hz, 1H), 0.82-0.69 (m, 4H), 0.69-0.59 (m, 4H).

Example 21: N—((S)-2-((R)-3-(3-cyanoguanidino)-7-(4-fluorophenyl)-3-(trifluoromethyl)-2,3-dihydrofuro[2,3-c]pyridin-5-yl)-2-hydroxypropyl)-4-cyclopropoxy-3-methoxybenzamide

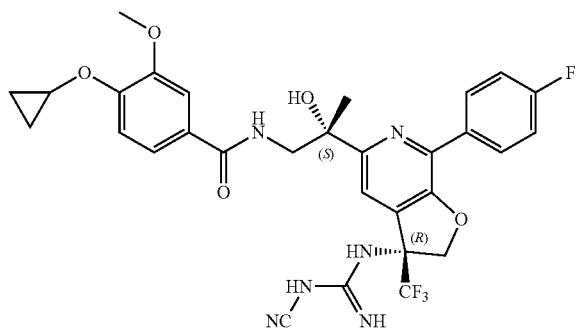

Example 21

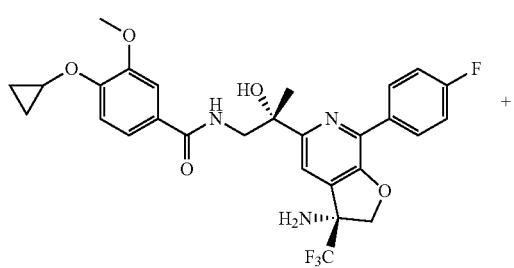

Example 7

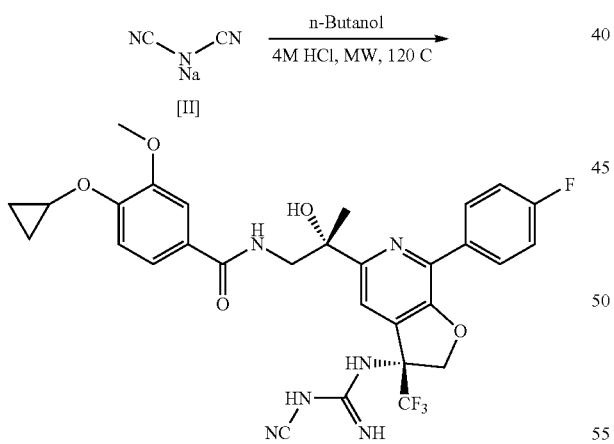

Example 21

A mixture of Example 7 (31 mg, 0.055 mmol), sodium dicyano amide (49.2 mg, 0.55 mmol), 4M HCl in dioxane (0.14 mL, 0.55 mmol) in n-butanol (0.55 mL) was heated under MW at 120° C. for 3 hrs. Then the mixture was quenched with sat. NaHCO$_3$, extracted with EtOAC (3×). The combined organic layers were washed with brine, dried over Na$_2$SO$_4$, and concentrated. Purification of the residue on silica gel with 0-10% MeOH/DCM provided Example 21 (3 mg, 9% yield). LC-MS, ES$^+$ (m/z): 629.2 [M+H]$^+$.

Example 22: N—((S)-2-((R)-3-amino-7-(3,4-difluorophenyl)-3-(trifluoromethyl)-2,3-dihydrofuro[2,3-c]pyridin-5-yl)-2-hydroxypropyl)-4-cyclopropoxy-3-methoxybenzamide

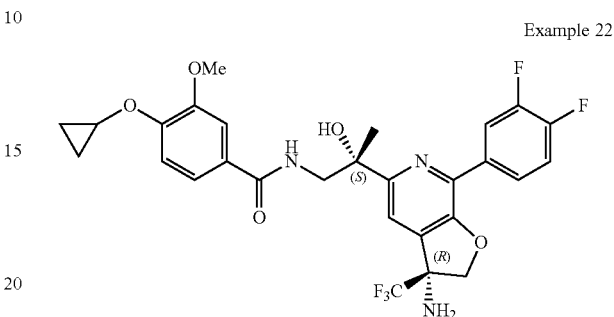

Example 22

Example 22 was prepared following similar procedures in Examples 1 and 7. LC-MS, ES$^+$ (m/z): [M+H]$^+$580.2; $^1$H NMR (400 MHz, DMSO-d$_6$) δ 8.30-8.13 (m, 2H), 8.13-8.01 (m, 1H), 7.83 (s, 1H), 7.58 (dt, J=10.6, 8.6 Hz, 1H), 7.46-7.30 (m, 2H), 7.22 (d, J=8.4 Hz, 1H), 5.87 (s, 1H), 4.92 (d, J=10.4 Hz, 1H), 4.52 (d, J=10.5 Hz, 1H), 3.86 (tt, J=6.1, 3.0 Hz, 1H), 3.82-3.69 (m, 4H), 3.69-3.60 (m, 1H), 1.51 (s, 3H), 0.86-0.72 (m, 2H), 0.66 (tq, J=5.3, 3.1 Hz, 2H).

Example 23: N—((S)-2-((R)-3-amino-7-(3,4-difluorophenyl)-3-(trifluoromethyl)-2,3-dihydrofuro[2,3-c]pyridin-5-yl)-2-cyclopropyl-2-hydroxyethyl)-4-cyclopropoxy-3-methoxybenzamide

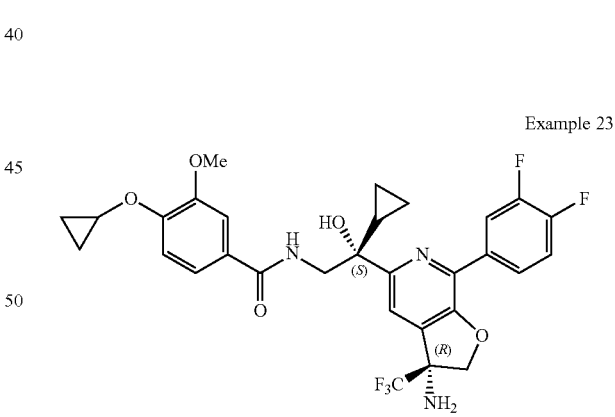

Example 23

Example 23 was prepared following similar procedures in Examples 1 and 7. LC-MS, ES$^+$ (m/z): [M+H]$^+$ 606.2; $^1$H NMR (400 MHz, DMSO-d$_6$) δ 8.22 (t, J=5.8 Hz, 1H), 8.10 (ddd, J=12.5, 8.2, 2.1 Hz, 1H), 7.99 (dd, J=9.3, 4.0 Hz, 1H), 7.64 (s, 1H), 7.47 (dt, J=10.4, 8.6 Hz, 1H), 7.26-7.16 (m, 2H), 7.11 (d, J=8.4 Hz, 1H), 5.68 (s, 1H), 4.79 (d, J=10.4 Hz, 1H), 4.40 (d, J=10.5 Hz, 1H), 3.85-3.68 (m, 3H), 3.61 (s, 3H), 1.41 (td, J=8.4, 4.3 Hz, 1H), 0.67 (dt, J=7.3, 5.7 Hz, 2H), 0.55 (q, J=3.4 Hz, 2H), 0.43 (dq, J=9.5, 5.0 Hz, 1H), 0.27 (dt, J=8.9, 4.5 Hz, 1H), 0.16 (dt, J=9.7, 4.7 Hz, 1H), 0.05--0.08 (m, 1H).

Example 24: N—((S)-2-((R)-3-amino-7-(3-chloro-4-fluorophenyl)-3-(trifluoromethyl)-2,3-dihydrofuro[2,3-c]pyridin-5-yl)-2-hydroxypropyl)-4-cyclopropoxy-3-methoxybenzamide

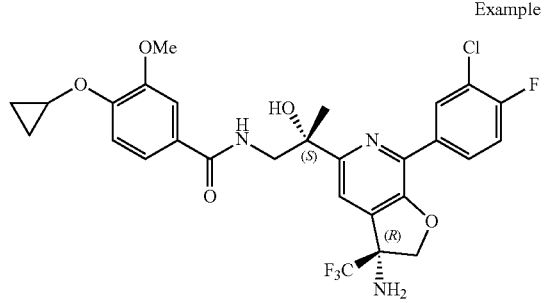

Example 24

Example 24 was prepared following similar procedures in Examples 1 and 7. LC-MS, ES+ (m/z): 596.2 [M+H]; $^1$H NMR (400 MHz, DMSO-$d_6$) δ 8.34 (ddd, J=7.4, 2.2, 0.9 Hz, 1H), 8.23 (dddd, J=11.1, 5.6, 2.8, 1.6 Hz, 2H), 7.84 (s, 1H), 7.62-7.52 (m, 1H), 7.42-7.29 (m, 2H), 7.22 (dd, J=8.4, 0.9 Hz, 1H), 5.87 (d, J=0.9 Hz, 1H), 4.93 (d, J=10.4 Hz, 1H), 4.52 (d, J=10.4 Hz, 1H), 3.86 (tt, J=5.9, 2.9 Hz, 1H), 3.81-3.71 (m, 4H), 3.64 (dd, J=13.4, 6.0 Hz, 1H), 3.08 (s, 2H), 1.51 (s, 3H), 0.84-0.70 (m, 2H), 0.74-0.62 (m, 2H).

Example 25: N—((S)-2-((R)-3-amino-7-(3-chloro-4-fluorophenyl)-3-(trifluoromethyl)-2,3-dihydrofuro[2,3-c]pyridin-5-yl)-2-cyclopropyl-2-hydroxyethyl)-4-cyclopropoxy-3-methoxybenzamide

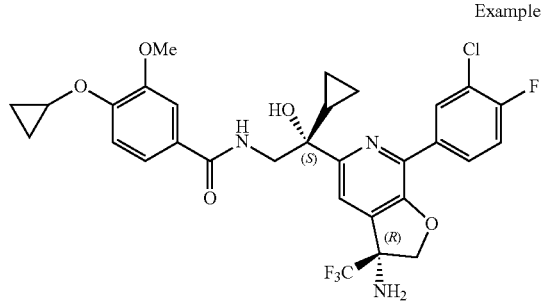

Example 25

Example 25 was prepared following similar procedures in Examples 1 and 7. LC-MS, ES+ (m/z): 622.3 [M+H]+; $^1$H NMR (400 MHz, DMSO-$d_6$) δ 8.29-8.19 (m, 2H), 8.14 (ddd, J=8.7, 4.8, 2.2 Hz, 1H), 7.64 (s, 1H), 7.46 (t, J=9.0 Hz, 1H), 7.26-7.17 (m, 2H), 7.11 (d, J=8.3 Hz, 1H), 5.68 (s, 1H), 4.80 (d, J=10.4 Hz, 1H), 4.40 (d, J=10.5 Hz, 1H), 3.80-3.70 (m, 3H), 3.61 (m, 1H), 2.97 (s, 2H), 1.41 (dd, J=13.7, 8.4, 5.3 Hz, 1H), 0.72-0.58 (m, 2H), 0.54 (dt, J=5.2, 2.9 Hz, 2H), 0.42 (dt, J=9.4, 4.7 Hz, 1H), 0.34-0.22 (m, 1H), 0.15 (dt, J=9.4, 4.6 Hz, 1H), 0.00 (m, 1H).

Example 26: N—((S)-2-((R)-3-amino-7-(3,4-difluorophenyl)-3-(trifluoromethyl)-2,3-dihydrofuro[2,3-c]pyridin-5-yl)-2-hydroxypropyl)-3,4-dicyclopropoxybenzamide

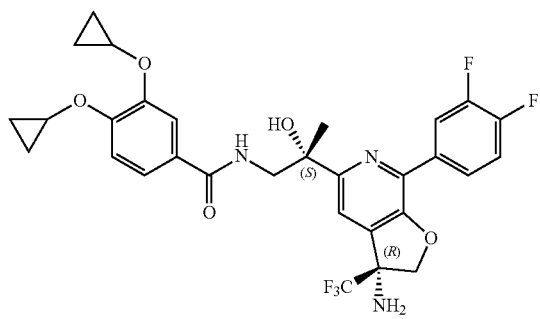

Example 26

Example 26 was prepared following similar procedures in Examples 1 and 7. LC-MS, ES+ (m/z): [M+H]+ 606.2; $^1$H NMR (400 MHz, DMSO-$d_6$) 8.18 (td, J=9.3, 7.9, 2.0 Hz, 2H), 8.09 (d, J=8.8 Hz, 1H), 7.84 (s, 1H), 7.66-7.51 (m, 2H), 7.45-7.33 (m, 1H), 7.22 (dd, J=8.4, 4.4 Hz, 1H), 5.92-5.85 (m, 1H), 4.92 (d, J=10.4 Hz, 1H), 4.52 (d, J=10.5 Hz, 1H), 3.89-3.61 (m, 4H), 1.51 (br s, 3H), 1.36-1.25 (m, 1H), 0.75 (m, 3H), 0.69-0.39 (m, 4H).

Example 27: N—((S)-2-((R)-3-amino-7-(3,4-difluorophenyl)-3-(trifluoromethyl)-2,3-dihydrofuro[2,3-c]pyridin-5-yl)-2-cyclopropyl-2-hydroxyethyl)-3,4-dicyclopropoxybenzamide

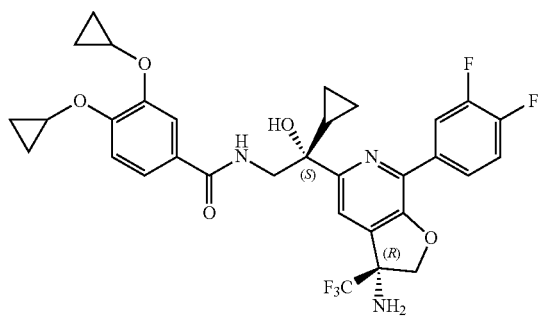

Example 27

Example 27 was prepared following similar procedures in Examples 1 and 7. LC-MS, ES+ (m/z): [M+H]+ 632.2; $^1$H NMR (400 MHz, DMSO-$d_6$) δ 8.18 (t, J=5.8 Hz, 1H), 8.10 (ddd, J=12.3, 8.1, 2.1 Hz, 1H), 7.99 (d, J=8.6 Hz, 1H), 7.64 (s, 1H), 7.56-7.37 (m, 2H), 7.22 (dd, J=8.5, 2.1 Hz, 1H), 7.11 (dd, J=8.4, 4.1 Hz, 1H), 5.64 (d, J=20.2 Hz, 1H), 4.79 (d, J=10.4 Hz, 1H), 4.40 (d, J=10.4 Hz, 1H), 3.97-3.52 (m, 4H), 1.39 (td, J=8.2, 4.1 Hz, 1H), 1.24-1.00 (m, 2H), 0.72-0.58 (m, 3H), 0.58-0.47 (m, 3H), 0.44 (m, 1H), 0.27 (m, 1H), 0.23-0.09 (m, 1H), −0.01 (m, 1H).

Example 28: N—((S)-2-((R)-3-amino-7-(3-chloro-4-fluorophenyl)-3-(trifluoromethyl)-2,3-dihydrofuro[2,3-c]pyridin-5-yl)-2-hydroxypropyl)-3,4-dicyclopropoxybenzamide

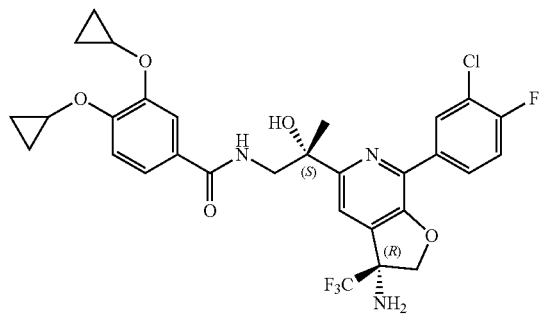

Example 28

Example 28 was prepared following similar procedures in Examples 1 and 7. LC-MS, ES⁺ (m/z): 622.3 [M+H]⁺; 1H NMR (400 MHz, Chloroform-d) δ 8.27 (dd, J=7.2, 2.2 Hz, 1H), 8.12 (ddd, J=8.8, 4.7, 2.2 Hz, 1H), 7.53 (d, J=1.7 Hz, 1H), 7.22 (d, J=8.7 Hz, 1H), 7.16-7.03 (m, 2H), 6.49 (brs, 1H), 5.47 (brs, 1H), 4.92 (d, J=10.4 Hz, 1H), 4.49 (d, J=10.5 Hz, 1H), 4.04 (dt, J=12.7, 6.4 Hz, 1H), 3.80-3.59 (m, 3H), 1.63 (s, 3H), 1.41 (dt, J=13.4, 7.0 Hz, 1H), 0.90-0.65 (m, 7H).

Example 29: N—((S)-2-((R)-3-amino-7-(3-chloro-4-fluorophenyl)-3-(trifluoromethyl)-2,3-dihydrofuro[2,3-c]pyridin-5-yl)-2-hydroxypropyl)-3,4-dicyclopropoxybenzamide

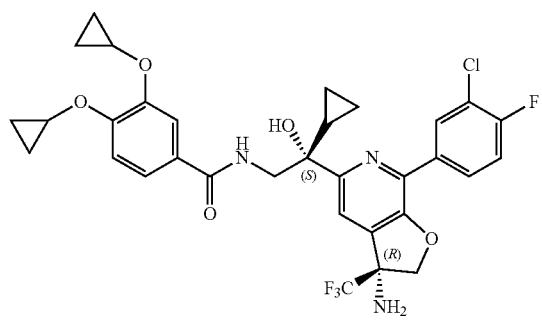

Example 29

Example 29 was prepared following similar procedures in Examples 1 and 7. LC-MS, ES⁺ (m/z): 648.3 [M+H]⁺; 1H NMR (400 MHz, Chloroform-d) δ 8.25 (d, J=7.0 Hz, 1H), 8.10 (d, J=8.9 Hz, 1H), 7.69 (s, 1H), 7.50 (d, J=2.0 Hz, 1H), 7.24-7.17 (m, 1H), 7.17-7.01 (m, 2H), 6.45 (s, 1H), 4.92 (d, J=10.4 Hz, 1H), 4.48 (d, J=10.5 Hz, 1H), 4.37-4.22 (m, 1H), 3.80-3.58 (m, 3H), 1.40 (dt, J=14.0, 6.9 Hz, 1H), 1.34-1.30 (m, 1H), 0.87-0.61 (m, 8H), 0.60-0.45 (m, 1H), 0.37 (dt, J=10.0, 5.0 Hz, 1H), 0.32-0.21 (m, 1H).

Example 30: N—((S)-2-((R)-3-amino-7-(3-chloro-4-fluorophenyl)-3-(trifluoromethyl)-2,3-dihydrofuro[2,3-c]pyridin-5-yl)-2-cyclopropyl-2-hydroxyethyl)-8-cyclopropoxyquinoline-6-carboxamide Example 30

Example 30 was prepared following similar procedures in Examples 1 and 7. LC-MS, ES⁺ (m/z): 643.2 [M+H]⁺; 1H NMR (400 MHz, Chloroform-d) δ 8.91 (s, 1H), 8.24 (dd, J=7.2, 1.9 Hz, 1H), 8.09 (ddd, J=9.0, 4.6, 2.0 Hz, 1H), 7.99 (d, J=7.8 Hz, 1H), 7.67 (d, J=16.3 Hz, 2H), 7.50 (s, 1H), 7.41 (d, J=8.2 Hz, 1H), 7.19 (t, J=8.6 Hz, 1H), 6.73 (s, 1H), 5.26 (d, J=23.6 Hz, 1H), 4.91 (d, J=10.1 Hz, 1H), 4.47 (d, J=10.2 Hz, 1H), 4.38 (dd, J=13.8, 7.2 Hz, 1H), 3.89-3.74 (m, 2H), 2.07 (s, 2H), 1.42-1.29 (m, 1H), 0.93 (d, J=10.9 Hz, 2H), 0.91-0.80 (m, 2H), 0.80-0.66 (m, 1H), 0.57 (q, J=7.6, 5.7 Hz, 1H), 0.50-0.37 (m, 1H), 0.31 (p, J=4.8 Hz, 1H).

The following examples were prepared by using procedures similar to those described above:

| Entry | Example | LC-MS observed [M + 1] |
|---|---|---|
| 31 | (structure) | 620.3 |

-continued

| Entry | Example | LC-MS observed [M + 1] |
|---|---|---|
| 32 | | 620.4 |
| 33 | | 620.3 |
| 34 | | 590.3 |
| 35 | | 591.4 |

| Entry | Example | LC-MS observed [M + 1] |
|---|---|---|
| 36 | | 632.4 |
| 37 | | 634.4 |
| 38 | | 608.3 |
| 39 | | 634.3 |
| 40 | | 611.4 |

-continued

| Entry | Example | LC-MS observed [M + 1] |
|---|---|---|
| 41 | | 611.4 |
| 42 | | 628.4 |
| 43 | | 641.4 |
| 44 | | 674.3 |

-continued

| Entry | Example | LC-MS observed [M + 1] |
|---|---|---|
| 45 | | 703.4 |
| 46 | | 677.3 |
| 47 | | 548.3 |
| 48 | | 564.2 |

Example 49: N—((S)-2-((R)-3-amino-7-(4-fluorophenyl)-3-(trifluoromethyl)-2,3-dihydrofuro[2,3-c]pyridin-5-yl)-2-hydroxy-3-methoxypropyl)-4-cyclopropoxy-3-methoxybenzamide

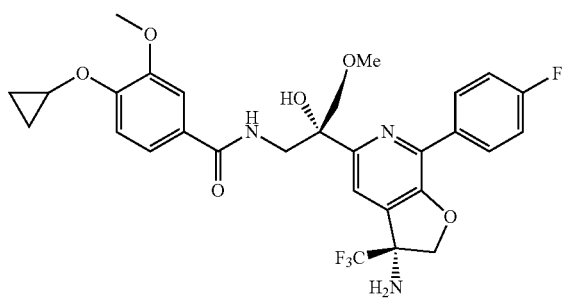

Example 49

Example 49 was prepared following similar procedures in Examples 1 and 7. LC-MS, ES+ (m/z): 592.4 [M+H]+; 1H NMR (400 MHz, Chloroform-d) δ 8.20 (dd, J=8.7, 5.5 Hz, 2H), 7.71 (s, 1H), 7.26-7.23 (m, 1H), 7.22-7.02 (m, 4H), 6.64 (s, 1H), 4.91 (d, J=10.3 Hz, 1H), 4.47 (d, J=10.4 Hz, 1H), 4.22-4.07 (m, 1H), 3.81 (s, 4H), 3.79-3.70 (m, 2H), 3.68 (d, J=9.5 Hz, 1H), 3.38 (s, 3H), 0.93-0.66 (m, 4H).

Example 50: N—((S)-2-((R)-3-amino-7-(4-fluorophenyl)-3-(trifluoromethyl)-2,3-dihydrofuro[2,3-c]pyridin-5-yl)-2-hydroxy-3-methoxypropyl)-8-cyclopropoxyquinoline-6-carboxamide

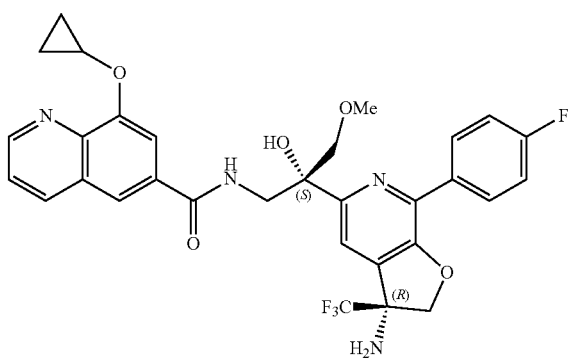

Example 50

Example 50 was prepared following similar procedures in Examples 1 and 7. LC-MS, ES+ (m/z): 613.1 [M+H]+; 1H NMR (400 MHz, Chloroform-d) δ 8.94 (dd, J=4.3, 1.7 Hz, 1H), 8.29-8.12 (m, 2H), 7.94 (dd, J=8.4, 1.7 Hz, 1H), 7.78-7.66 (m, 2H), 7.51 (d, J=1.8 Hz, 1H), 7.42 (dd, J=8.3, 4.2 Hz, 1H), 7.13 (t, J=8.7 Hz, 2H), 6.84 (dd, J=7.5, 4.3 Hz, 1H), 5.09 (s, 1H), 4.90 (d, J=10.4 Hz, 1H), 4.46 (d, J=10.4 Hz, 1H), 4.25 (dd, J=13.8, 7.4 Hz, 1H), 3.88 (dt, J=11.0, 4.3 Hz, 2H), 3.82-3.75 (m, 1H), 3.72 (d, J=9.5 Hz, 1H), 3.41 (s, 3H), 0.97 (dt, J=5.0, 3.0 Hz, 2H), 0.87 (dd, J=6.8, 4.0 Hz, 2H).

Example 51: N—((S)-2-((R)-3-amino-7-(4-fluorophenyl)-3-(trifluoromethyl)-2,3-dihydrofuro[2,3-c]pyridin-5-yl)-2,3-dihydroxypropyl)-4-cyclopropoxy-3-methoxybenzamide

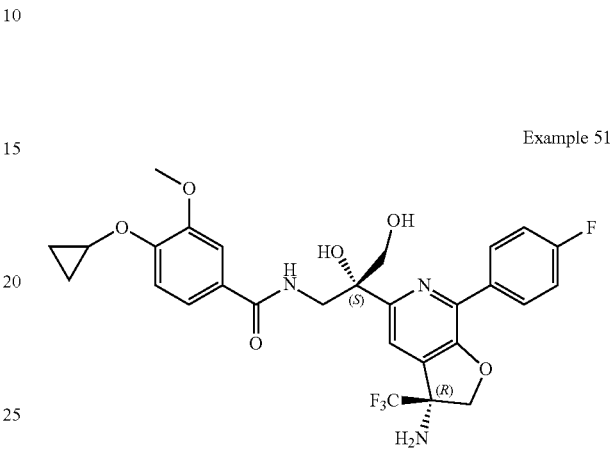

Example 51

Example 51 was prepared following similar procedures in Examples 1 and 7. LC-MS, ES+ (m/z): 578.1[M+H]+; 1H NMR (400 MHz, Chloroform-d) δ 8.19-8.09 (m, 2H), 7.83 (s, 1H), 7.38 (d, J=2.0 Hz, 1H), 7.27-7.20 (m, 2H), 7.20-7.12 (m, 2H), 6.95 (t, J=6.4 Hz, 1H), 4.95 (d, J=10.3 Hz, 1H), 4.51 (dt, J=10.4, 1.5 Hz, 1H), 3.93 (t, J=6.1 Hz, 2H), 3.88 (s, 3H), 3.86 (d, J=11.7 Hz, 1H), 3.81 (tt, J=6.0, 3.0 Hz, 1H), 3.73 (d, J=11.7 Hz, 1H), 0.95-0.80 (m, 4H).

Example 52: 2-amino-N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)benzo[d]thiazole-6-carboxamide

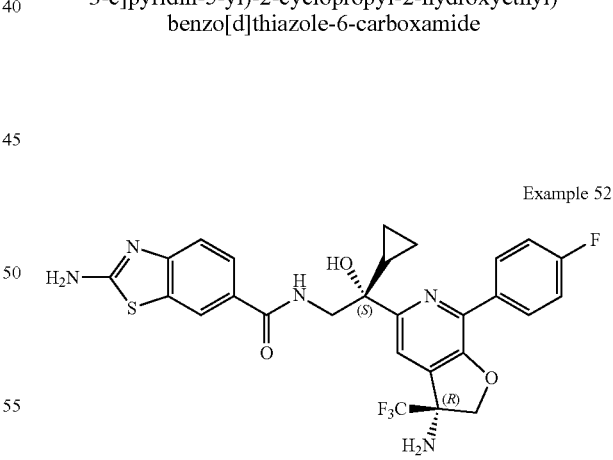

Example 52

Example 52 was prepared following similar procedures in Examples 1 and 7. LC-MS, ES+ (m/z): 574.3 [M+H]+; 1H NMR (400 MHz, DMSO-d6) δ 8.21-8.10 (m, 3H), 8.02 (brs, 1H), 7.85 (d, J=1.8 Hz, 1H), 7.62 (d, J=8.1 Hz, 2H), 7.46 (dd, J=8.4, 1.9 Hz, 1H), 7.28-7.15 (m, 2H), 7.14 (d, J=10.0 Hz, 1H), 5.58 (s, 1H), 4.76 (d, J=10.4 Hz, 1H), 4.38 (d, J=10.5 Hz, 1H), 3.77 (d, J=5.7 Hz, 1H), 3.64-3.52 (m, 1H), 3.43-3.31 (m, 1H), 2.95 (s, 2H), 1.44 (brs, 1H), 0.48-0.40 (m, 1H), 0.32-0.13 (m, 1H), 0.00 (m, 1H).

Example 53: 2-amino-N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-4-methoxybenzo[d]thiazole-6-carboxamide

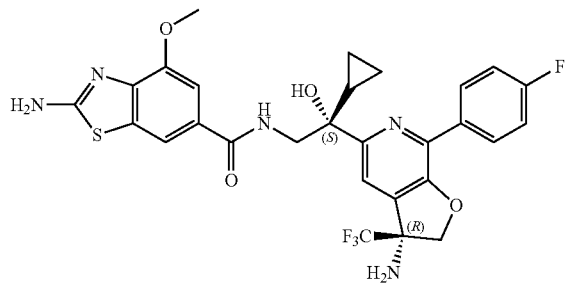

Example 53

Example 53 was prepared following similar procedures in Examples 1 and 7. LC-MS, ES+ (m/z): 604.3[M+H]+; 1H NMR (400 MHz, DMSO-d6) δ 8.17 (dt, J=8.8, 5.8 Hz, 3H), 7.61 (s, 1H), 7.55 (s, 2H), 7.48 (d, J=1.5 Hz, 1H), 7.26-7.17 (m, 2H), 7.07 (d, J=1.5 Hz, 1H), 5.61 (s, 1H), 4.76 (d, J=10.4 Hz, 1H), 4.37 (d, J=10.5 Hz, 1H), 3.77 (d, J=5.4 Hz, 2H), 3.70 (s, 3H), 3.36 (q, J=6.4, 4.8 Hz, 1H), 2.96 (s, 2H), 1.44 (m, 1H), 0.47-0.39 (m, 1H), 0.27 (m, 1H), 0.20-0.12 (m, 1H), 0.00 (m, 1H).

Example 54: 2-amino-N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-4-fluorobenzo[d]thiazole-6-carboxamide

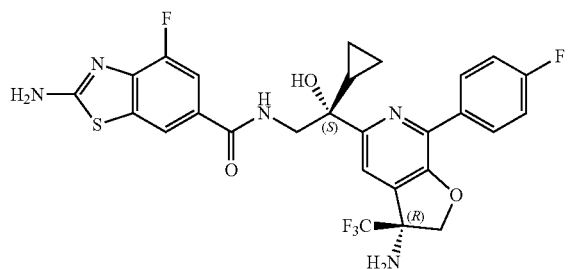

Example 54

Example 54 was prepared following similar procedures in Examples 1 and 7. LC-MS, ES+ (m/z): 592.2 [M+H]+; 1H NMR (400 MHz, DMSO-d6) δ 8.15 (dd, J=8.9, 5.7 Hz, 3H), 7.86 (s, 2H), 7.71 (d, J=1.5 Hz, 1H), 7.59 (s, 1H), 7.31-7.17 (m, 3H), 7.21 (s, 1H), 5.43 (s, 1H), 4.75 (d, J=10.4 Hz, 1H), 4.37 (d, J=10.5 Hz, 1H), 3.76 (d, J=6.0 Hz, 2H), 2.94 (s, 2H), 1.44 (m, 1H), 0.43 (m, 1H), 0.26 (m, 1H), 0.17 (m, 1H), 0.00 (m, 1H).

Example 55: N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-7-methoxy-2-methyl-2H-indazole-5-carboxamide

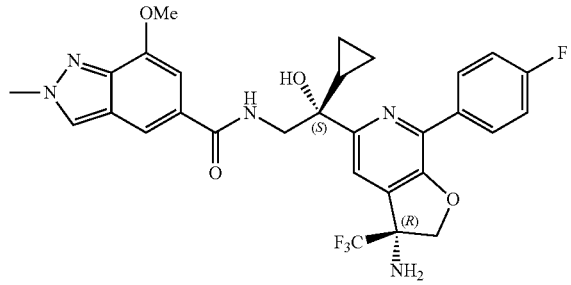

Example 55

Example 55 was prepared following similar procedures in Examples 1 and 7. LC-MS, ES+ (m/z): 586.4 [M+H]+; 1H NMR (400 MHz, Chloroform-d) δ 8.23-8.12 (m, 2H), 7.76 (s, 1H), 7.64 (s, 1H), 7.34 (s, 1H), 7.19-7.07 (m, 2H), 6.76 (s, 1H), 6.52 (br s, 1H), 5.29 (br s, 1H), 4.89 (d, J=10.3 Hz, 1H), 4.44 (dt, J=10.5, 1.5 Hz, 1H), 4.33 (dd, J=13.9, 7.9 Hz, 1H), 4.17 (s, 3H), 3.93 (s, 3H), 3.75 (dd, J=13.9, 4.2 Hz, 1H), 2.04 (br s, 2H), 1.36-1.26 (m, 1H), 0.74-0.63 (m, 1H), 0.57-0.50 (m, 1H), 0.42-0.36 (m, 1H), 0.34-0.22 (m, 1H).

Example 66: N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-7-cyclopropoxy-2-methyl-2H-indazole-5-carboxamide

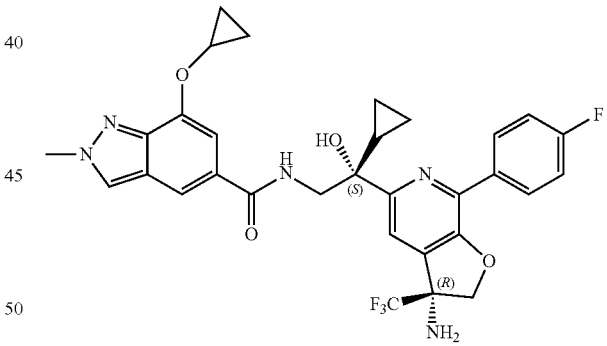

Example 66

Step 1-6: Synthesis of 7-cyclopropoxy-2-methyl-2H-indazole-5-carboxylic acid (66-7)

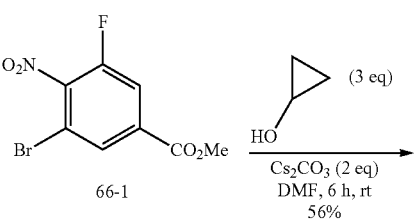

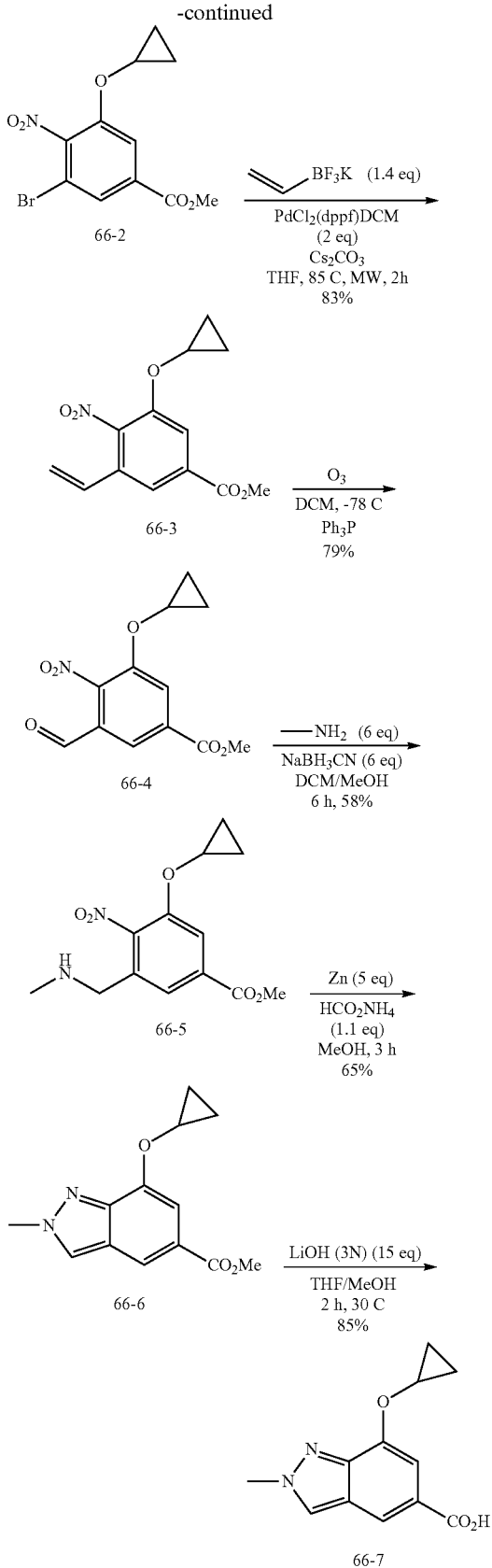

Step 1: A mixture of methyl 3-bromo-5-fluoro-4-nitrobenzoate (66-1) (3 g, 10.79 mmol), cyclopropanol (1.367 mL, 21.58 mmol), and cesium carbonate (5.27 g, 16.19 mmol) was stirred at rt for 3 hrs, LC-MS showed that the conversion was still not complete. More cyclopropanol (1.0 eq) and cesium carbonate (0.5 eq) were added, and the mixture stirred for another 3 hrs, LC-MS showed complete conversion. The mixture was then diluted with ethyl acetate, washed with water and brine, and the organic layers were dried over $Na_2SO_4$ and concentrated. The residue was purified by chromatography on silica gel using cyclohexane/ethyl acetate (100/0 to 50/30, 10 min) to give a light yellow solid, which was washed with cyclohexane to yield the desired product 66-2 as a white solid (1.9 g, 56%). $^1$H NMR (400 MHz, DMSO-$d_6$) δ 8.03 (d, J=1.5 Hz, 1H), 7.92 (d, J=1.5 Hz, 1H), 4.28 (tt, J=6.0, 2.8 Hz, 1H), 3.93 (s, 3H), 0.92-0.79 (m, 2H), 0.74 (dh, J=5.5, 3.1, 2.6 Hz, 2H).

Step 2: A mixture of 66-2 (600 mg, 1.898 mmol), trifluoro(vinyl)-14-borane, potassium salt (381 mg, 2.85 mmol), $PdCl_2$(dppf)-$CH_2Cl_2$ adduct (310 mg, 0.380 mmol), and cesium carbonate (1237 mg, 3.80 mmol) in THE (12 mL) was degassed with nitrogen and then heated to 85° C. in the MW for 2 hrs, diluted with water, and extracted with ethyl acetate. The combined organic layers were washed with brine, dried over $Na_2SO_4$ and concentrated. The residue was purified by chromatography on silica gel using cyclohexane/ethyl acetate (100/0 to 50/30, 10 min) to give product 66-3 as a pale yellow solid (415 mg, 83%). $^1$H NMR (400 MHz, DMSO-$d_6$) δ 7.94 (dd, J=9.6, 1.5 Hz, 2H), 6.54 (dd, J=17.3, 11.1 Hz, 1H), 6.10 (d, J=17.3 Hz, 1H), 5.64 (d, J=11.1 Hz, 1H), 4.22 (tt, J=6.0, 2.9 Hz, 1H), 3.93 (s, 3H), 0.91-0.78 (m, 2H), 0.72 (dh, J=5.5, 3.0 Hz, 2H).

Step 3: A solution of 66-3 (830 mg, 3.15 mmol in DCM (31 mL) was cooled to −78° C. and treated with ozone (bubbling through pipette, bigger hole) for ~5-10 min, TLC (cyclohexane/ethyl acetate: 3/1) showed no olefin 66-3. Excess ozone was removed by blowing $O_2$, followed by $N_2$. The reaction was then quenched with triphenylphosphine (2481 mg, 9.46 mmol) and warmed to rt, and stirred for 1 h. After the solvent was removed by a rotovap, the residue was purified by chromatography on 40 g silica gel using cyclohexane/ethyl acetate (100/0 to 60/40, 20 min) to give product 66-4 as a pale yellow solid (662 mg, 79%). $^1$H NMR (400 MHz, Chloroform-d) δ 9.95 (s, 1H), 8.32 (s, 1H), 8.18 (d, J=1.5 Hz, 1H), 4.02 (bs, 4H), 0.99-0.83 (m, 4H).

Step 4: A solution of methyl 66-4 (100 mg, 0.377 mmol) and methanamine in THE (1131 μl, 2.262 mmol) in DCM (7 mL) was stirred at rt for 30 min, and then sodium cyanoborohydride (142 mg, 2.262 mmol) was added. The mixture was stirred at rt for 2 h, LC-MS showed partial conversion, more methanamine in THE (1.13 mL, 2.262 mmol) and sodium cyanoborohydride (142 mg, 2.262 mmol) were added, and the mixture was stirred for another 4 h. It was then diluted with DCM and washed with sat. $NaHCO_3$. The organic layers were dried over $Na_2SO_4$ and concentrated. The residue was purified by chromatography on silica gel using cyclohexane/ethyl acetate (100/0 to 10/90, 10 min) to give the desired product 66-5 as a pale yellow oil (61 mg, 58%). LC-MS, $ES^+$ (m/z): 280.9 $[M+H]^+$.

Step 5: To a solution of 66-5 (150 mg, 0.535 mmol) in MeOH (10 mL) was added zinc (175 mg, 2.68 mmol), followed by dropwise addition of ammonium formate (37.1 mg, 0.589 mmol) in MeOH (0.5 mL). The reaction mixture was stirred at rt for 3 h, filtered through a pad of Celite and washed with MeOH. The filtrate was concentrated and the residue was purified by chromatography on silica gel using cyclohexane/ethyl acetate (100/0 to 50/50, 10 min) to give the desired product 66-6 (102 mg, 77%) as a pale yellow solid. LC-MS, $ES^+$ (m/z): 247.0 $[M+H]^+$.

Step 6: To a solution of 66-6 (15 mg, 0.061 mmol) in THF (1 mL)/MeOH (1 mL) was added LiOH (609 µL, 1.827 mmol). The mixture was stirred at rt for 2 h. After removing the solvent, the residue was acidified to pH 2 with 1 N HCl. The precipitates was extracted into ethyl acetate. The combined organic layers were washed with brine, dried over $Na_2SO_4$ and concentrated, and dried under high vacuum to give the desired product 66-7 (12 mg, 85%) as a pale yellow solid. LC-MS, $ES^+$ (m/z): 232.9 $[M+H]^+$.

Example 66 was prepared from 66-7 following similar procedures in Examples 1 and 7. LC-MS, $ES^+$ (m/z): 638.2 $[M+H]^+$; $^1H$ NMR (400 MHz, Chloroform-d) δ 8.21 (ddd, J=8.5, 5.4, 2.6 Hz, 2H), 7.80 (s, 1H), 7.69 (s, 1H), 7.42 (d, J=1.3 Hz, 1H), 7.22-7.10 (m, 3H), 6.56 (s, 1H), 5.35 (s, 1H), 4.91 (d, J=10.4 Hz, 1H), 4.51-4.43 (m, 1H), 4.36 (dd, J=13.9, 8.0 Hz, 1H), 4.20 (s, 3H), 3.89-3.74 (m, 2H), 2.19 (s, 2H), 1.40-1.26 (m, 1H), 0.90 (dtt, J=7.2, 5.1, 2.6 Hz, 2H), 0.88-0.77 (m, 1H), 0.81-0.73 (m, 1H), 0.72 (dt, J=9.8, 4.9 Hz, 1H), 0.63-0.52 (m, 1H), 0.42 (dq, J=9.9, 5.2 Hz, 1H), 0.37-0.26 (m, 1H).

Example 55c: N—((S)-2-((R)-3-amino-7-(4-fluorophenyl)-3-(trifluoromethyl)-2,3-dihydrofuro[2,3-c]pyridin-5-yl)-2-cyclopropyl-2-hydroxyethyl)-7-cyclopropoxy-2-cyclopropyl-2H-indazole-5-carboxamide Example 55c

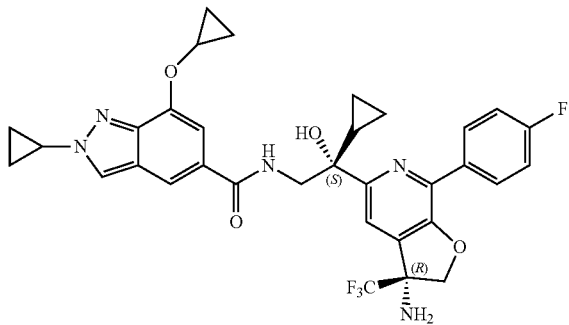

Step 1-2: Synthesis of 7-cyclopropoxy-2-cyclopropyl-2H-indazole-5-carboxylic acid (55c-2)

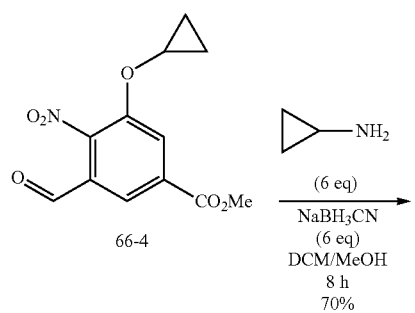

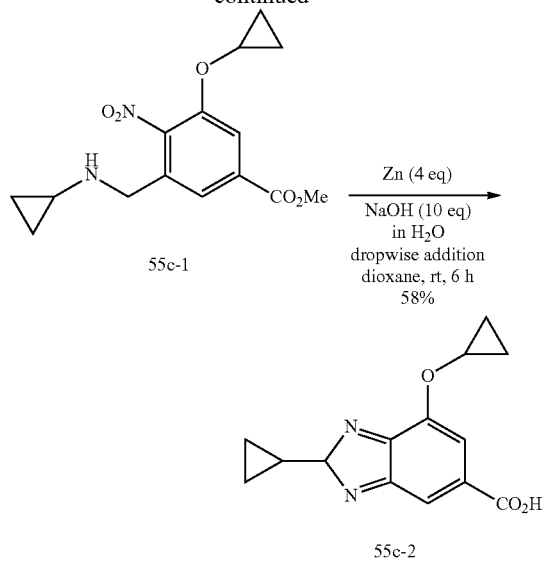

Step 1: A solution of 66-4 (200 mg, 0.754 mmol) and cyclopropanamine (157 µL, 2.262 mmol) in DCM (3.75 mL) was stirred at rt for 6-8 hrs. MeOH (3.75 mL) and HOAC (0.26 mL, 4.52 mmol) were then added followed by addition of sodium cyanoborohydride (142 mg, 2.262 mmol). The mixture was stirred at rt o/n until LC-MS showed complete reaction. The solvents were then removed. The residue was diluted with ethyl acetate, and washed with sat. $NaHCO_3$. The organic layer was dried over $Na_2SO_4$ and concentrated. The residue was purified by chromatography on silica gel using cyclohexane/ethyl acetate (100/0 to 40/60, 20 min) to give the desired product 55c-1 as a colorless solid (161 mg, 70%). LC-MS, $ES^+$ (m/z): 307.1 $[M+H]^+$; $^1H$ NMR (400 MHz, DMSO-$d_6$) δ 7.77 (t, J=1.3 Hz, 1H), 7.64 (t, J=1.2 Hz, 1H), 4.03 (ddd, J=6.1, 4.3, 1.9 Hz, 1H), 3.76 (d, J=1.0 Hz, 3H), 3.58 (s, 2H), 2.74 (s, 1H), 1.86-1.79 (m, 1H), 1.02 (td, J=7.2, 1.0 Hz, 1H), 0.74-0.61 (m, 2H), 0.54 (s, 2H), 0.19-0.06 (m, 2H), 0.02-0.00 (m, 2H).

Step 2: To a solution of 55c-1 (57 mg, 0.186 mmol) in 1,4-dioxane (1 mL) was added zinc (48.7 mg, 0.744 mmol), followed by the dropwise addition of sodium hydroxide (74.4 mg, 1.861 mmol) in water (1 mL). The reaction mixture was stirred at rt for 6 h, LC-MS showed a complete conversion. The precipitates was filtered out, and the filtrate was concentrated under vacuum. The residue was acidified with 3M HCl to pH 2, and the crude product was extracted into ethyl acetate. The combine organic layers were dried over $Na_2SO_4$ and concentrated. The residue was purified by chromatography on silica gel using DCM/methanol (100/0 to 90/10, 10 min) to give the desired product 55c-2 as a white solid (28 mg, 58%). LC-MS, $ES^+$ (m/z): 259.0 $[M+H]^+$; $^1H$ NMR (400 MHz, DMSO-$d_6$) δ 12.70 (s, 1H), 8.64 (d, J=7.8 Hz, 1H), 8.01 (s, 1H), 7.40 (d, J=8.6 Hz, 1H), 4.14 (s, 1H), 4.01 (s, 1H), 1.29-1.24 (m, 2H), 1.12 (d, J=7.5 Hz, 2H), 0.86 (s, 2H), 0.77 (s, 2H).

Example 55c was prepared from 55c-2 following similar procedures in Examples 1 and 7. LC-MS, $ES^+$ (m/z): 638.2 [M+H]; $^1H$ NMR (400 MHz, DMSO-$d_6$) δ 8.39 (s, 1H), 8.22 (t, J=5.8 Hz, 1H), 8.20-8.12 (m, 2H), 7.61 (s, 1H), 7.55 (d, J=1.3 Hz, 1H), 7.22 (t, J=8.9 Hz, 2H), 7.10 (d, J=1.3 Hz, 1H), 5.66 (s, 1H), 4.75 (d, J=10.4 Hz, 1H), 4.37 (d, J=10.5 Hz, 1H), 4.00 (tt, J=7.7, 3.9 Hz, 1H), 3.85-3.71 (m, 3H), 2.95 (s, 2H), 1.41 (td, J=8.3, 4.3 Hz, 1H), 1.17-1.06 (m, 2H), 1.06-0.93 (m, 2H), 0.68 (t, J=5.8 Hz, 2H), 0.60 (s, 2H), 0.48-0.40 (m, 1H), 0.28 (s, 1H), 0.17 (dt, J=10.0, 4.8 Hz, 1H), 0.03-0.00 (m, 1H).

Example 55d: N—((S)-2-((R)-3-amino-7-(3-chloro-4-fluorophenyl)-3-(trifluoromethyl)-2,3-dihydrofuro[2,3-c]pyridin-5-yl)-2-cyclopropyl-2-hydroxyethyl)-7-cyclopropoxy-2-cyclopropyl-2H-indazole-5-carboxamide Example 55d

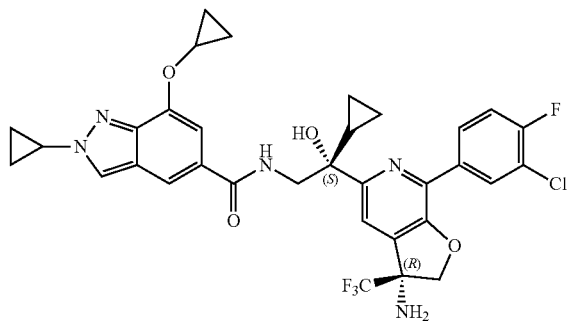

Example 55d was prepared following similar procedures in Examples 1 and 7. LC-MS, ES+ (m/z): 672.2 [M+H]+; 1H NMR (500 MHz, DMSO-$d_6$) δ 8.39 (s, 1H), 8.29-8.19 (m, 2H), 8.14 (ddd, J=8.8, 4.8, 2.2 Hz, 1H), 7.65 (s, 1H), 7.53 (d, J=1.3 Hz, 1H), 7.45 (t, J=9.0 Hz, 1H), 7.09 (d, J=1.3 Hz, 1H), 5.68 (s, 1H), 4.78 (d, J=10.4 Hz, 1H), 4.40 (d, J=10.4 Hz, 1H), 3.99 (tt, J=7.5, 3.8 Hz, 1H), 3.85-3.74 (m, 3H), 2.97 (s, 2H), 1.40 (ddd, J=13.7, 8.4, 5.3 Hz, 1H), 1.16-1.09 (m, 2H), 1.05-0.94 (m, 2H), 0.68 (dd, J=6.2, 2.3 Hz, 2H), 0.68-0.56 (m, 2H), 0.44 (dt, J=9.5, 4.7 Hz, 1H), 0.28 (dt, J=8.9, 4.4 Hz, 1H), 0.16 (dq, J=9.5, 5.4 Hz, 1H), 0.00 (m 1H).

The following examples were prepared by using procedures similar to those described above:

| Entry | Example | LC-MS observed [M + 1] |
|---|---|---|
| 56 | | 617.2 |
| 57 | | 604.1 |
| 58 | | 625.1 |

-continued
| Entry | Example | LC-MS observed [M + 1] |
|---|---|---|
| 59 | 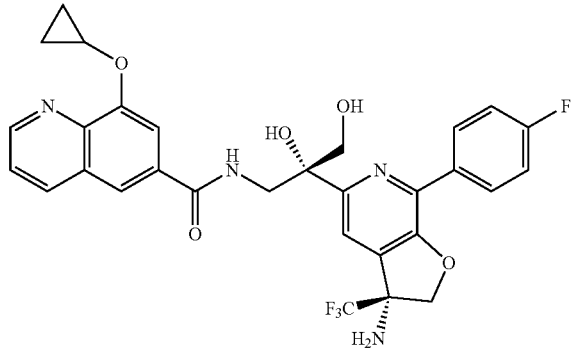 [SMILES: N[C@@]1(C(F)(F)F)COc2c1cc([C@](O)(CO)CNC(=O)c1cc(OC3CC3)c3ncccc3c1)nc2-c1ccc(F)cc1] | 599.1 |
| 59b | 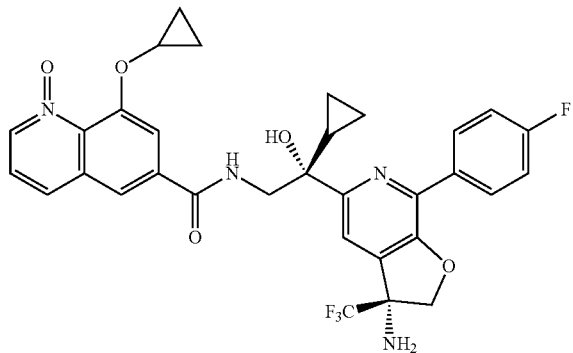 [SMILES: N[C@@]1(C(F)(F)F)COc2c1cc([C@@](O)(CNC(=O)c1cc(OC3CC3)c3c(ccc[n+]3[O-])c1)C1CC1)nc2-c1ccc(F)cc1] | 625.1 |
| 59c | 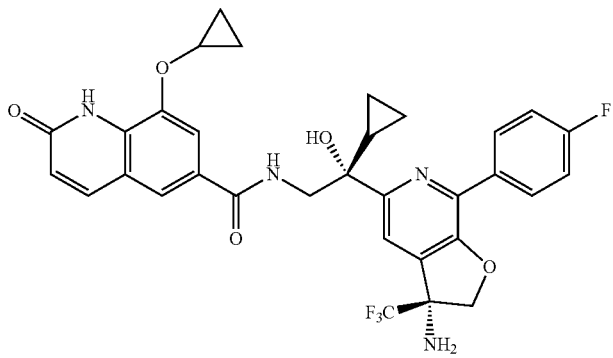 [SMILES: N[C@@]1(C(F)(F)F)COc2c1cc([C@@](O)(CNC(=O)c1cc(OC3CC3)c3[nH]c(=O)ccc3c1)C1CC1)nc2-c1ccc(F)cc1] | 625.0 |
| 59d | 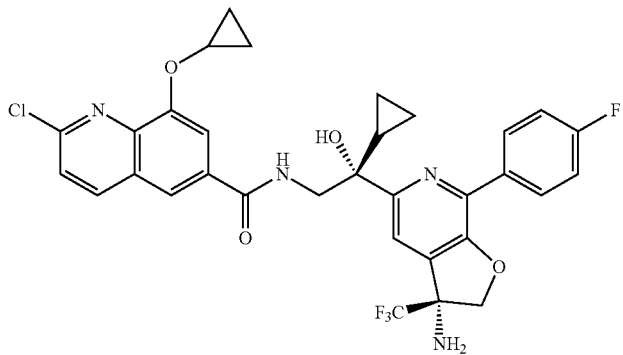 [SMILES: N[C@@]1(C(F)(F)F)COc2c1cc([C@@](O)(CNC(=O)c1cc(OC3CC3)c3nc(Cl)ccc3c1)C1CC1)nc2-c1ccc(F)cc1] | 643.1 |

| Entry | Example | LC-MS observed [M + 1] |
|---|---|---|
| 59e | | 623.0 |
| 64 | | 574.3 |

The following examples can be prepared by using procedures similar to those described above:

| Entry | Example |
|---|---|
| 60 | |
| 61 | |

| Entry | Example |
|---|---|
| 62 | 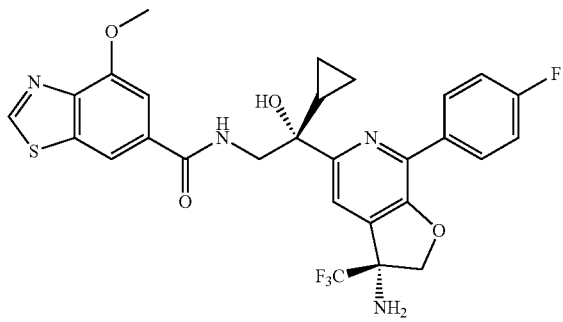 |
| 63 | 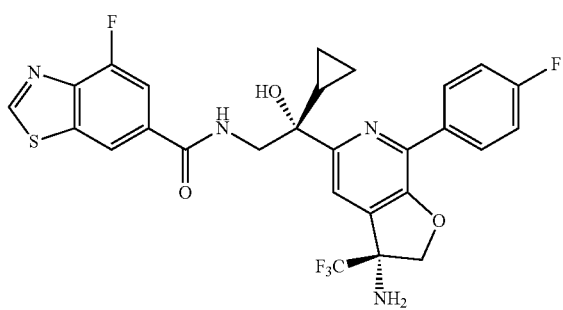 |
| 65 | 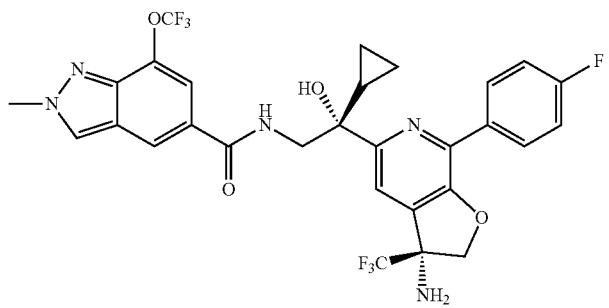 |
| 67 | 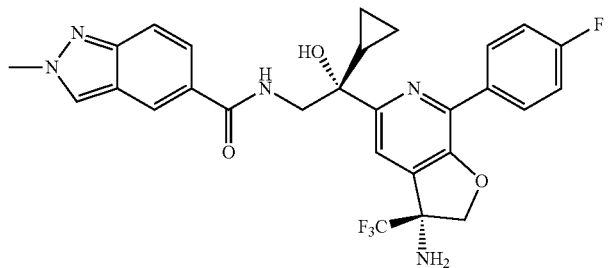 |
| 68 | 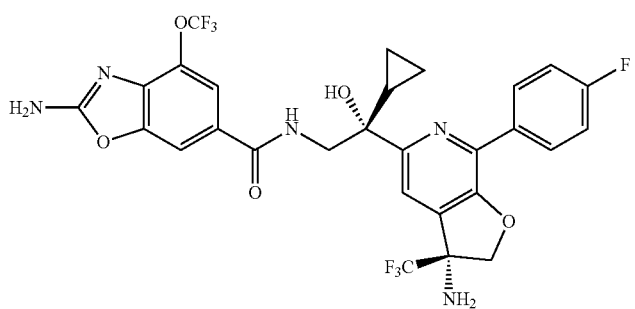 [SMILES: Nc1nc2c(OC(F)(F)F)cc(C(=O)NC[C@](O)(c3cc4c(c(-c5ccc(F)cc5)n3)OC[C@@]4(N)C(F)(F)F)C3CC3)cc2s1] |

-continued
| Entry | Example |
|---|---|
| 69 | 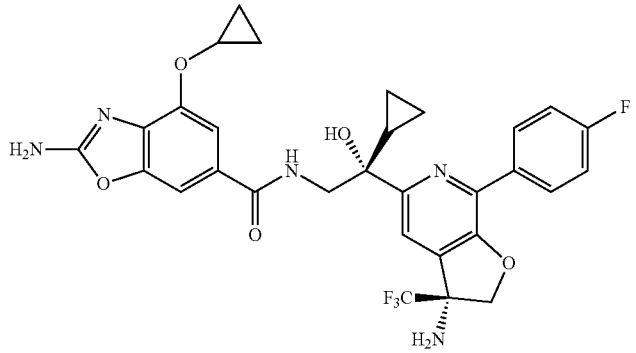 |
| 70 | 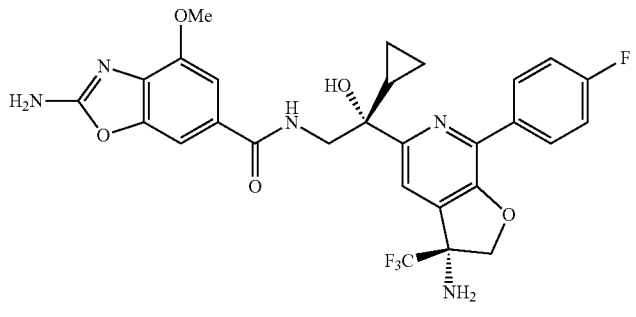 |
| 71 | 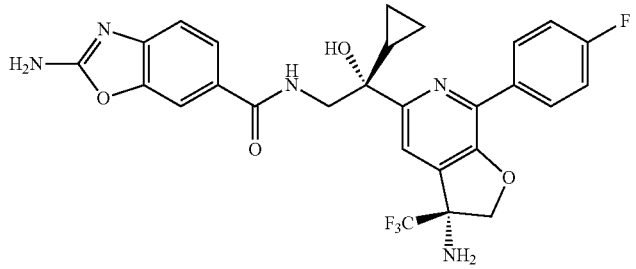 [SMILES: Nc1nc2ccc(C(=O)NC[C@](O)(c3cc4c(c(-c5ccc(F)cc5)n3)OC[C@@]4(N)C(F)(F)F)C3CC3)cc2o1] |
| 72 | 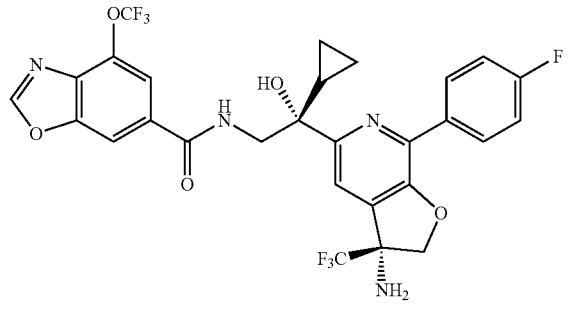 |
| 73 | 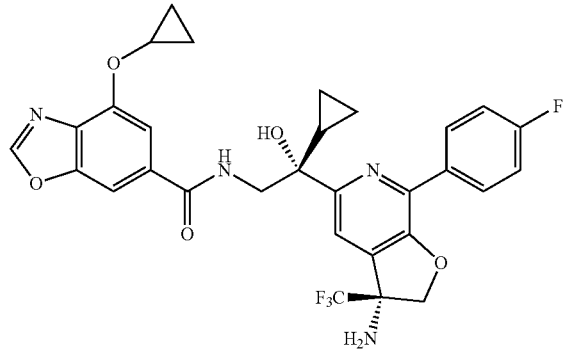 [SMILES: N[C@@]1(C(F)(F)F)COc2c1cc([C@@](O)(CNC(=O)c1cc(OC3CC3)c3ncoc3c1)C1CC1)nc2-c1ccc(F)cc1] |

| Entry | Example |
|---|---|
| 74 | 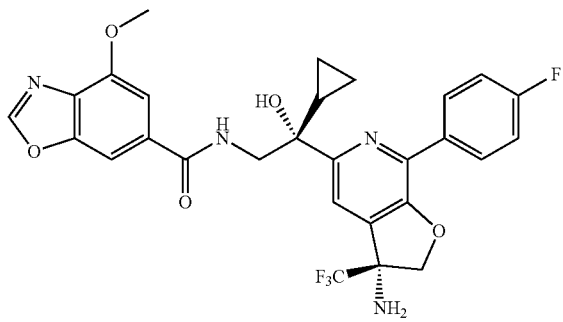 |
| 75 | 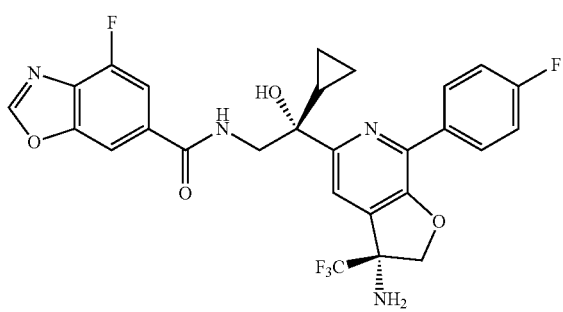 |
| 76 | 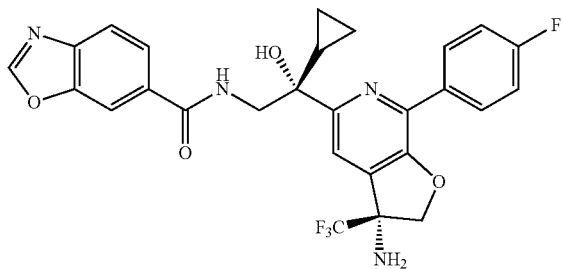 [SMILES: N[C@@]1(C(F)(F)F)COc2c1cc([C@@](O)(CNC(=O)c1ccc3ncoc3c1)C1CC1)nc2-c1ccc(F)cc1] |
| 77 | 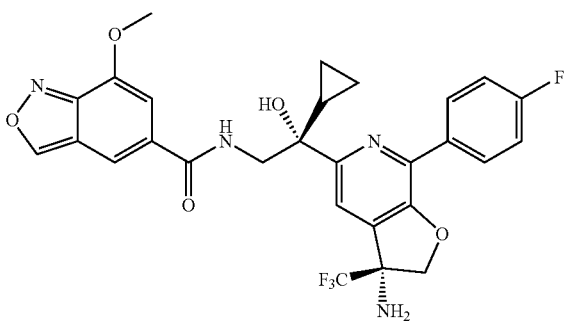 [SMILES: COc1cc(C(=O)NC[C@](O)(c2cc3c(c(-c4ccc(F)cc4)n2)OC[C@@]3(N)C(F)(F)F)C2CC2)cc2conc12] |
| 78 | 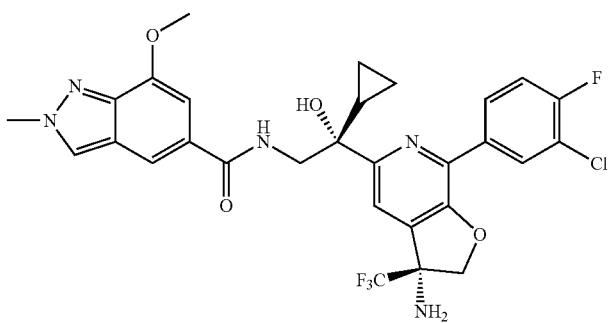 [SMILES: COc1cc(C(=O)NC[C@](O)(c2cc3c(c(-c4ccc(F)c(Cl)c4)n2)OC[C@@]3(N)C(F)(F)F)C2CC2)cc2cn(C)nc12] |

| Entry | Example |
|---|---|
| 79 | 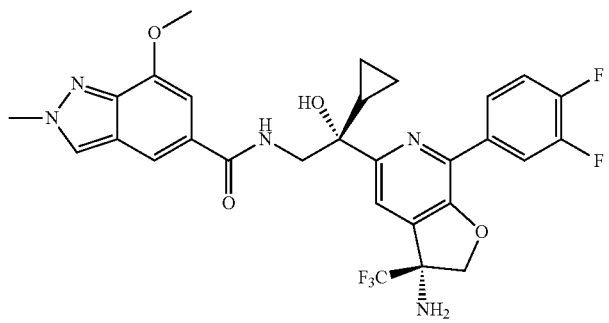 [SMILES: COc1cc(C(=O)NC[C@](O)(c2cc3c(c(-c4ccc(F)c(F)c4)n2)OC[C@@]3(N)C(F)(F)F)C2CC2)cc2cn(C)nc12] |
| 80 | 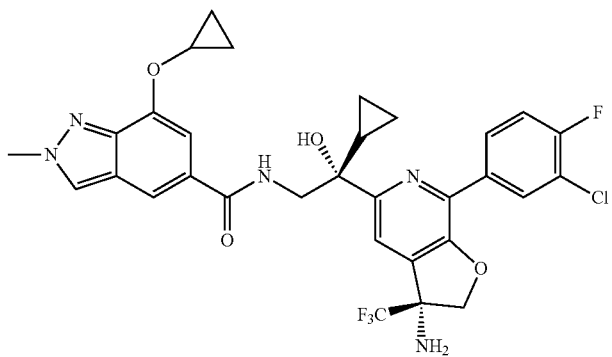 [SMILES: Cn1cc2cc(C(=O)NC[C@](O)(c3cc4c(c(-c5ccc(F)c(Cl)c5)n3)OC[C@@]4(N)C(F)(F)F)C3CC3)cc(OC3CC3)c2n1] |
| 81 | 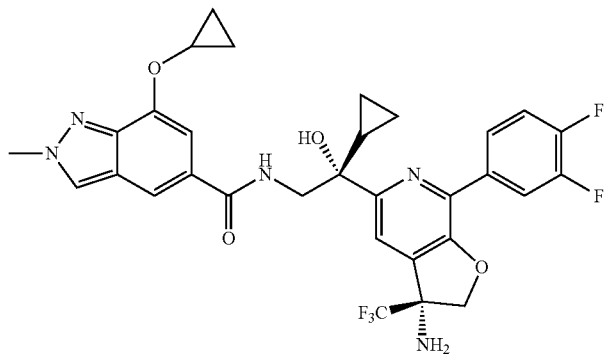 [SMILES: Cn1cc2cc(C(=O)NC[C@](O)(c3cc4c(c(-c5ccc(F)c(F)c5)n3)OC[C@@]4(N)C(F)(F)F)C3CC3)cc(OC3CC3)c2n1] |
| 82 | 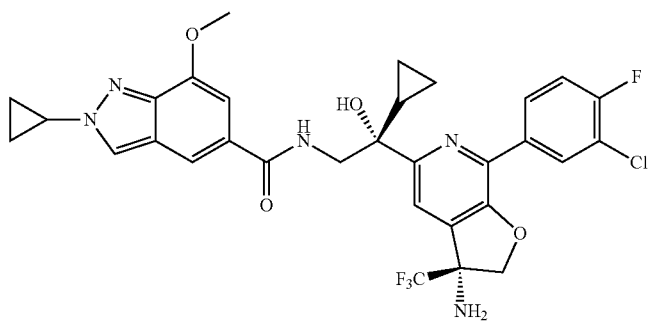 [SMILES: COc1cc(C(=O)NC[C@](O)(c2cc3c(c(-c4ccc(F)c(Cl)c4)n2)OC[C@@]3(N)C(F)(F)F)C2CC2)cc2cn(C3CC3)nc12] |

| Entry | Example |
|---|---|
| 83 | (structure) |
| 84 | (structure) |

Assays

Methods for RSV-A Assay

Hep-2 cells, (originally derived from tumors grown in irradiated-cortisonised weanling rats that had been injected with epidermoid carcinoma tissue from a 56 year old male's larynx, but later found to be indistinguishable from HeLa cells by PCR DNA analysis), were used for the culturing of genotype A, "Long" strain RSV. Flasks were inoculated with RSV and viral stocks were collected once cytopathic effect (CPE) was greater than 90%. Viral stocks in 25% sucrose media were snap frozen using liquid nitrogen to increase viral stability. Viral stock titers were quantified by tissue culture infectious dose 50% ($TCID_{50}$) using 8,000 cells per well and 3-fold viral dilutions across a 96-well plate, cultured for 4 days. Viral stock titers were also quantified by a plaque forming unit assay, as described elsewhere.

Following extensive parameter testing, the final assay is run as follows: Hep-2 cells are seeded into the inner 60 wells of a 96-well plate at 8,000 cells per well in a volume of 50 µL using Growth Media (DMEM without phenol red, 1% L-Glut, 1% Penn/Strep, 1% nonessential amino acids, 10% heat-inactivated FBS). 2-fold serial dilutions of control and test compounds are added to the wells in duplicate in a total volume of 25 µL. Viral stock is then added to the wells at a multiplicity of infection (MOI) of 0.1 in a volume of 25 µL, bringing the total volume of each well to 100 µL. The MOI is calculated using the PFU/mL, or $TCID_{50}$ if unavailable. Each 96-well plate has a control column of 6 wells with cells and virus but no compound (negative control, max CPE), a column with cells but no compound or virus (positive control, minimum CPE), and a column with no cells or virus or compound (background plate/reagent control). The control wells with cells but no virus are given an additional 254, of growth media containing an equal quantity of sucrose as those wells receiving the viral stock in order to keep consistent in media and volume conditions. The outer wells of the plate are filled with 125 µL of moat media (DMEM, 1% Penn/Strep) to act as a thermal and evaporative moat around the test wells. Following a 5-day incubation period, the plates are read using ATPlite (50 uL added per well), which quantifies the amount of ATP (a measure of cell health) present in each well. Assay plates are read using the Envision luminometer. These data are used to calculate the $EC_{50}$ each compound (Table 1). $EC_{50}$ ranges are as follows: A<0.2 µM; B≥0.2 µM.

TABLE 1

Summary of Activities for RSV-A

| Example | Human RSV-A ("Long" strain) $EC_{50}$ | Example | Human RSV-A ("Long" strain) $EC_{50}$ |
|---|---|---|---|
| 1 | A | 2 | B |
| 3 | A | 4 | B |
| 5 | A | 6 | A |
| 7 | A | 8 | A |
| 9 | A | 10 | A |
| 11 | A | 12 | B |
| 13 | A | 14 | A |
| 15 | A | 16 | A |
| 17 | A | 18 | A |
| 19 | A | 20 | A |
| 21 | A | 22 | A |
| 23 | A | 24 | A |
| 25 | A | 26 | A |
| 27 | A | 28 | A |
| 29 | A | 30 | A |
| 31 | B | 32 | B |
| 33 | B | 34 | B |
| 35 | B | 36 | B |
| 37 | B | 38 | B |
| 39 | B | 40 | B |
| 41 | B | 42 | B |

TABLE 1-continued

Summary of Activities for RSV-A

| Example | Human RSV-A ("Long" strain) $EC_{50}$ | Example | Human RSV-A ("Long" strain) $EC_{50}$ |
|---|---|---|---|
| 43 | B | 44 | B |
| 45 | B | 46 | B |
| 47 | B | 48 | B |
| 49 | A | 50 | A |
| 51 | A | 52 | A |
| 53 | A | 54 | A |
| 55 | A | 55c | A |
| 55d | A | 56 | B |
| 57 | B | 58 | B |
| 59 | B | 59b | B |
| 59c | B | 59d | A |
| 59e | A | 64 | A |
| 66 | A | | |

Method for HMPV Antiviral Assay

HMPV antiviral activity was evaluated using a recombinant version of HMPV CAN97-83 engineered to contain the coding sequence for enhanced green fluorescence protein (eGFP) in the 3' end of the virus genome (MPV-GFP1, ViraTree). Vero E6 cells (ATCC #CCL-7) were seeded at a density of 12,000 cells/100 µL/well into 96-well cell plates (VENDOR) one day prior to the assay. On the day of screening, the cell culture medium was aspirated from the wells and cells were washed twice with serum-free Eagle's Modified Essential Medium (EMEM, ATCC #) containing 1% penicillin-streptomycin (Invitrogen) (SF-EMEM). Cell washes were performed by dispensing 100 µL SF-EMEM per well and immediately aspirating the wash medium from the well. Following the second wash step, serum-free OptiMEM (Invitrogen, Cat No.) (SF-OptiMEM) containing 0.5 µg/mL TPCK-Trypsin (VENDOR) and 1% penicillin-streptomycin was added to the cells at 50 µL/well. Compounds were added into the 96-well plates using a JANUS automated liquid handling system (VENDOR). Compounds were initially diluted 1:50 into an intermediate 96-well plate containing SF-OptiMEM prior to transfer to the assay plate (25 µL/well). Each of the test compounds was tested in duplicate wells at final concentrations starting from 8 µM or 2 µM using ½ stepwise dilutions for a total of 8 points. Virus infection was performed by preparing a working stock of MPV-GFP1 at a multiplicity of infection (MOI) equal to 0.05/25 µL and aliquoting 25 µL of virus inoculum to the compound and positive control wells. SF-OptiMEM was added (25 µL/well) to the appropriate wells to serve as a virus-free negative control for the assay. The final DMSO concentration of all wells is 0.5%. Plates were incubated at 32° C., 5% $CO_2$ for 5 days. After 5 days incubation, eGFP fluorescence intensity was measured at (X) nM wavelength using a Spectramax i3X plate reader (VENDOR). Percent viral inhibition was calculated using the following equation:

$$y=[100-(X_Q/X_P)] \times 100$$

Where $X_Q$ is the fluorescence intensity measured in a well containing recombinant MPV-GFP1-infected, compound-treated cells and $X_P$ is the average fluorescence intensity measured in the wells containing untreated cells infected with recombinant virus. $EC_{50}$ values were then calculated by non-linear regression using a four parameter curve logistic equation. The curve fit model employed was XLFit Dose Response One Site Model 200:

$$y=(A+(B/(1+((x/C)^\wedge D))))$$

Where A is the minimum y value, B is the maximum y value, C is the log $EC_{50}$ value, and D is the slope factor. The $EC_{50}$ of each compound is listed in Table 2 and $EC_{50}$ ranges are as follows: A<0.2 µM; B≥0.2 µM.

TABLE 2

Summary of Activities for hMPV

| Example | rHMPV-GFP $EC_{50}$ | Example | rHMPV-GFP $EC_{50}$ |
|---|---|---|---|
| 1 | B | 2 | — |
| 3 | B | 4 | B |
| 5 | B | 6 | B |
| 7 | A | 8 | A |
| 9 | A | 10 | B |
| 11 | B | 12 | — |
| 13 | B | 14 | — |
| 15 | — | 16 | — |
| 19 | A | 20 | A |
| 21 | — | 22 | A |
| 23 | A | 24 | A |
| 25 | A | 26 | A |
| 27 | A | 28 | A |
| 29 | B | 30 | B |
| 47 | B | 48 | B |
| 49 | B | 51 | B |
| 55c | A | 55d | A |
| 66 | A | | |

While this invention has been particularly shown and described with references to preferred embodiments thereof, it will be understood by those skilled in the art that various changes in form and details may be made therein without departing from the scope of the invention encompassed by the appended claims.

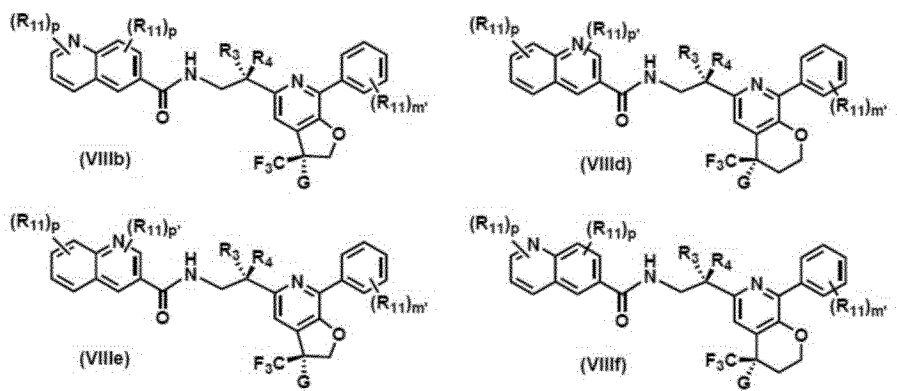

What is claimed:
1. A compound represented by Formula (I):

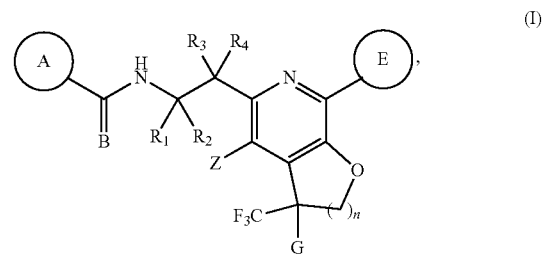

or a pharmaceutically acceptable salt thereof, wherein:
A is an optionally substituted aryl or optionally substituted heteroaryl;
B is O or S;
$R_1$ and $R_2$ are each independently hydrogen or an optionally substituted $C_1$-$C_4$ alkyl;
alternatively, $R_1$ and $R_2$ are taken together with carbon atom to which they attached to form an optionally substituted 3-6-membered cyclic ring;
$R_3$ is selected from the group consisting of hydrogen, hydroxy, and optionally substituted $C_1$-$C_6$ alkoxy;
$R_4$ is selected from the group consisting of hydrogen, optionally substituted $C_1$-$C_6$ alkyl, optionally substituted $C_1$-$C_6$ alkenyl, optionally substituted $C_1$-$C_6$ alkynyl, optionally substituted $C_3$-$C_6$ cycloalkyl, and optionally substituted 3-6 membered heterocyclic;
Z is selected from the group consisting of hydrogen, halogen, cyano, optionally substituted $C_1$-$C_6$ alkyl, optionally substituted $C_3$-$C_6$ cycloalkyl, and optionally substituted $C_1$-$C_6$ alkoxy;

E is an optionally substituted aryl, optionally substituted heteroaryl, or optionally substituted heterocyclic;

G is NR$_5$R$_6$;

R$_5$ and R$_6$ are each independently selected from:
1) hydrogen,
2) optionally substituted C$_1$-C$_6$ alkyl,
3) optionally substituted C$_3$-C$_6$ cycloalkyl,
4) optionally substituted 3-6 membered heterocyclic,
5) optionally substituted aryl,
6) optionally substituted heteroaryl,
7) —C(=O)R$_7$,
8) —C(=O)OR$_7$,
9) —C(=O)NHR$_7$,
10) —C(=NH)R$_7$,
11) —C(=NH)NHR$_7$,
12) —C(=NH)NHCN,
13) —C(=NH)NHC(=O)R$_7$,
14) —SO$_2$R$_7$, and
15) —SO$_2$NHR$_7$, alternatively, R$_5$ and R$_6$ are taken together with the nitrogen they are attached to form an optionally substituted 3-8-membered heterocyclic ring;

wherein, R$_7$ is selected from the group consisting of hydrogen, optionally substituted C$_1$-C$_6$ alkyl, optionally substituted C$_3$-C$_6$ cycloalkyl, optionally substituted 3-6 membered heterocyclic, optionally substituted aryl, and optionally substituted heteroaryl; and n is 1, 2 or 3.

2. The compound of claim 1, wherein E is selected from the groups set forth below,

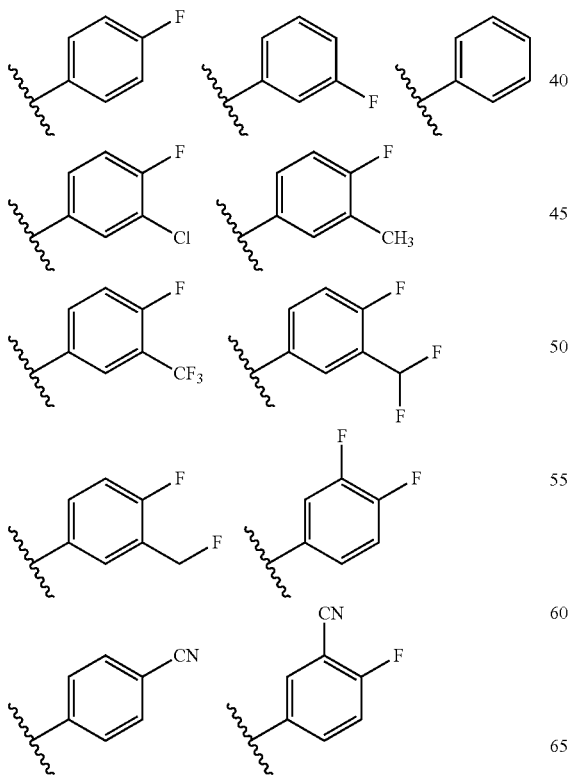

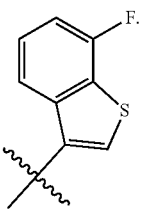

3. The compound of claim 1, wherein G is selected from the groups below:

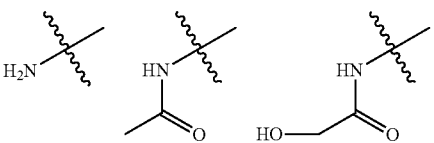

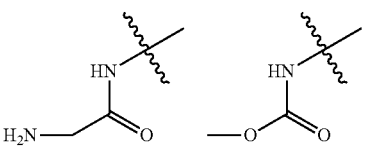

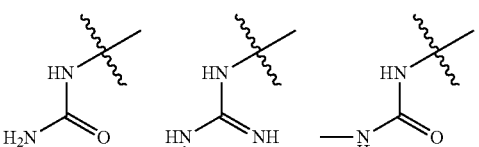

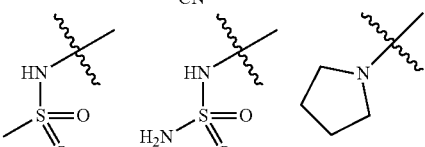

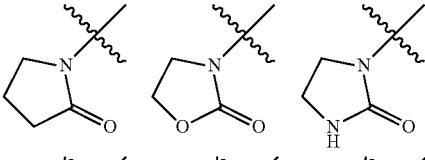

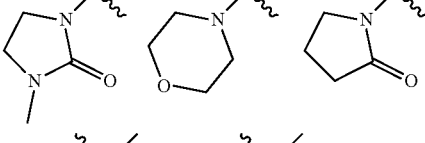

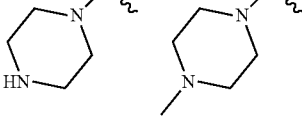

4. The compound of claim 1, represented by Formula (IIIa) or a pharmaceutically acceptable salt thereof:

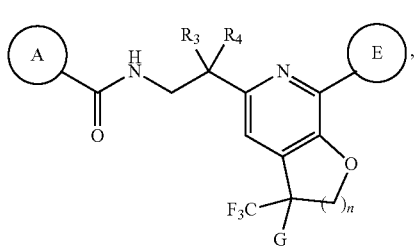

(IIIa)

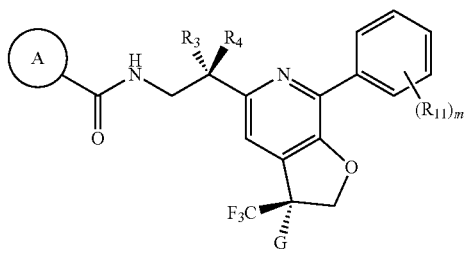

(VIIa)

wherein A, G, n, E, R₃, and R₄ are as defined in claim 1.

5. The compound of claim 1, represented by one of Formulas (Va') to (Vd'), or a pharmaceutically acceptable salt thereof:

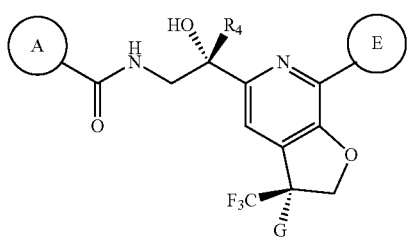

(Va')

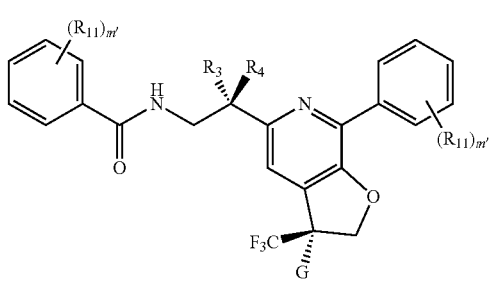

(VIIb)

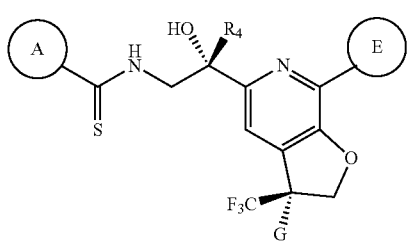

(Vb')

wherein each $R_{11}$ is independently optionally substituted —$C_1$-$C_6$ alkyl, optionally substituted $C_1$-$C_6$ alkoxyl, optionally substituted —$C_3$-$C_6$ cycloalkyl, halo, —CN, or —$NR_7R_8$; m is 0, 1, 2, 3, 4 or 5; $R_8$ is selected from the group consisting of hydrogen, optionally substituted $C_1$-$C_6$ alkyl, optionally substituted $C_3$-$C_6$ cycloalkyl, optionally substituted 3-6 membered heterocyclic, optionally substituted aryl, and optionally substituted heteroaryl; and A, G, $R_3$, $R_4$, and $R_7$ are as defined in claim 1.

7. The compound of claim 1, represented by one of Formulas (VIIIa) to (VIIIf), or a pharmaceutically acceptable salt thereof:

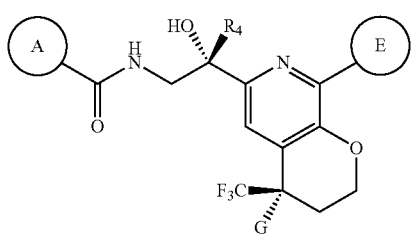

(Vc')

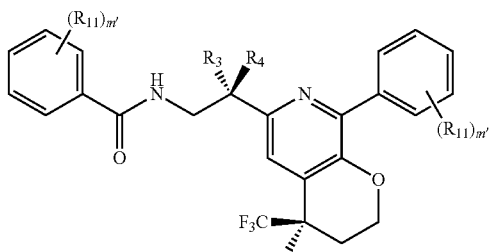

(VIIIa)

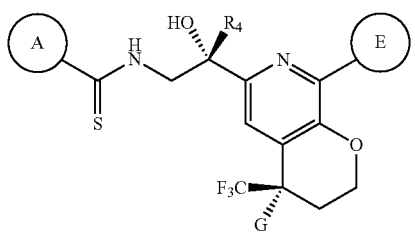

(Vd')

(VIIIc)

wherein A, R₄, E and G are as defined in claim 1.

6. The compound of claim 1, represented by one of Formulas (VIIa) and (VIIb), or a pharmaceutically acceptable salt thereof:

-continued (VIIIb)
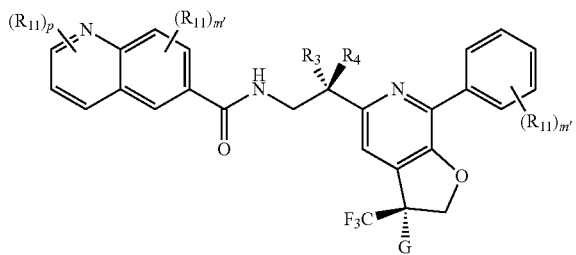

(Xa)
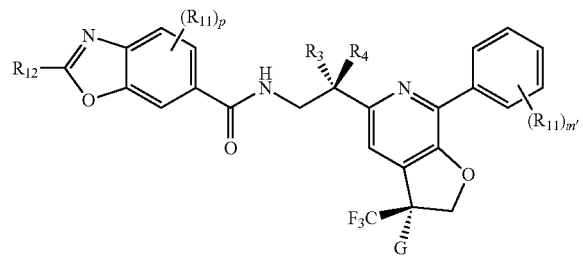

(VIIId)
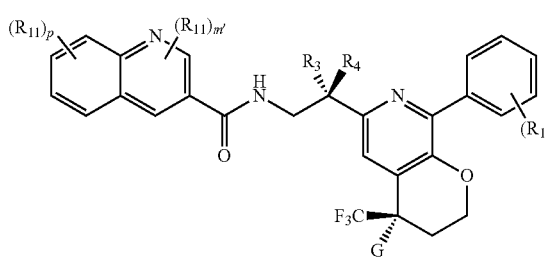

(Xj)
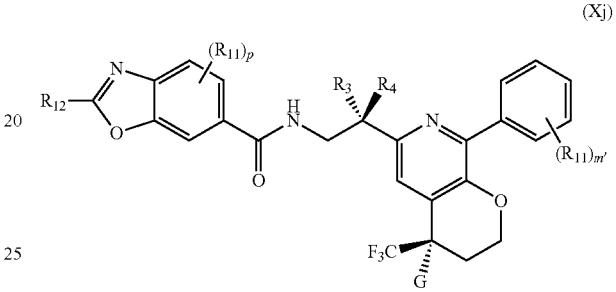

(VIIIe)
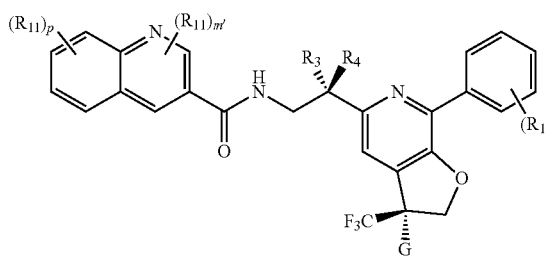

(Xg)
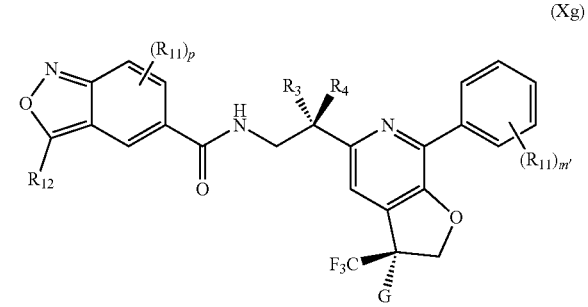

(VIIIf)
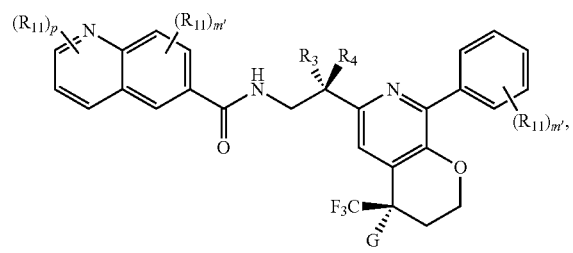

(Xd)
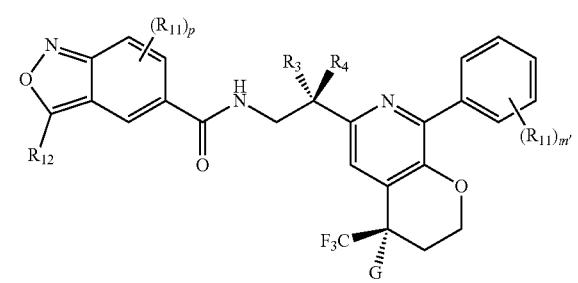

wherein each $R_{11}$ is independently optionally substituted —$C_1$-$C_6$ alkyl, optionally substituted $C_1$-$C_6$ alkoxyl, optionally substituted —$C_3$-$C_6$ cycloalkyl, halo, —CN, or —$NR_7R_8$; $R_8$ is selected from the group consisting of hydrogen, optionally substituted $C_1$-$C_6$ alkyl, optionally substituted $C_3$-$C_6$ cycloalkyl, optionally substituted 3-6 membered heterocyclic, optionally substituted aryl, and optionally substituted heteroaryl; each p is independently 0, 1, 2 or 3; each p' is 0, 1 or 2; each m' is independently 1, 2 or 3; and G, $R_3$, $R_4$, and $R_7$ are as defined in claim 1.

8. The compound of claim 1, represented by one of Formulas (Xa), (Xb), (Xc-1), (Xd)~(Xh), (Xi-1), (Xj), (Xk-1), and (Xm-1), or a pharmaceutically acceptable salt thereof:

(Xf)
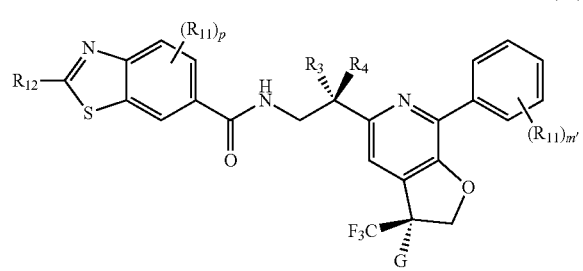

(Xb)
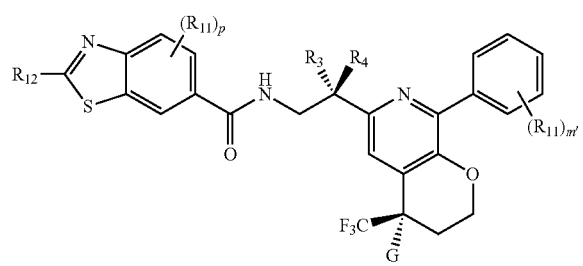

(Xh)
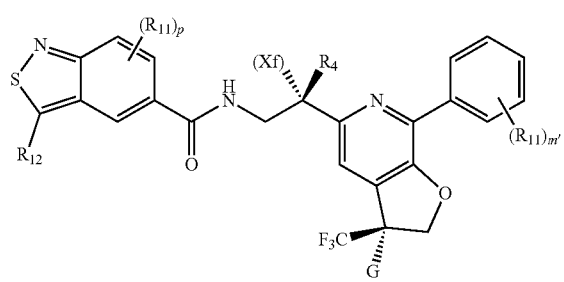

(Xe)
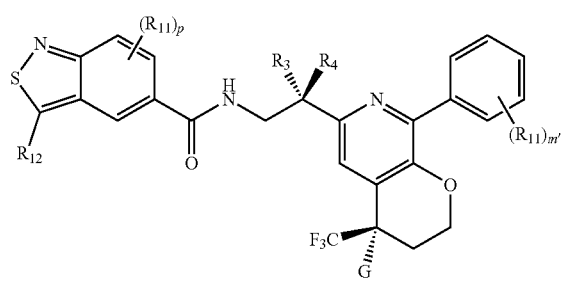

(Xc-1)
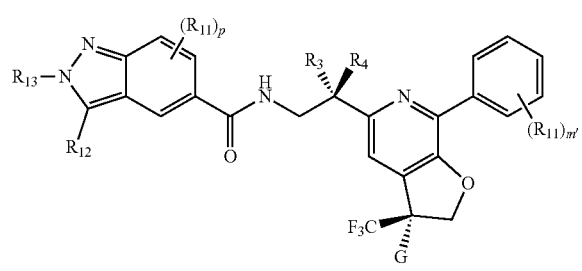

(Xk-1)
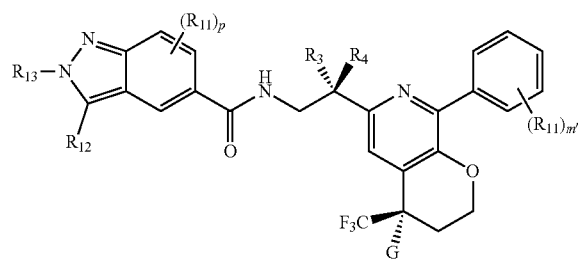

(Xi-1)
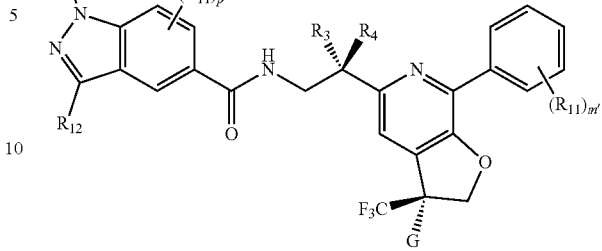

(Xm-1)
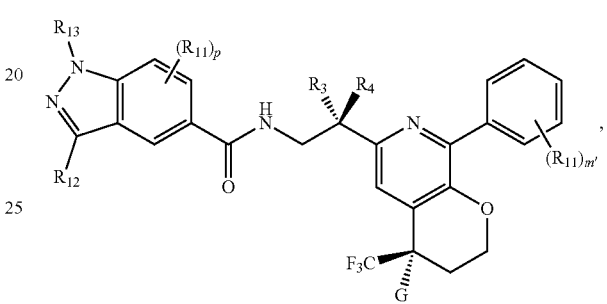

wherein each $R_{11}$ is independently optionally substituted —$C_1$-$C_6$ alkyl, optionally substituted $C_1$-$C_6$ alkoxyl, optionally substituted —$C_3$-$C_6$ cycloalkyl, halo, —CN, or —$NR_7R_8$; $R_8$ is selected from the group consisting of hydrogen, optionally substituted $C_1$-$C_6$ alkyl, optionally substituted $C_3$-$C_6$ cycloalkyl, optionally substituted 3-6 membered heterocyclic, optionally substituted aryl, and optionally substituted heteroaryl; each $R_{12}$ is independently hydrogen, optionally substituted —$C_1$-$C_6$ alkyl, optionally substituted $C_1$-$C_6$ alkoxyl, optionally substituted —$C_3$-$C_6$ cycloalkyl, halo, —CN, or —$NR_7R_8$; each $R_{13}$ is hydrogen, halo, optionally substituted —$C_1$-$C_6$ alkyl, optionally substituted —$C_3$-$C_6$ cycloalkyl, or optionally substituted 3-6-membered heterocyclic; each p is independently 0, 1, 2 or 3; each m' is independently 1, 2 or 3; and G, $R_3$, $R_4$, and $R_7$ are as defined in claim 1.

9. The compound of claim 1, represented by one of Formulas (XIVa) to (XIVb), or a pharmaceutically acceptable salt thereof:

(XIVa)
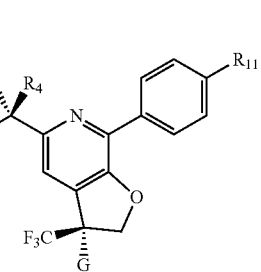

-continued (XIVb)

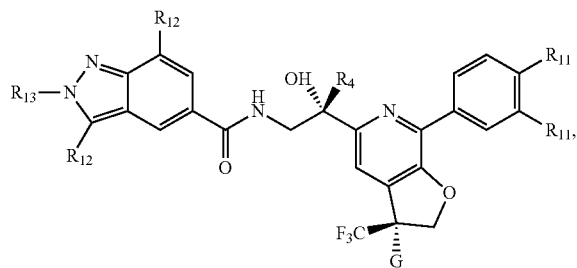

wherein each $R_{11}$ is independently optionally substituted —$C_1$-$C_6$ alkyl, optionally substituted $C_1$-$C_6$ alkoxyl, optionally substituted —$C_3$-$C_6$ cycloalkyl, halo, —CN, or —$NR_7R_8$; each $R_{12}$ is independently hydrogen, optionally substituted —$C_1$-$C_6$ alkyl, optionally substituted $C_1$-$C_6$ alkoxyl, optionally substituted —$C_3$-$C_6$ cycloalkyl, halo, —CN, or —$NR_7R_8$; each $R_{13}$ is hydrogen, halo, optionally substituted —$C_1$-$C_6$ alkyl, optionally substituted —$C_3$-$C_6$ cycloalkyl, or optionally substituted 3-6-membered heterocyclic; $R_8$ is selected from the group consisting of hydrogen, optionally substituted $C_1$-$C_6$ alkyl, optionally substituted $C_3$-$C_6$ cycloalkyl, optionally substituted 3-6 membered heterocyclic, optionally substituted aryl, and optionally substituted heteroaryl; $R_7$, G and $R_4$ are as defined in claim 1.

10. The compound of claim 1, selected from the compounds set forth below, or a pharmaceutically acceptable salt thereof:

| Compound | Structure |
|---|---|
| 1 | 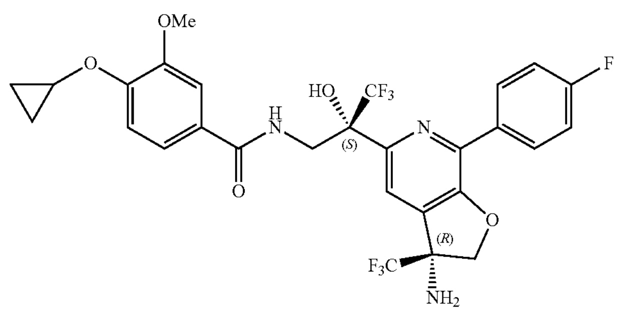 |
| 2 | 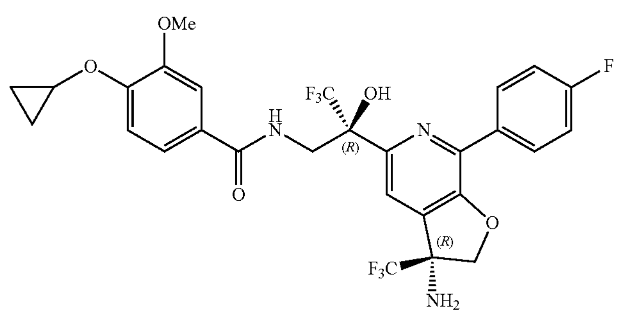 |
| 3 | 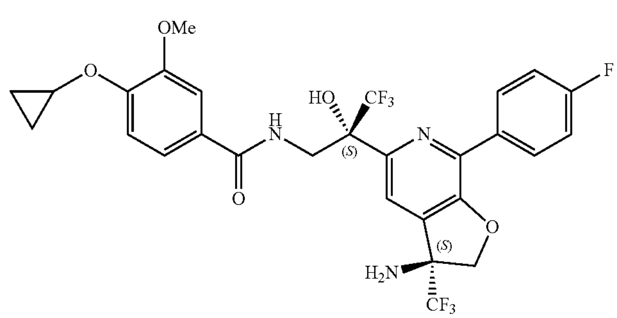 |

-continued
| Compound | Structure |
|---|---|
| 4 | 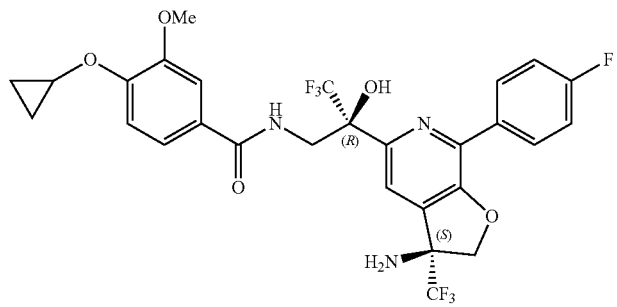 |
| 5 | 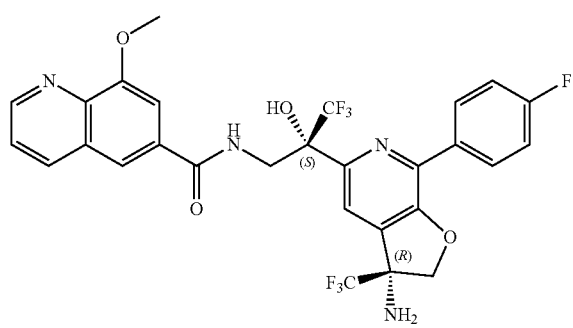 |
| 6 | 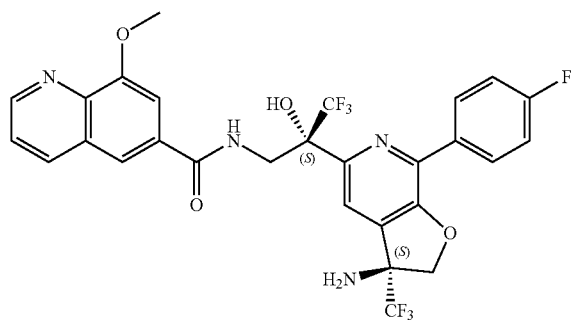 |
| 7 | 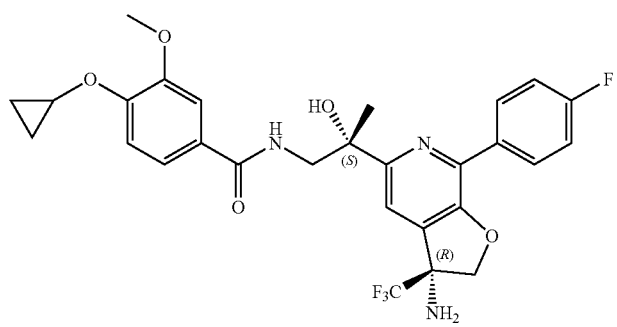 |
| 8 | 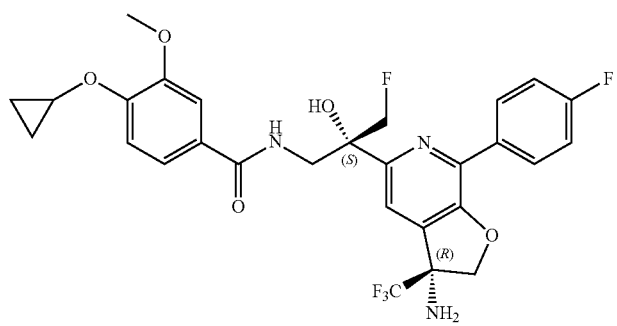 |

| Compound | Structure |
|---|---|
| 9 | 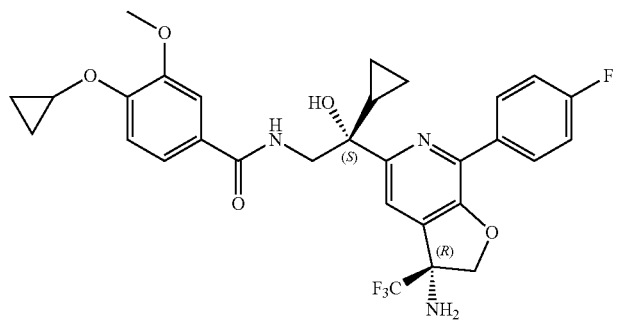 |
| 10 | 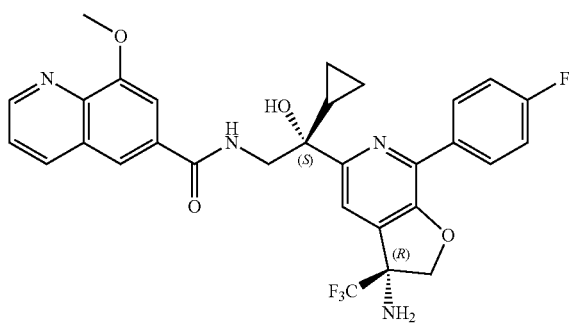 |
| 11 | 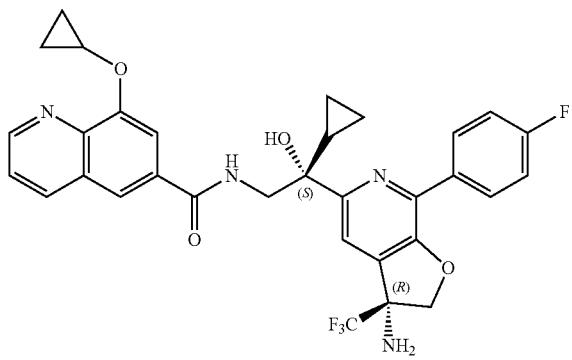 |
| 12 | 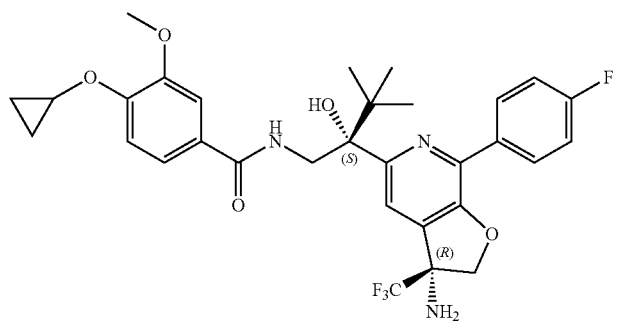 |

| Compound | Structure |
|---|---|
| 13 | 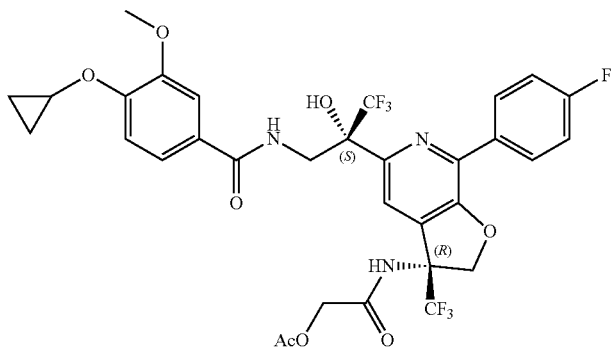 |
| 14 | 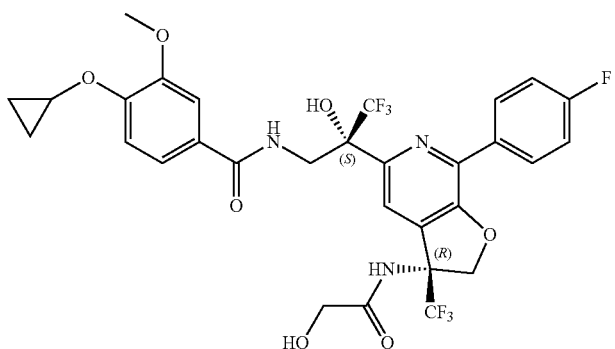 |
| 15 | 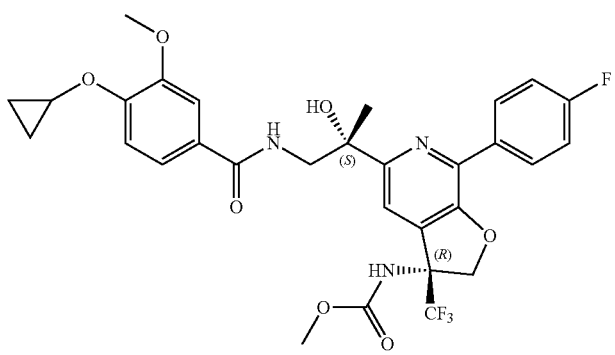 |
| 16 | 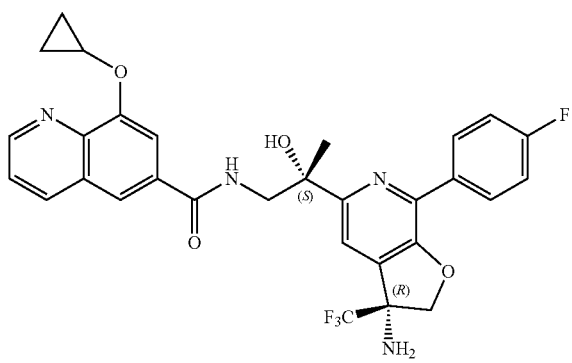 |

| Compound | Structure |
|---|---|
| 17 | 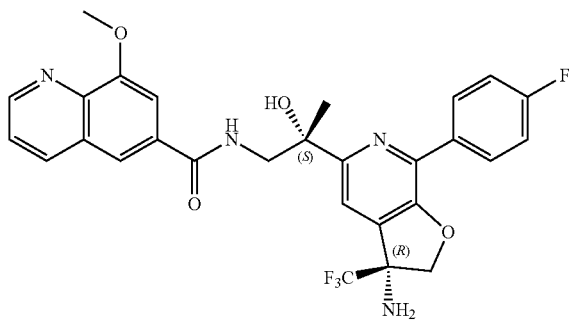 |
| 18 | 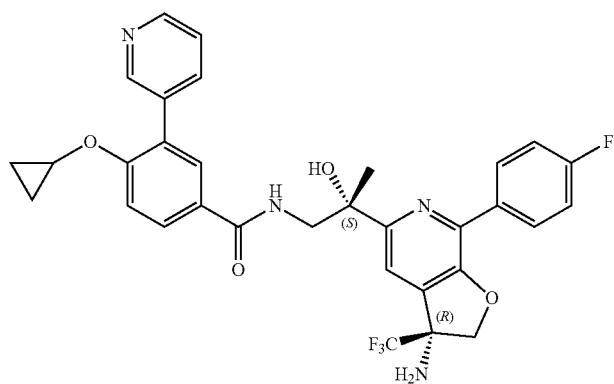 |
| 19 | 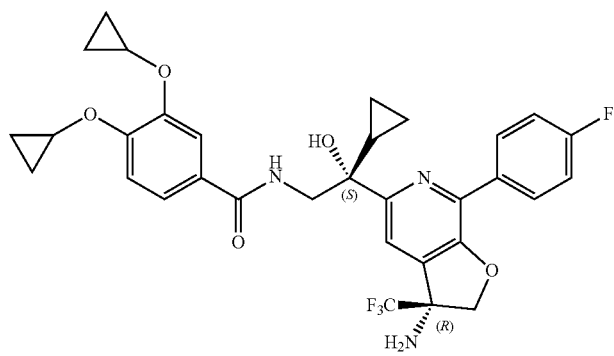 |
| 20 | 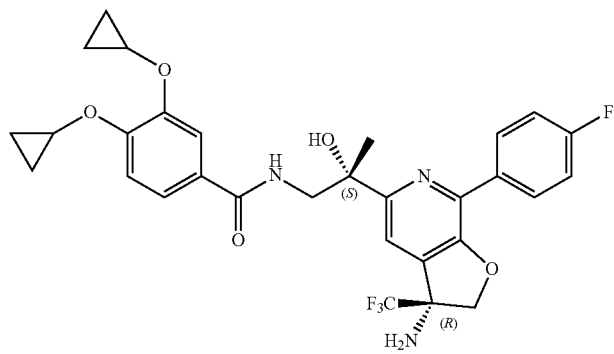 |

-continued

| Compound | Structure |
|---|---|
| 21 | 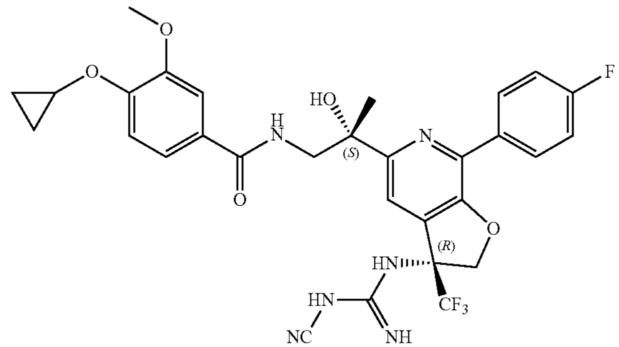 |
| 22 | 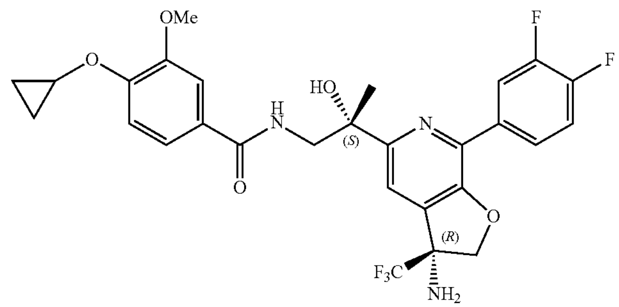 |
| 23 | 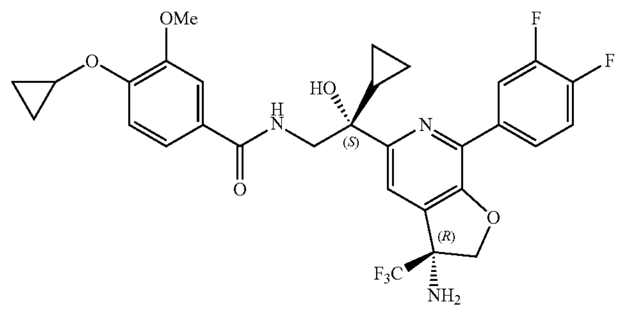 |
| 24 | 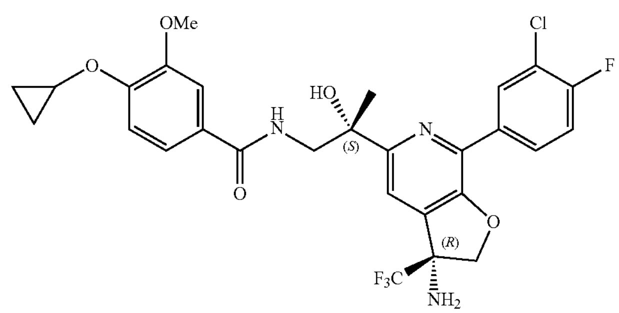 |
| 25 | 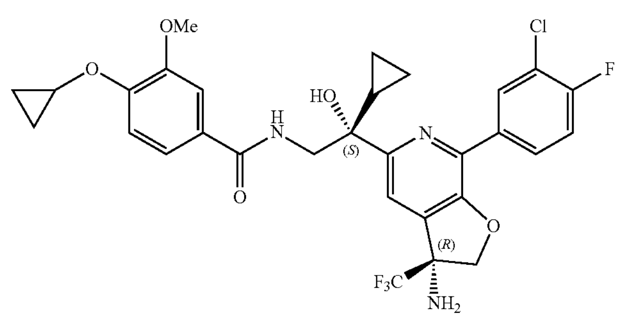 |

| Compound | Structure |
|---|---|
| 26 | 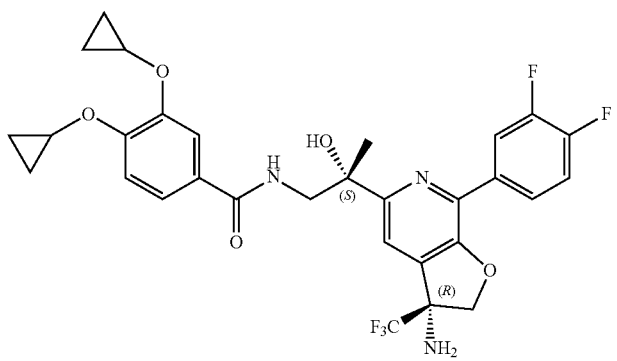 |
| 27 | 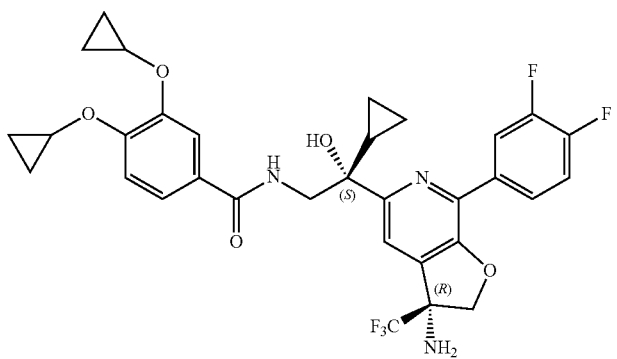 |
| 28 | 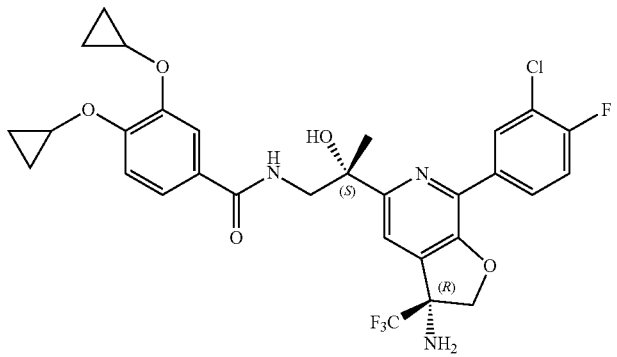 |
| 29 | 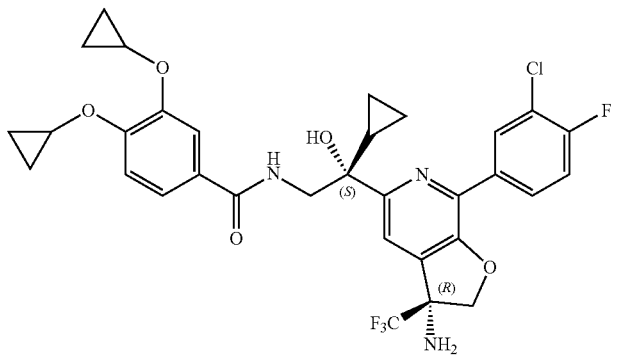 |

-continued
| Compound | Structure |
|---|---|
| 30 | 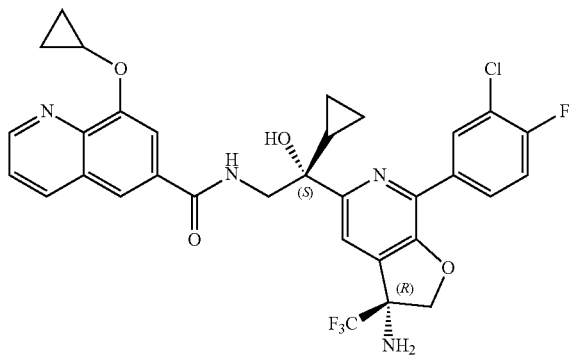 |
| 31 | 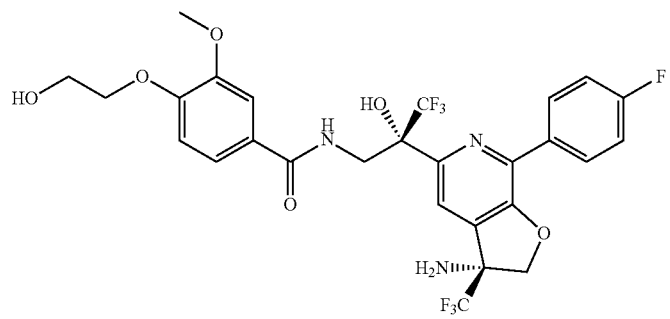 [SMILES: COc1cc(C(=O)NC[C@](O)(c2cc3c(c(-c4ccc(F)cc4)n2)OC[C@@]3(N)C(F)(F)F)C(F)(F)F)ccc1OCCO] |
| 32 | 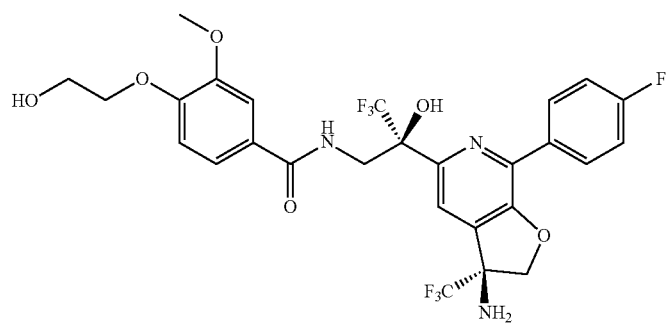 |
| 33 | 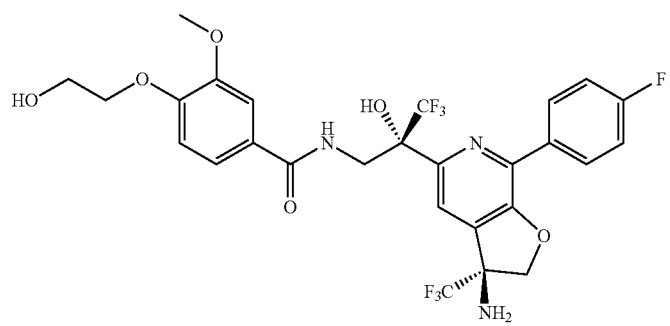 [SMILES: COc1cc(C(=O)NC[C@](O)(c2cc3c(c(-c4ccc(F)cc4)n2)OC[C@]3(N)C(F)(F)F)C(F)(F)F)ccc1OCCO] |

| Compound | Structure |
|---|---|
| 34 | 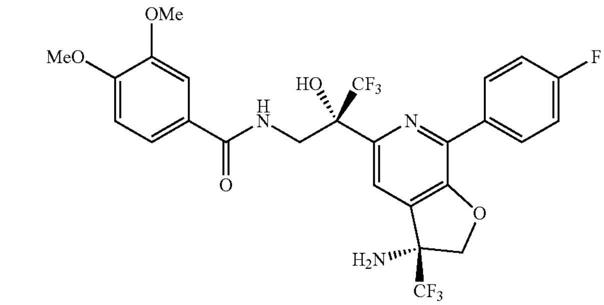 |
| 35 | 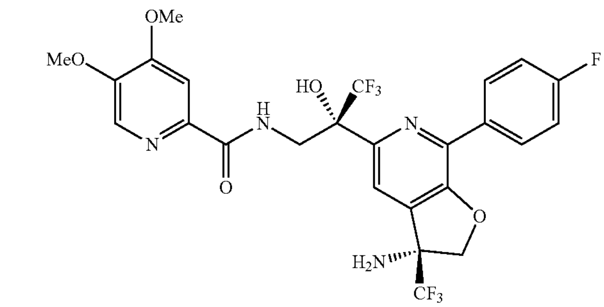 |
| 36 | 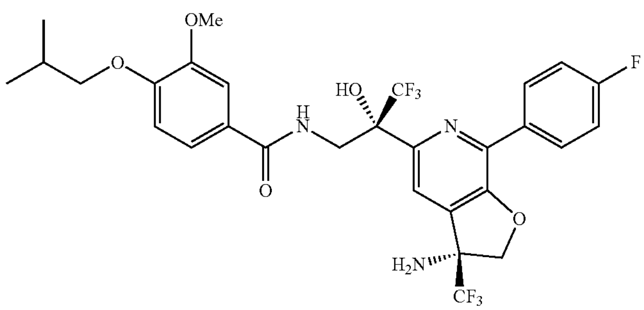 [SMILES: COc1cc(C(=O)NC[C@](O)(c2cc3c(c(-c4ccc(F)cc4)n2)OC[C@@]3(N)C(F)(F)F)C(F)(F)F)ccc1OCC(C)C] |
| 37 | 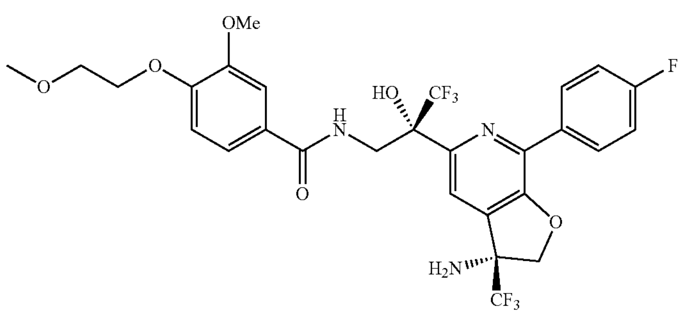 [SMILES: COCCOc1ccc(C(=O)NC[C@](O)(c2cc3c(c(-c4ccc(F)cc4)n2)OC[C@@]3(N)C(F)(F)F)C(F)(F)F)cc1OC] |
| 38 | 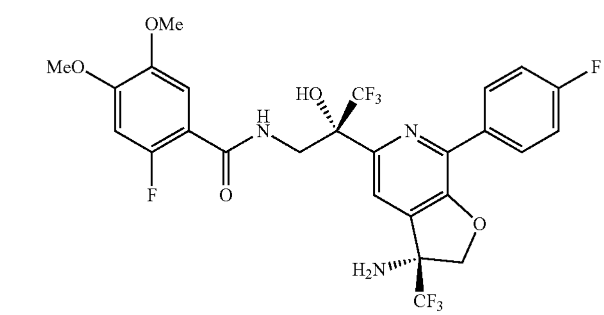 [SMILES: COc1cc(F)c(C(=O)NC[C@](O)(c2cc3c(c(-c4ccc(F)cc4)n2)OC[C@@]3(N)C(F)(F)F)C(F)(F)F)cc1OC] |

-continued
| Compound | Structure |
|---|---|
| 39 | 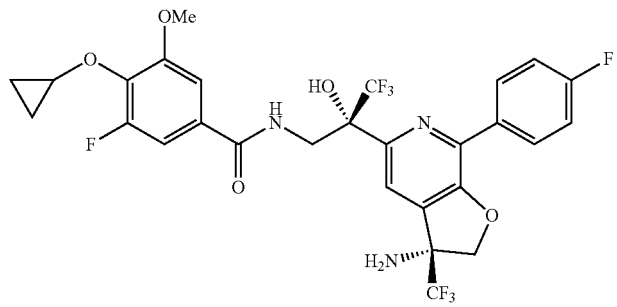 [SMILES: COc1cc(C(=O)NC[C@](O)(c2cc3c(c(-c4ccc(F)cc4)n2)OC[C@@]3(N)C(F)(F)F)C(F)(F)F)cc(F)c1OC1CC1] |
| 40 | 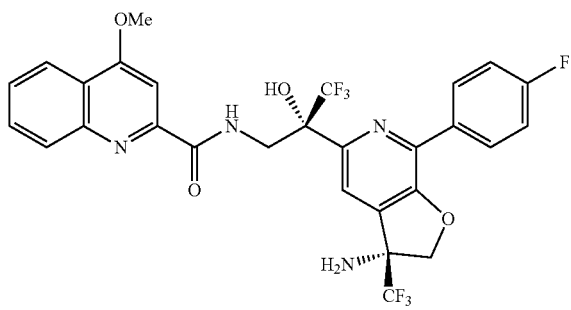 [SMILES: COc1cc(C(=O)NC[C@](O)(c2cc3c(c(-c4ccc(F)cc4)n2)OC[C@@]3(N)C(F)(F)F)C(F)(F)F)nc2ccccc12] |
| 41 | 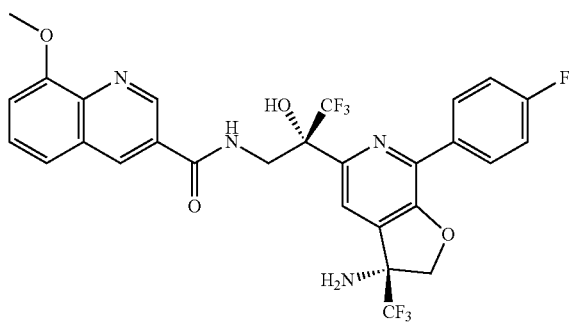 [SMILES: COc1cccc2cc(C(=O)NC[C@](O)(c3cc4c(c(-c5ccc(F)cc5)n3)OC[C@@]4(N)C(F)(F)F)C(F)(F)F)cnc12] |
| 42 | 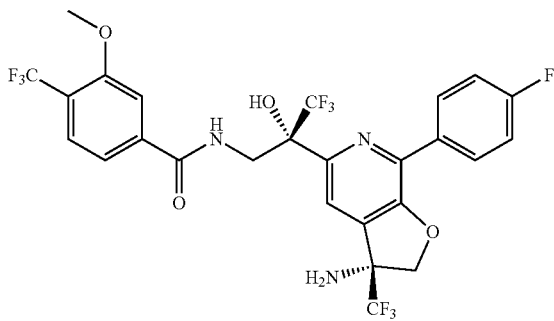 [SMILES: COc1cc(C(=O)NC[C@](O)(c2cc3c(c(-c4ccc(F)cc4)n2)OC[C@@]3(N)C(F)(F)F)C(F)(F)F)ccc1C(F)(F)F] |
| 43 | 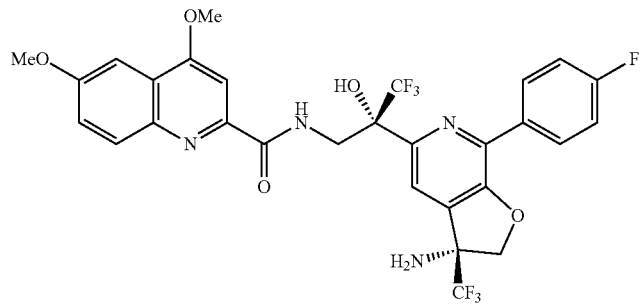 [SMILES: COc1ccc2nc(C(=O)NC[C@](O)(c3cc4c(c(-c5ccc(F)cc5)n3)OC[C@@]4(N)C(F)(F)F)C(F)(F)F)cc(OC)c2c1] |

-continued
| Compound | Structure |
|---|---|
| 44 | 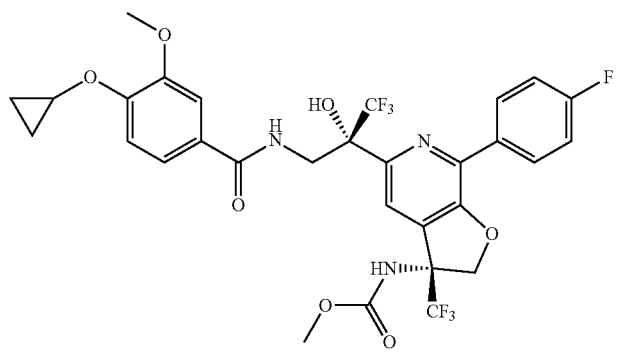 [SMILES: COC(=O)N[C@@]1(C(F)(F)F)COc2c1cc([C@@](O)(CNC(=O)c1ccc(OC3CC3)c(OC)c1)C(F)(F)F)nc2-c1ccc(F)cc1] |
| 45 | 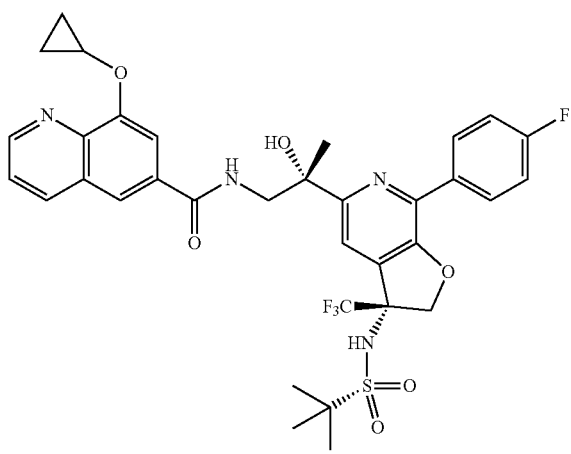 |
| 46 | 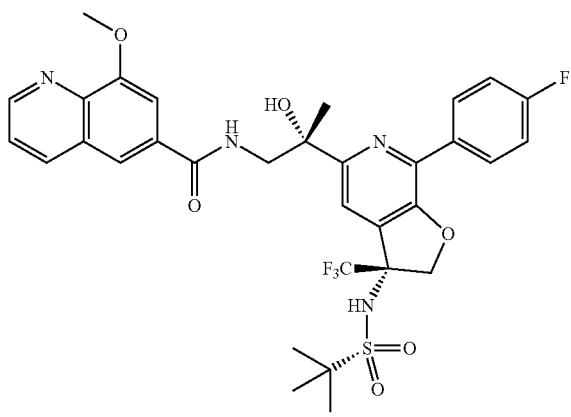 |
| 47 | 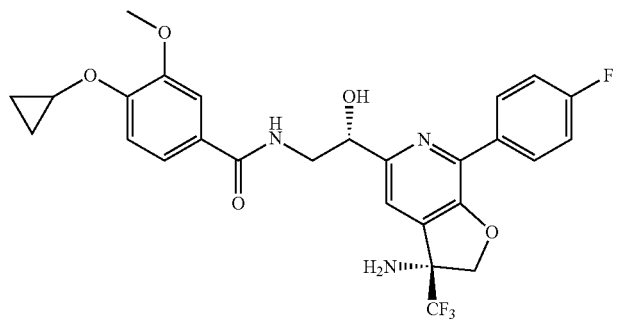 [SMILES: COc1cc(C(=O)NC[C@H](O)c2cc3c(c(-c4ccc(F)cc4)n2)OC[C@@]3(N)C(F)(F)F)ccc1OC1CC1] |

-continued

| Compound | Structure |
|---|---|
| 48 | 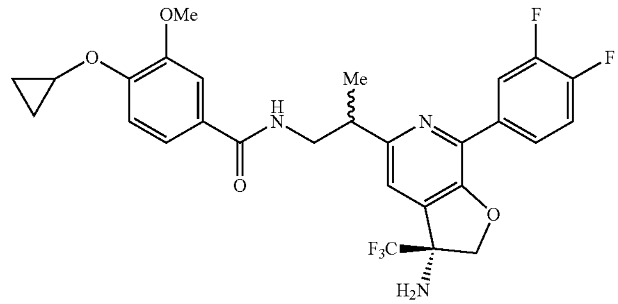 [SMILES: COc1cc(C(=O)NCC(C)c2cc3c(c(-c4ccc(F)c(F)c4)n2)OC[C@@]3(N)C(F)(F)F)ccc1OC1CC1] |
| 49 | 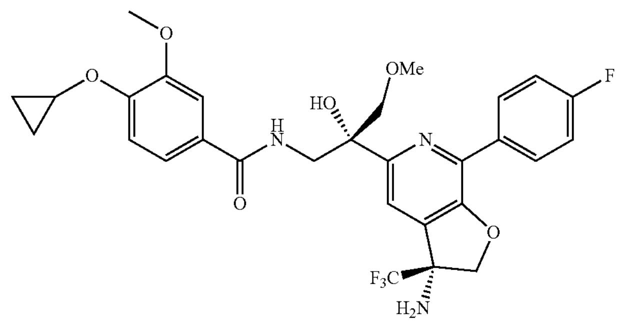 [SMILES: COC[C@](O)(CNC(=O)c1ccc(OC2CC2)c(OC)c1)c1cc2c(c(-c3ccc(F)cc3)n1)OC[C@@]2(N)C(F)(F)F] |
| 50 | 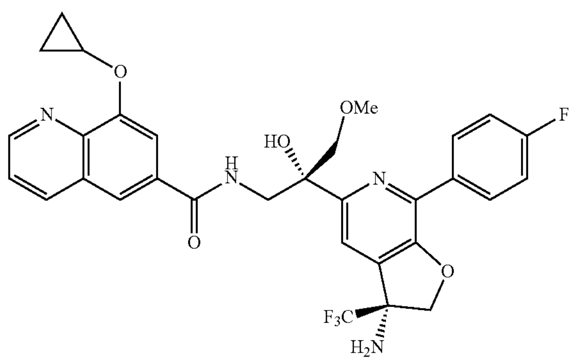 [SMILES: COC[C@](O)(CNC(=O)c1cc(OC2CC2)c2ncccc2c1)c1cc2c(c(-c3ccc(F)cc3)n1)OC[C@@]2(N)C(F)(F)F] |
| 51 | 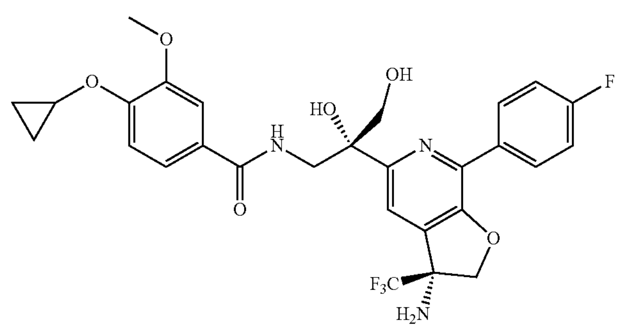 [SMILES: COc1cc(C(=O)NC[C@@](O)(CO)c2cc3c(c(-c4ccc(F)cc4)n2)OC[C@@]3(N)C(F)(F)F)ccc1OC1CC1] |
| 52 | 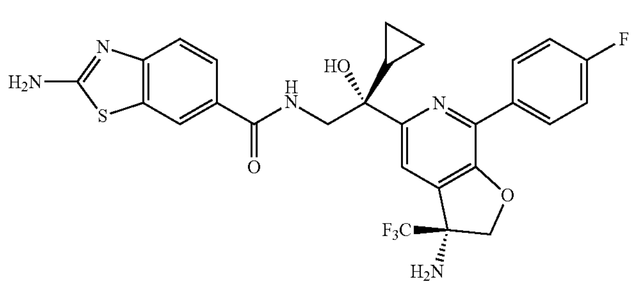 [SMILES: Nc1nc2ccc(C(=O)NC[C@](O)(c3cc4c(c(-c5ccc(F)cc5)n3)OC[C@@]4(N)C(F)(F)F)C3CC3)cc2s1] |

| Compound | Structure |
|---|---|
| 53 | 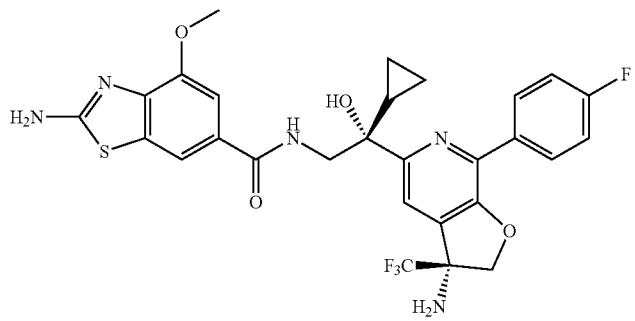 [SMILES: COc1cc(C(=O)NC[C@](O)(c2cc3c(c(-c4ccc(F)cc4)n2)OC[C@@]3(N)C(F)(F)F)C2CC2)cc2sc(N)nc12] |
| 54 | 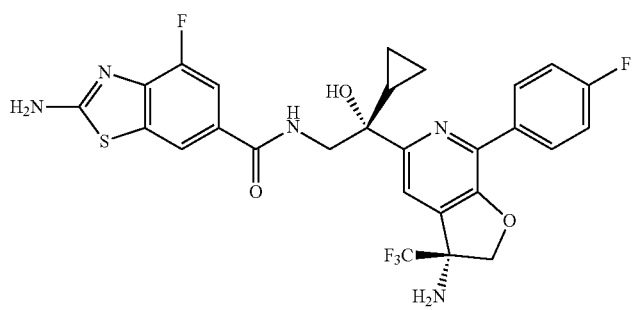 [SMILES: Nc1nc2c(F)cc(C(=O)NC[C@](O)(c3cc4c(c(-c5ccc(F)cc5)n3)OC[C@@]4(N)C(F)(F)F)C3CC3)cc2s1] |
| 55 | 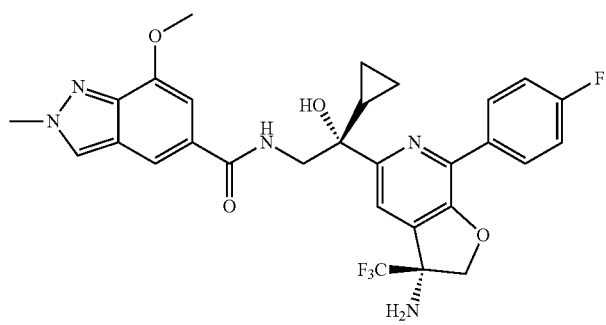 [SMILES: COc1cc(C(=O)NC[C@](O)(c2cc3c(c(-c4ccc(F)cc4)n2)OC[C@@]3(N)C(F)(F)F)C2CC2)cc2cn(C)nc12] |
| 56 | 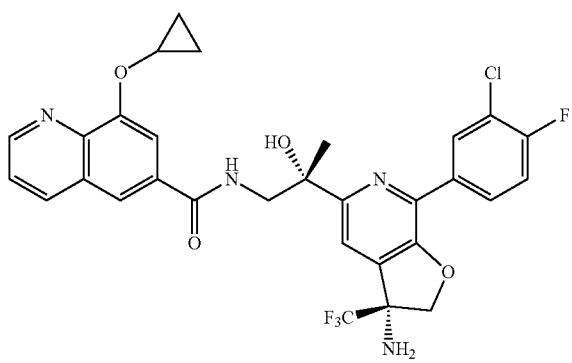 [SMILES: C[C@](O)(CNC(=O)c1cc(OC2CC2)c2ncccc2c1)c1cc2c(c(-c3ccc(F)c(Cl)c3)n1)OC[C@@]2(N)C(F)(F)F] |

| Compound | Structure |
|---|---|
| 57 | 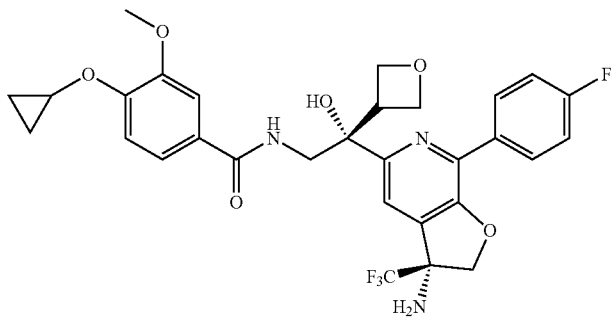 [SMILES: COc1cc(C(=O)NC[C@](O)(c2cc3c(c(-c4ccc(F)cc4)n2)OC[C@@]3(N)C(F)(F)F)C2COC2)ccc1OC1CC1] |
| 58 | 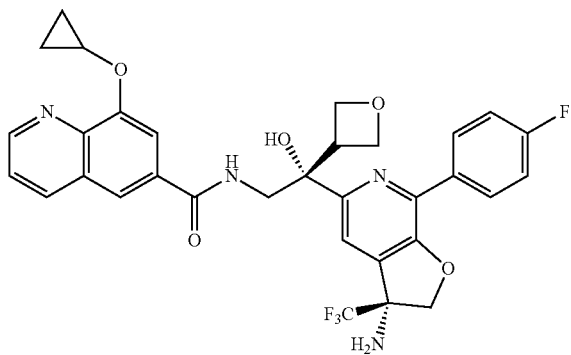 [SMILES: N[C@@]1(C(F)(F)F)COc2c1cc([C@@](O)(CNC(=O)c1cc(OC3CC3)c3ncccc3c1)C1COC1)nc2-c1ccc(F)cc1] |
| 59 | 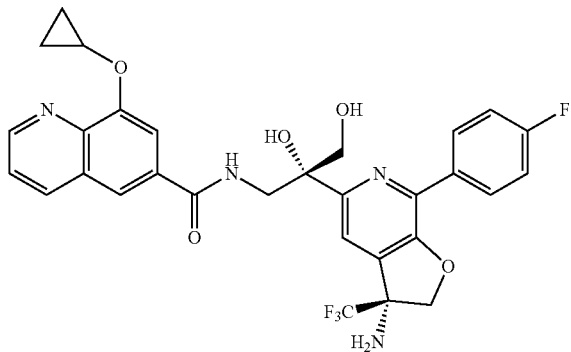 [SMILES: N[C@@]1(C(F)(F)F)COc2c1cc([C@](O)(CO)CNC(=O)c1cc(OC3CC3)c3ncccc3c1)nc2-c1ccc(F)cc1] |
| 60 | 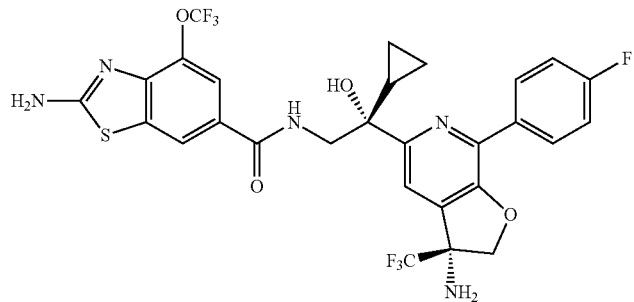 |

| Compound | Structure |
|---|---|
| 61 | 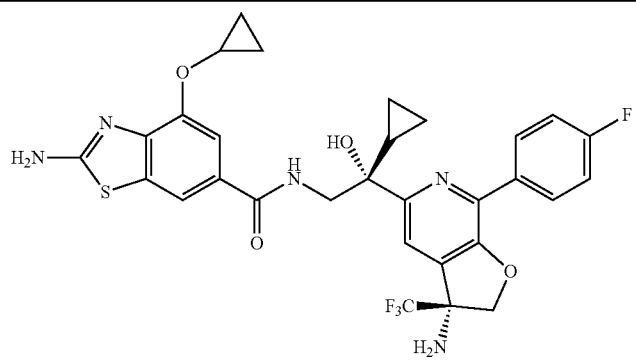 |
| 62 | 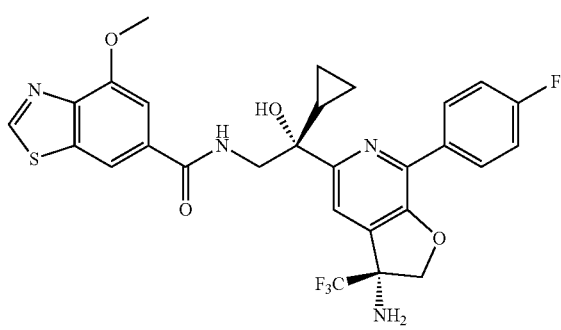 |
| 63 | 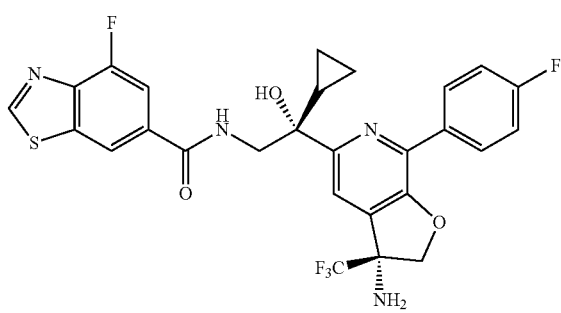 |
| 64 | 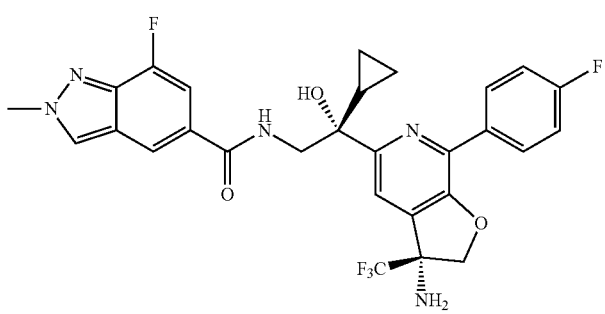 [SMILES: Cn1cc2cc(C(=O)NC[C@](O)(c3cc4c(c(-c5ccc(F)cc5)n3)OC[C@@]4(N)C(F)(F)F)C3CC3)cc(F)c2n1] |
| 65 | 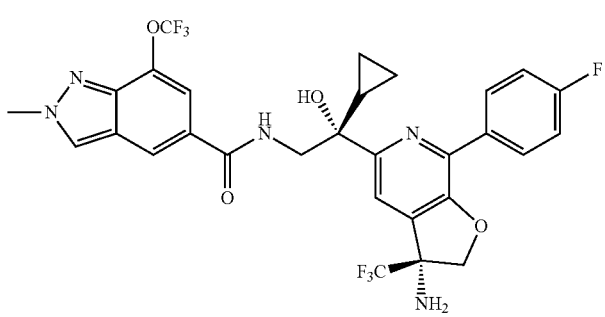 [SMILES: Cn1cc2cc(C(=O)NC[C@](O)(c3cc4c(c(-c5ccc(F)cc5)n3)OC[C@@]4(N)C(F)(F)F)C3CC3)cc(OC(F)(F)F)c2n1] |

| Compound | Structure |
|---|---|
| 66 | 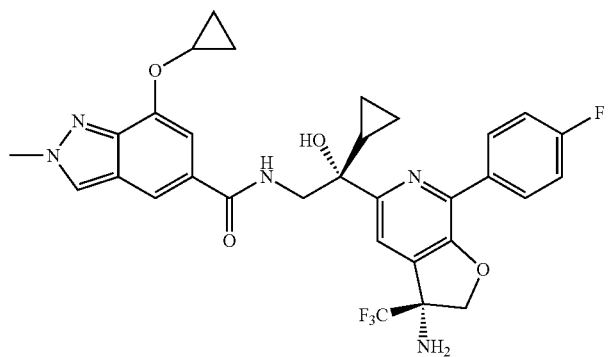 [SMILES: Cn1cc2cc(C(=O)NC[C@](O)(c3cc4c(c(-c5ccc(F)cc5)n3)OC[C@@]4(N)C(F)(F)F)C3CC3)cc(OC3CC3)c2n1] |
| 67 | 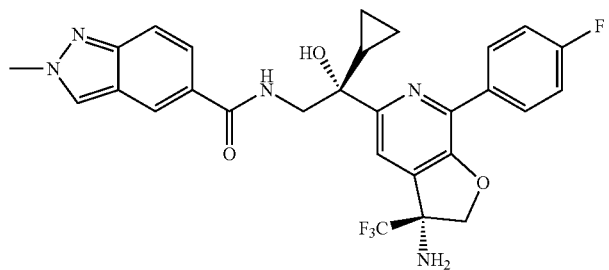 [SMILES: Cn1cc2cc(C(=O)NC[C@](O)(c3cc4c(c(-c5ccc(F)cc5)n3)OC[C@@]4(N)C(F)(F)F)C3CC3)ccc2n1] |
| 68 | 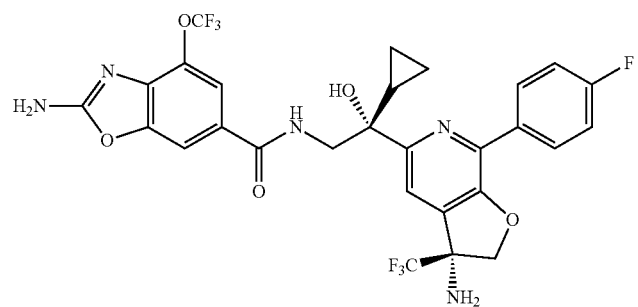 [SMILES: Nc1nc2c(OC(F)(F)F)cc(C(=O)NC[C@](O)(c3cc4c(c(-c5ccc(F)cc5)n3)OC[C@@]4(N)C(F)(F)F)C3CC3)cc2o1] |
| 69 | 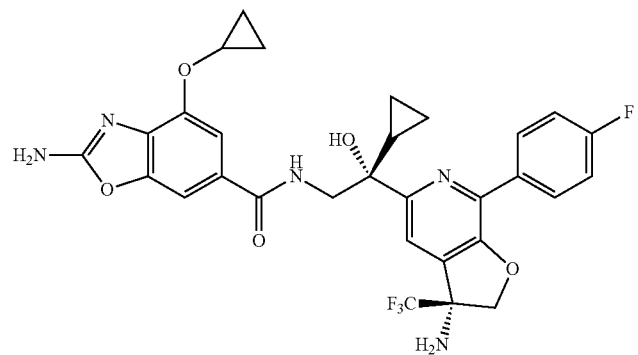 |

US 11,420,976 B2
181                                    182
-continued
| Compound | Structure |
|---|---|
| 70 | 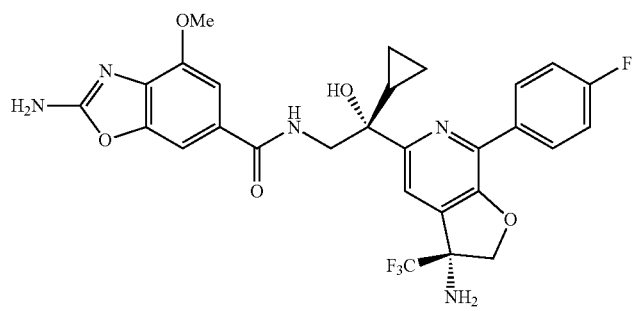 [SMILES: COc1cc(C(=O)NC[C@](O)(c2cc3c(c(-c4ccc(F)cc4)n2)OC[C@@]3(N)C(F)(F)F)C2CC2)cc2oc(N)nc12] |
| 71 | 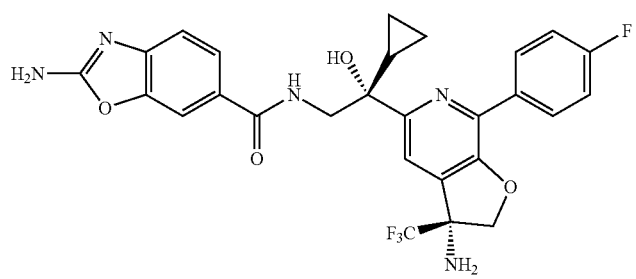 [SMILES: Nc1nc2ccc(C(=O)NC[C@](O)(c3cc4c(c(-c5ccc(F)cc5)n3)OC[C@@]4(N)C(F)(F)F)C3CC3)cc2o1] |
| 72 | 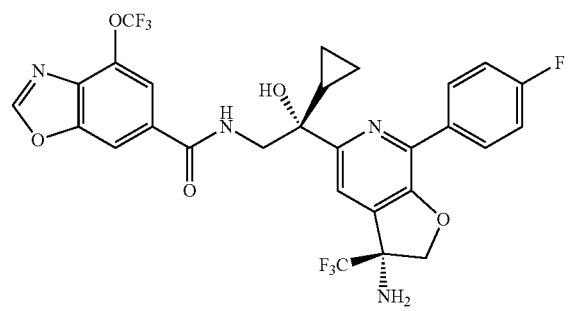 [SMILES: N[C@@]1(C(F)(F)F)COc2c1cc([C@@](O)(CNC(=O)c1cc(OC(F)(F)F)c3ncoc3c1)C1CC1)nc2-c1ccc(F)cc1] |
| 73 | 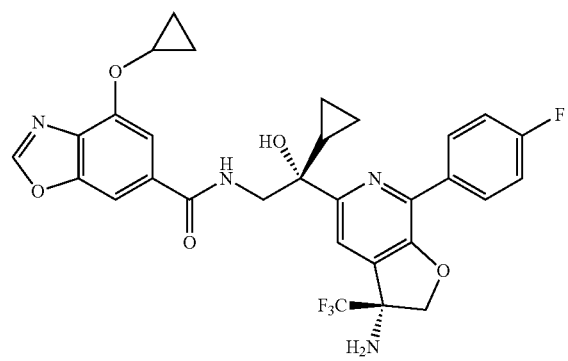 [SMILES: N[C@@]1(C(F)(F)F)COc2c1cc([C@@](O)(CNC(=O)c1cc(OC3CC3)c3ncoc3c1)C1CC1)nc2-c1ccc(F)cc1] |
| 74 | 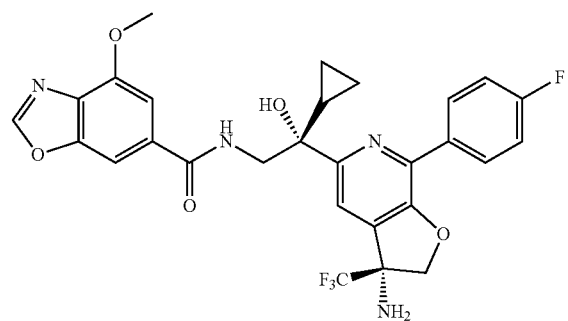 [SMILES: COc1cc(C(=O)NC[C@](O)(c2cc3c(c(-c4ccc(F)cc4)n2)OC[C@@]3(N)C(F)(F)F)C2CC2)cc2ocnc12] |

| Compound | Structure |
|---|---|
| 75 | 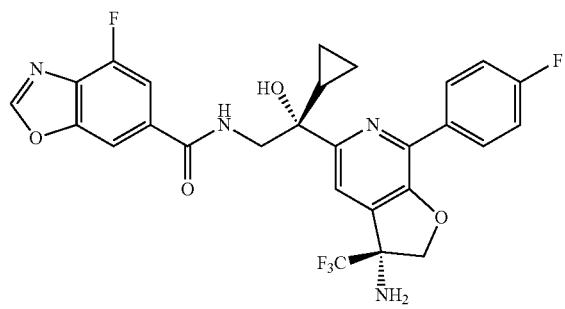 [SMILES: N[C@@]1(C(F)(F)F)COc2c1cc([C@@](O)(CNC(=O)c1cc(F)c3ncoc3c1)C1CC1)nc2-c1ccc(F)cc1] |
| 76 | 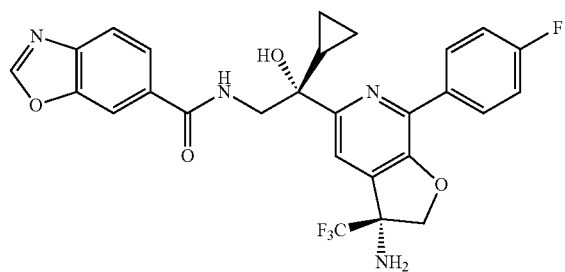 [SMILES: N[C@@]1(C(F)(F)F)COc2c1cc([C@@](O)(CNC(=O)c1ccc3ncoc3c1)C1CC1)nc2-c1ccc(F)cc1] |
| 77 | 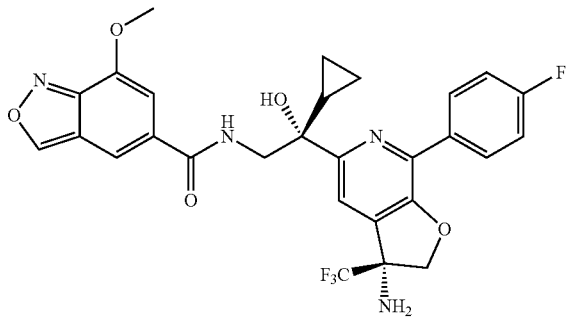 [SMILES: COc1cc(C(=O)NC[C@](O)(c2cc3c(c(-c4ccc(F)cc4)n2)OC[C@@]3(N)C(F)(F)F)C2CC2)cc2conc12] |
| 55c | 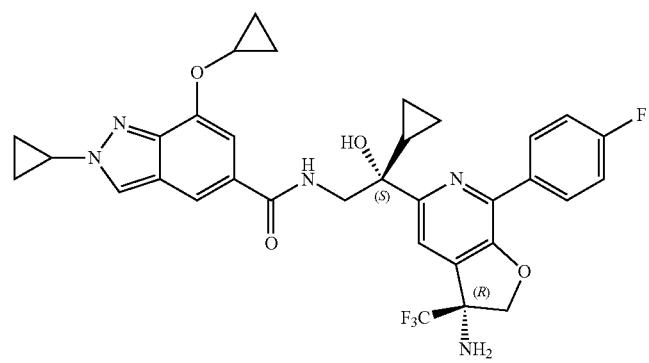 |

-continued
| Compound | Structure |
|---|---|
| 55d | 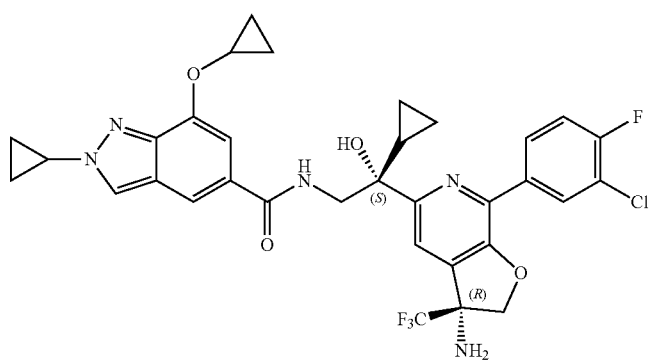 |
| 59b | 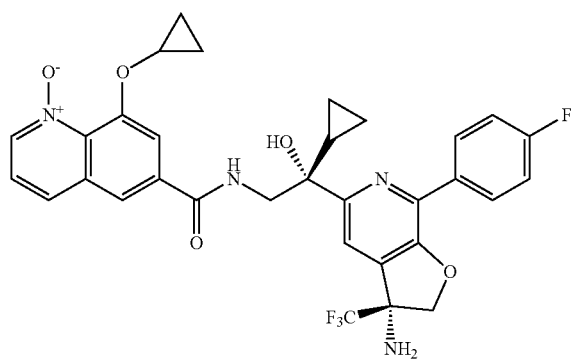 [SMILES: N[C@@]1(C(F)(F)F)COc2c1cc([C@@](O)(CNC(=O)c1cc(OC3CC3)c3c(ccc[n+]3[O-])c1)C1CC1)nc2-c1ccc(F)cc1] |
| 59c | 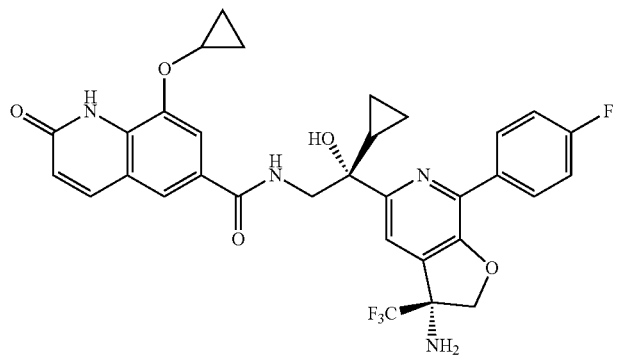 [SMILES: N[C@@]1(C(F)(F)F)COc2c1cc([C@@](O)(CNC(=O)c1cc(OC3CC3)c3[nH]c(=O)ccc3c1)C1CC1)nc2-c1ccc(F)cc1] |
| 59d | 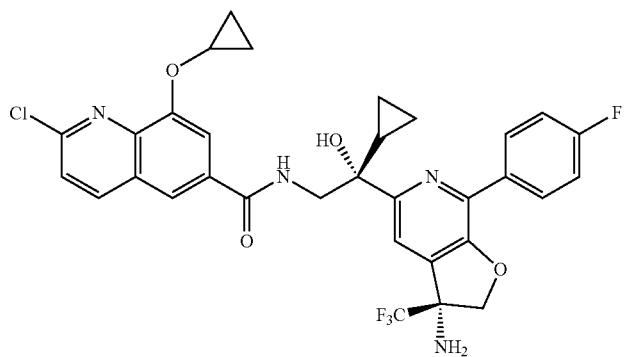 [SMILES: N[C@@]1(C(F)(F)F)COc2c1cc([C@@](O)(CNC(=O)c1cc(OC3CC3)c3nc(Cl)ccc3c1)C1CC1)nc2-c1ccc(F)cc1] |

| Compound | Structure |
|---|---|
| 59e | 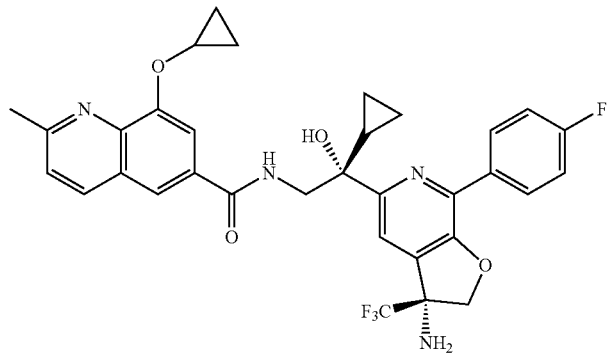 [SMILES: Cc1ccc2cc(C(=O)NC[C@](O)(c3cc4c(c(-c5ccc(F)cc5)n3)OC[C@@]4(N)C(F)(F)F)C3CC3)cc(OC3CC3)c2n1] |
| 78 | 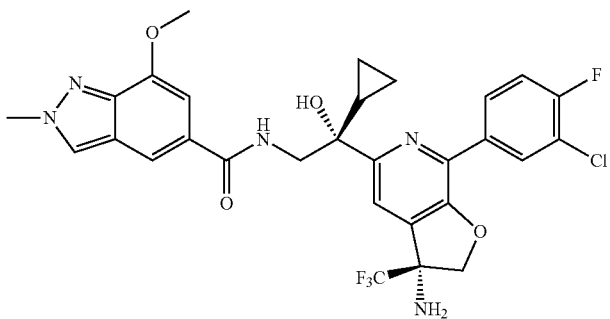 [SMILES: COc1cc(C(=O)NC[C@](O)(c2cc3c(c(-c4ccc(F)c(Cl)c4)n2)OC[C@@]3(N)C(F)(F)F)C2CC2)cc2cn(C)nc12] |
| 79 | 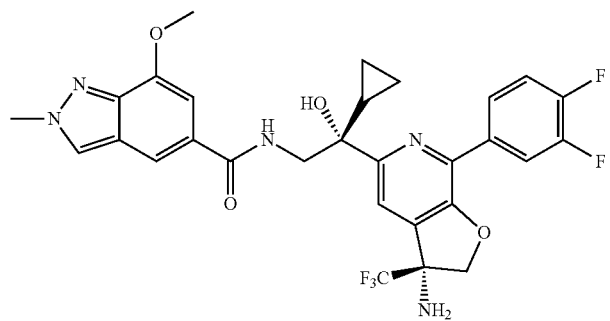 [SMILES: COc1cc(C(=O)NC[C@](O)(c2cc3c(c(-c4ccc(F)c(F)c4)n2)OC[C@@]3(N)C(F)(F)F)C2CC2)cc2cn(C)nc12] |
| 80 | 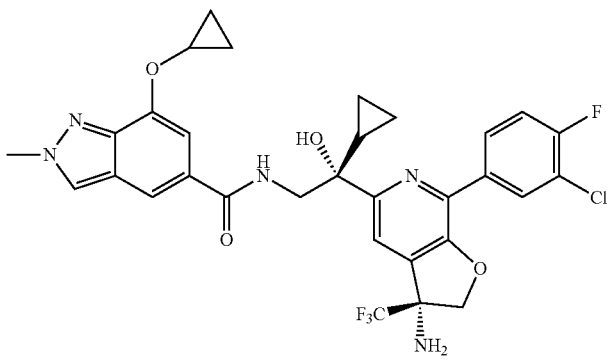 [SMILES: Cn1cc2cc(C(=O)NC[C@](O)(c3cc4c(c(-c5ccc(F)c(Cl)c5)n3)OC[C@@]4(N)C(F)(F)F)C3CC3)cc(OC3CC3)c2n1] |

| Compound | Structure |
|---|---|
| 81 | (structure) |
| 82 | (structure) |
| 83 | (structure) |
| 84 | (structure) |

11. A pharmaceutical composition comprising the compound according to claim 1, or a pharmaceutically acceptable salt thereof, and a pharmaceutically acceptable carrier, diluent or excipient.

12. A method of treating or preventing an RSV infection in a subject in need thereof, comprising administering to the subject a therapeutically effective amount of the compound or a combination of compounds of claim 1.

13. The method of claim 12, further comprising the step of administering to the subject an additional anti-RSV agent.

14. The method of claim 12, further comprising administering to the subject a steroid anti-inflammatory compound.

15. A method of treating RSV and influenza in a subject in need thereof, comprising administering to the subject a therapeutically effective amount of a compound of claim 1 and a therapeutically effective amount of an anti-influenza agent.

16. The method of claim 14, wherein the compound and the additional anti-RSV agent are co-formulated.

17. The method of claim 14, wherein the compound and the additional anti-RSV agent are co-administered.

18. The method of claim 14, wherein the additional anti-RSV agent is administered at a lower dose or frequency as compared to the dose or frequency of the additional anti-RSV agent which is therapeutically effective when administered alone.

19. A method of treating or preventing an HMPV infection in a subject in need thereof, comprising administering to the subject a therapeutically effective amount of a compound or a combination of compounds of claim 1.

20. The method of claim 19, further comprising the step of administering to the subject an additional anti-HMPV agent.

21. The method of claim 19, further comprising administering to the subject a steroid anti-inflammatory compound.

22. The method of claim 20, wherein the compound and the additional anti-HMPV agent are co-formulated.

23. The method of claim 20, wherein the compound and the additional anti-HMPV agent are co-administered.

\* \* \* \* \*

UNITED STATES PATENT AND TRADEMARK OFFICE
CERTIFICATE OF CORRECTION

PATENT NO. : 11,420,976 B2
APPLICATION NO. : 17/155159
DATED : August 23, 2022
INVENTOR(S) : Yong He et al.

Page 1 of 2

It is certified that error appears in the above-identified patent and that said Letters Patent is hereby corrected as shown below:

In the Claims

At Column 145

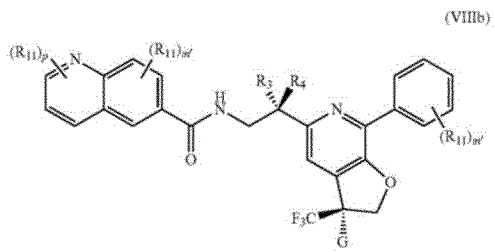

In Claim 7 at Lines 5 through 50, delete "

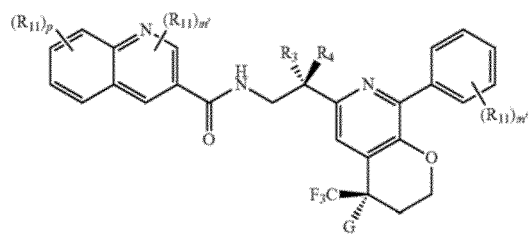 , 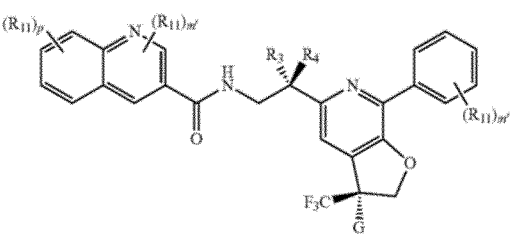 and

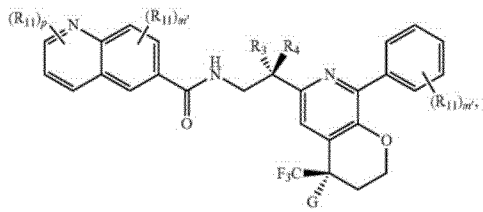

" and insert

Signed and Sealed this
Twenty-first Day of March, 2023

Katherine Kelly Vidal
*Director of the United States Patent and Trademark Office*

CERTIFICATE OF CORRECTION (continued)
U.S. Pat. No. 11,420,976 B2